US008734789B2

(12) United States Patent
DeMore et al.

(10) Patent No.: US 8,734,789 B2
(45) Date of Patent: May 27, 2014

(54) TARGETS FOR REGULATION OF ANGIOGENESIS

(75) Inventors: Nancy Klauber DeMore, Durham, NC (US); Cam Patterson, Chapel Hill, NC (US); Rajendra Bhati, Tampa, FL (US); Bradley G. Bone, Apex, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 148 days.

(21) Appl. No.: 12/945,298

(22) Filed: Nov. 12, 2010

(65) Prior Publication Data
US 2011/0142820 A1 Jun. 16, 2011

Related U.S. Application Data

(63) Continuation-in-part of application No. PCT/US2009/003047, filed on May 15, 2009.

(60) Provisional application No. 61/053,397, filed on May 15, 2008, provisional application No. 61/316,068, filed on Mar. 22, 2010.

(51) Int. Cl.
*A61K 39/395* (2006.01)
*C12P 21/08* (2006.01)
*C07K 16/00* (2006.01)
*A61K 38/00* (2006.01)

(52) U.S. Cl.
USPC ............... 424/130.1; 424/138.1; 424/139.1; 424/142.1; 530/387.3; 530/387.9; 530/388.1; 514/13.3

(58) Field of Classification Search
None
See application file for complete search history.

(56) References Cited

U.S. PATENT DOCUMENTS

| | | | |
|---|---|---|---|
| 5,885,808 A | 3/1999 | Spooner et al. | |
| 6,017,949 A | 1/2000 | D'Amato et al. | |
| 7,026,445 B2 * | 4/2006 | LaVallie et al. | 530/350 |
| 7,304,071 B2 | 12/2007 | Cochran et al. | |
| 7,348,335 B2 | 3/2008 | Bethiel et al. | |
| 7,348,418 B2 | 3/2008 | Singh et al. | |
| 7,465,449 B2 | 12/2008 | Violette et al. | |
| 2001/0018186 A1 | 8/2001 | Hirth | |
| 2002/0006966 A1 | 1/2002 | Arbiser | |
| 2002/0019382 A1 | 2/2002 | Snyder et al. | |
| 2002/0086341 A1 | 7/2002 | Nguyen | |
| 2004/0009541 A1 | 1/2004 | Singh et al. | |
| 2004/0077544 A1 | 4/2004 | Varner | |
| 2005/0250163 A1 | 11/2005 | Lorens et al. | |
| 2006/0269921 A1 | 11/2006 | Segara et al. | |
| 2007/0054271 A1 | 3/2007 | Polyak et al. | |
| 2007/0087365 A1 | 4/2007 | Van Criekinge et al. | |
| 2007/0105133 A1 | 5/2007 | Clarke et al. | |
| 2007/0161018 A1 | 7/2007 | Inazawa et al. | |
| 2007/0184439 A1 | 8/2007 | Guilford et al. | |
| 2007/0243214 A1 | 10/2007 | Schiemann et al. | |
| 2007/0258952 A1 | 11/2007 | Tong et al. | |

FOREIGN PATENT DOCUMENTS

| | | |
|---|---|---|
| EP | 1733739 A1 | 12/2006 |
| WO | WO 02/24957 A1 | 3/2002 |

OTHER PUBLICATIONS

Ngo et al. (1994), The Protein Folding Problem and Tertiary Structure Prediction, pp. 491-495.*
Wells et al. (1990), Biochemistry, vol. 29, No. 37, pp. 8509-8517.*
Lescher et al. (1998), Development Dynamics, Vo. 213, pp. 440-451.*
Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Adam et al., "Arylamine N-acetyl-transferase-1 is highly expressed in breast cancers and conveys enhanced growth and resistance to etoposide in vitro," Mol. Cancer. Res. 1:826-835 (2003).
Allinen et al., "Molecular characterization of the tumor microenvironment in breast cancer," Cancer Cell 6:17-32 (2004).
Bhati et al., "Discovery of Novel Tumor Endothelial Markers in Breast Cancer", Presentation and Abstract, Society of Surgical Oncology (SSO) 60th Annual Cancer Symposium, Mar. 16, 2007, Washington, D.C.
Bhati et al., "Molecular Characterization of Human Breast Cancer Endothelium," Surgical Grand Rounds, UNC Lineberger Comprehensive Cancer Center, Feb. 28, 2007.
Bhati et al., "Molecular Characterization of Human Breast Tumor Vascular Cells," Am. J. Pathol. 172:1381-1390 (2008) epub Apr. 10, 2008.
Bhati et al., "A Novel Technique for Laser Capture Microdissection of Tumor Endothelium for mRNA Analysis," American Association for Cancer Research Special Conference on Angiogenesis and Drug Delivery to Tumors: Bench to Bedside and Back, Waltham, MA, Nov. 9-13, 2005.
Buckanovich et al., "Tumor vascular proteins as biomarkers in ovarian cancer," J. Clin. Oncol. 25:852-861 (2007).
Cance et al., "Protein kinases in human breast cancer," Breast Cancer Res. Treat. 35: 105-114 (1995).

(Continued)

*Primary Examiner* — Christine J Saoud
*Assistant Examiner* — Jegatheesan Seharaseyon
(74) *Attorney, Agent, or Firm* — Myers Bigel Sibley & Sajovec, P.A.

(57) ABSTRACT

The present invention relates to the identification of polynucleotides and polypeptides having increased expression in tumor blood vessels. The invention further relates to the use of the identified polynucleotides and polypeptides, and inhibitors of the polynucleotides and polypeptides, in the regulation of angiogenesis and the diagnosis and treatment of angiogenesis-related diseases such as cancer.

9 Claims, 24 Drawing Sheets

(56) References Cited

OTHER PUBLICATIONS

Cao et al., "gro-beta, a -C-X-C- chemokine, is an angiogenesis inhibitor that suppresses the growth of Lewis lung carcinoma in mice," J. Exp. Med. 182:2069-2077 (1995).

Cao et al., "Only low levels of exogenous N-acetyltransferase can be achieved in transgenic mice," Pharmacogenomics J. 5:255-261 (2005).

Chen et al., "Curcumin inhibited the arylamines N-acetyltransferase activity, gene expression and DNA adduct formation in human lung cancer cells (A549)," Toxicol. In Vitro 17: 323-333 (2003).

Dufourcq et al., "FrzA, a secreted frizzled related protein, induced angiogenic response," Circulation 106:3097-3103 (2002).

EP09747001.7 European Extended Search Report (EESR) mailed Apr. 18, 2012.

Goodman at al., "Seprase, a membrane-bound protease alleviates the serum growth requirement of human breast cancer cells," Clin. Exp. Metastasis 20:459-470 (2003).

Huang et al., "Seprese promotes rapid tumor growth and increased microvessel density in a mouse model of human breast cancer," Cancer Res. 64: 2712-2716 (2004).

International Application No. PCT/US2011/29301 International Search Report & Written Opinion (ISR/WO) mailed Jul. 26, 2011.

International Application No. PCT/US2009/003047 International Search Report & Written Opinion (ISR/WO) mailed Nov. 17, 2010.

International Preliminary Report on Patentability (IPRP) for International Application No. PCT/US2009/003047, mailed Nov. 25, 2010.

Kawamoto et al., "DNA methylation and histone modifications cause silencing of Wnt antagonist gene in human renal cell carcinoma cell lines," Int. J. Cancer 123:535-542 (2008).

Krejsgaard et al., "Jak3- and JNK-dependent vascular endothelial growth factor expression in cutaneous T-cell lymphoma," Leukemia 20:1759-1766 (2006).

Kunnumakkara et al., "Curcumin inhibits proliferation, invasion, angiogenesis and metstasis of different cancers through interaction with multiple cell signaling proteins," Cancer Lett 269:199-225 (2008).

Lee et al., "Secreted frizzled-reiated protein 2 (SFRP2) is highly expressed in canine mammary gland tumors but rot in normal mammary glands," Breast Cancer Res. Treat. 84:139-149 (2004).

Loeffler et al., "Targeting tumor-associated fibroblasts improves cancer chemotherapy by increasing intratumoral drug uptake," J. Clin. Invest. 116:1955-1962 (2006).

Madden et al., "Vascular gene expression in nonneoplastic and malignant brain," Am. J. Pathol. 165:601-608 (2004).

Medyouf et al., "Targeting calcineurin activation as a therapeutic strategy for t-cell acute lymphoblastic leukemia," Nat. Med. 13:736-741 (2007).

Parker et al., "Alterations in vascular gene expression in invasive breast carcinoma," Cancer Res. 64:7857-7866 (2004).

Ragunathan et al., "Identification of the Xenobiotic-Metabolizing Enzyme Arylamine N-Acetyltransferase 1 as a New Target of Cisplatin in Breast Cancer Cells: Molecular and Cellular Mechanisms of Inhibition," Mol. Pharmacol. 73:1761-1768 (2008).

Shafqat et al. "Hep27, a member of the short-chain dehydrogenase/reductase family, is an NADPH-dependent dicarbonyl reductase expressed in vascular endothelial tissue," Cell Mol. Life Sci. 63:1205-1213 (2006).

Srisuma et al., "Identification of genes promoting angiogenesis in mouse lung by transcriptional profiling," Am. J. Resp. Cell Mol. Biol. 29:172-179 (2003).

St Croix et al., "Genes expressed in human tumor endothelium," Science 289:1197-1202 (2000).

Wakefield et al., "Arylamine N-acetyltransferase 2 expression in the developing heart," J. Histochem. Cytochem. 53:583-592 (2005).

Wawrzak et al., "Wnt3a binds to severai sFRPs in the nanomolar range," Biochem. Biophys. Res. Commun. 357:1119-1123 (2007).

Yeh et al., "The Inhibition of N-Acetyltransferase Activity and Gene Expression in Human Bladder Cancer Cells (T24) by Shikonin" In vivo 18:21-32 (2004).

Becker et al., "The carcinogenic potential of tacrolimus ointment beyond immune suppression: a hypothesis creating case report," BMC Cancer 6:7 (2006).

Deb et al., "SFRP2 regulates cardiomyogenic differentiation by inhibiting a positive transcriptional autofeedback loop of Wnt3a," Stem Cells 26:35-44 (2008).

E-mail from Katherine Moore, Ph.D. dated Jul. 21, 2013, confirming the date of receipt of the 4th annual report for grant W81XWH-04-1-0434 to Nancy Klauber-DeMore, M.D.

Klauber-DeMore, "Functional and molecular characterization of SFRP2 in angiogenesis," University Cancer Research Fund (2007), http://ucrf.unc.edu/awards/abstract.asp?ID=66&year=2007, retrieved Apr. 23, 2013.

Klauber-DeMore,"Characterization of gene expression in human breast tumor epithelium," Annual summary report for grant W81XWH-04-1-0434, pp. 1-15 (May 1, 2008).

Yarosh et al., "Calcineurin inhibitors decrease DNA repair and apoptosis in human keratinocytes following ultraviolet B irradiation," J. Invest. Dermatol. 125:1020-1025 (2005).

\* cited by examiner

FIG. 7
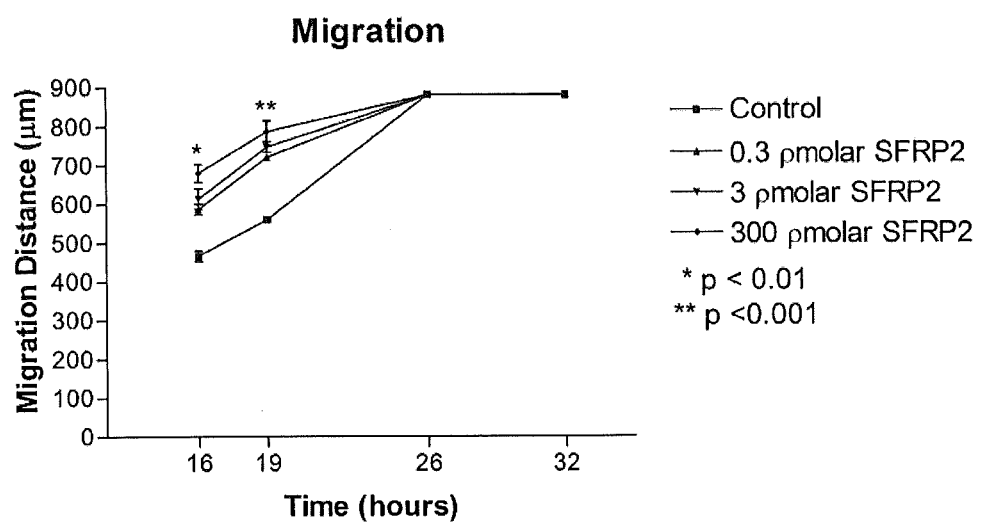
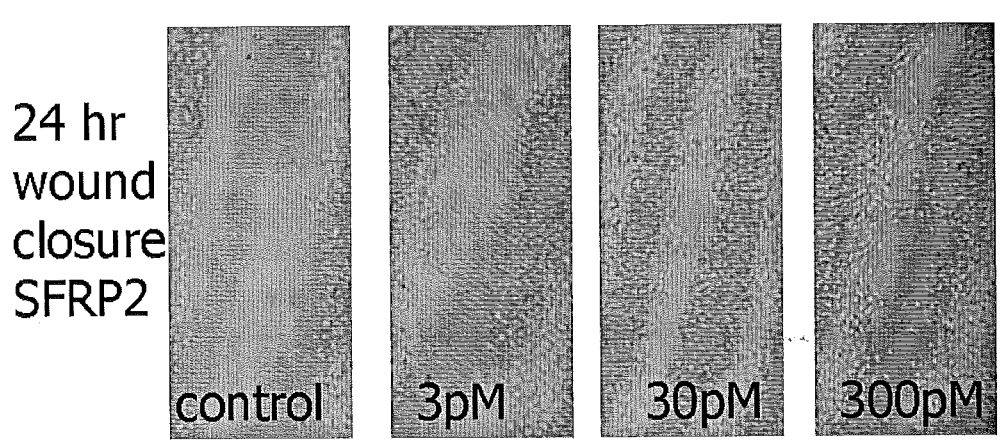

FIG. 8
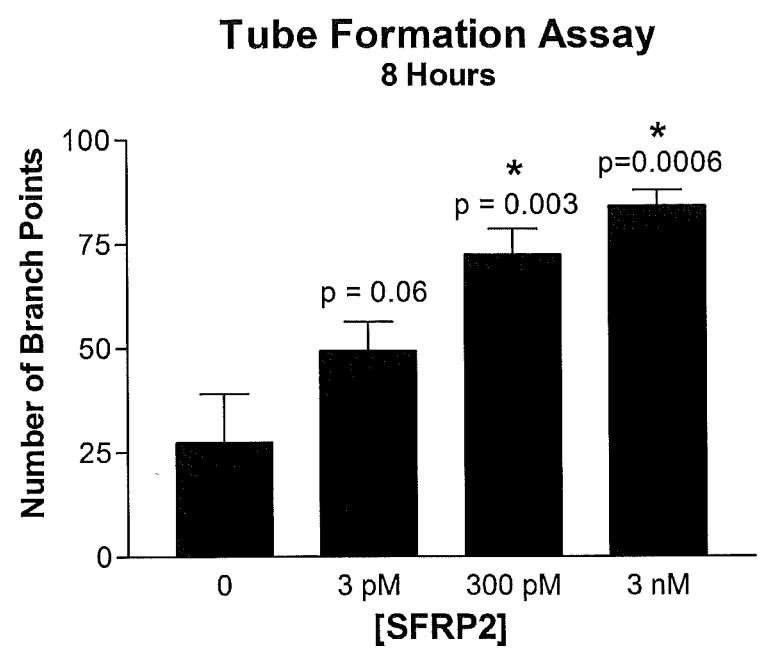
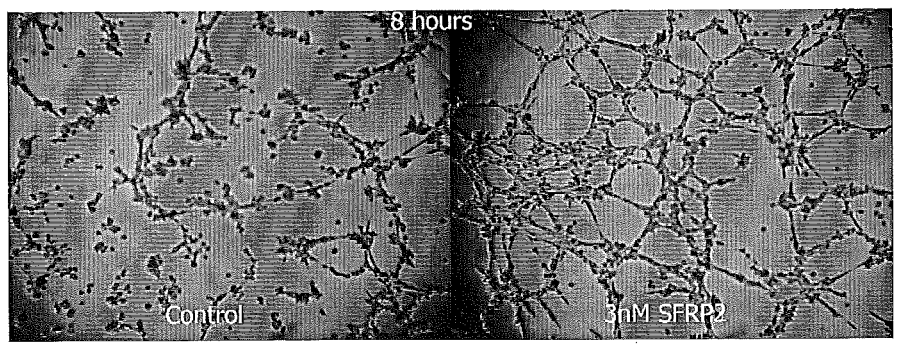

FIG. 13
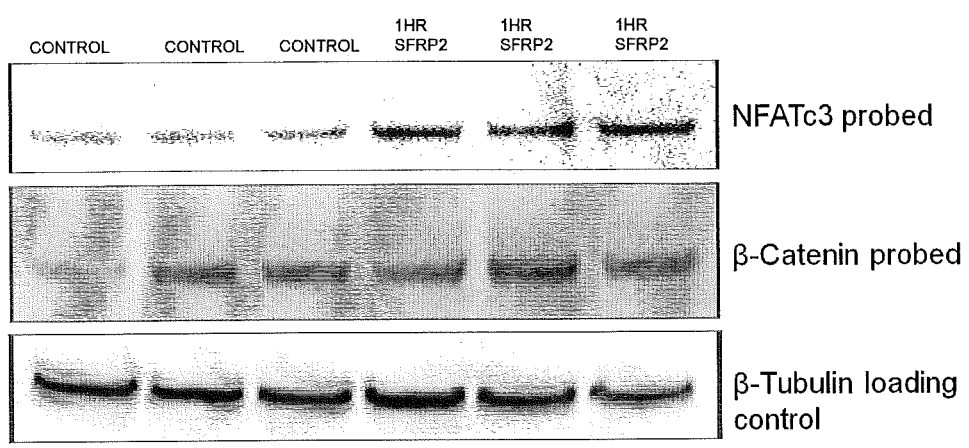
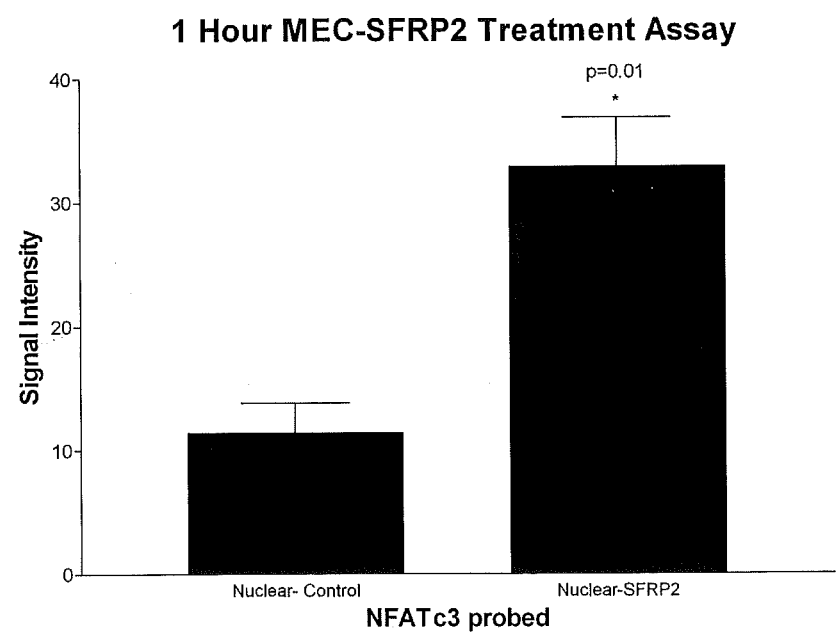

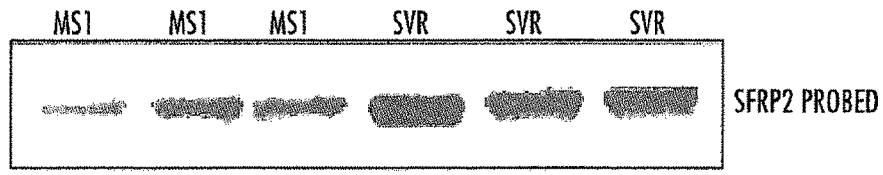
FIG. 16
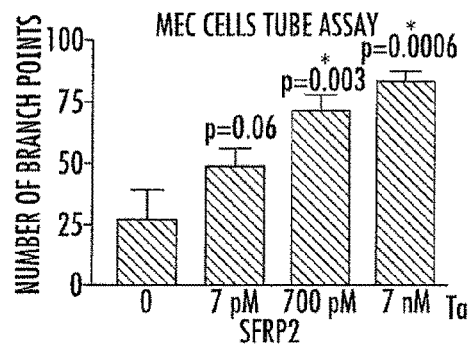
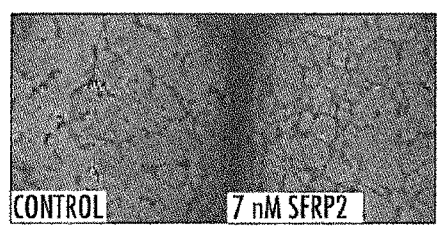
FIG. 17A
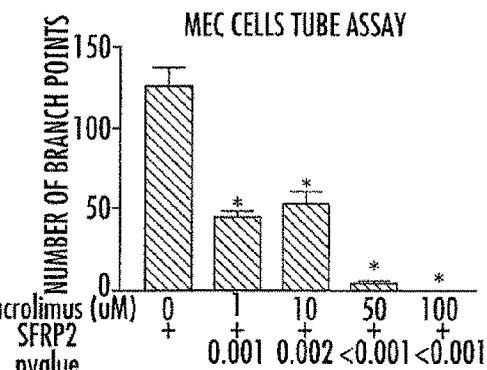
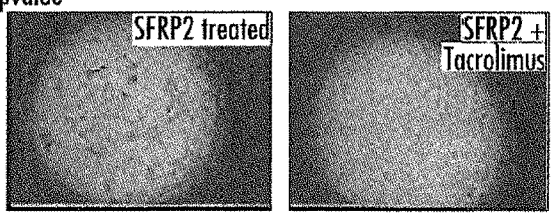
FIG. 17B
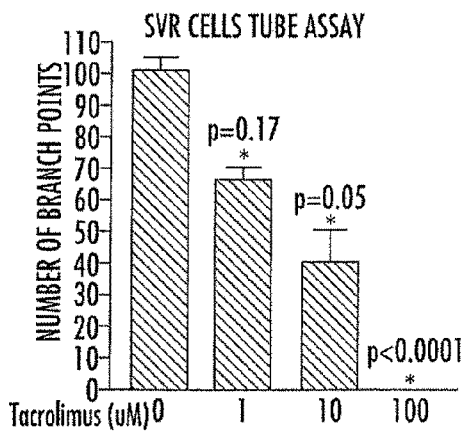
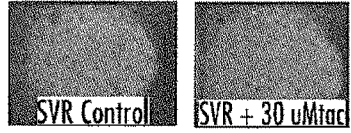
FIG. 17C
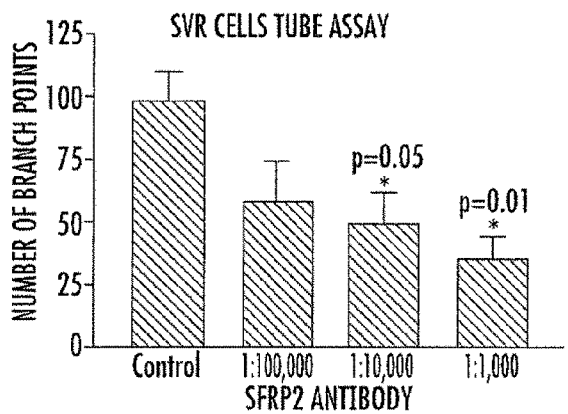
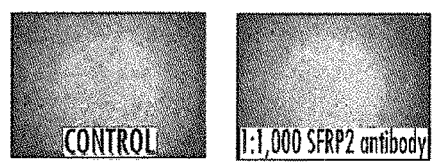
FIG. 17D FIG. 22
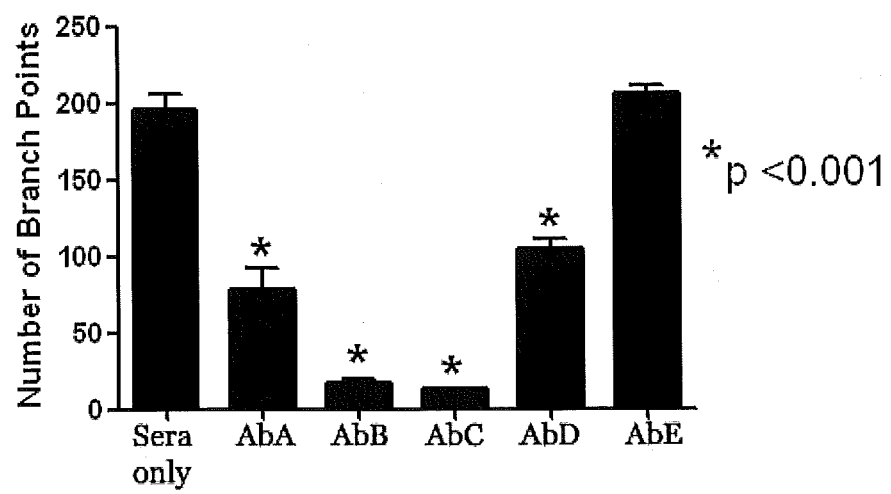
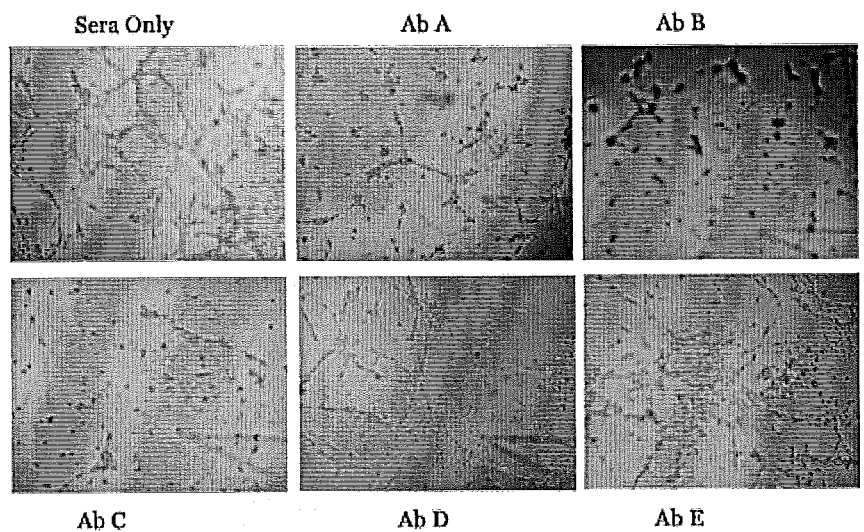

| Tumor Type | Vessel Intensity* | % Vessels Staining** |
|---|---|---|
| Angiosarcoma | 9 (3+) | 7 (4+)<br>2 (3+) |
| Prostate Cancer | 7 (3+) | 5 (3+)<br>2 (2+) |
| Hepatocellular Cancer | 7 (3+) | 7 (3+) |
| Colon Cancer | 8 (3+) | 6 (3+)<br>2 (2+) |
| Clear Cell Renal Cancer | 8 (3+) | 5 (4+)<br>3 (3+) |
| Lung Cancer | 8 (3+) | 2 (4+)<br>6 (3+) |
| Ovarian Cancer | 8 (4+) | 4 (4+)<br>4 (3+) |
| Pancreatic Cancer | 6 (3+) | 1 (4+)<br>5 (3+) |

*Vessel Intensity 3+ = moderate/ strong staining
**% Vessels Staining
   4+ = 75-100% vessels staining
   3+ = 50-74% vessels staining
   2+ = 25-49% vessels staining

FIG. 25

Effect of Tacrolimus on MMTV-Neu Mouse Tumor Growth

SEQUENCE LISTING

```
<160> NUMBER OF SEQ ID NOS: 16

<210> SEQ ID NO 1
<211> LENGTH: 11
<212> TYPE: PRT
<213> ORGANISM: Homo sapiens

<400> SEQUENCE: 1
```

-continued

Gly Gln Pro Asp Phe Ser Tyr Arg Ser Asn Cys
1               5                   10

<210> SEQ ID NO 2
<211> LENGTH: 12
<212> TYPE: PRT
<213> ORGANISM: Homo sapiens

<400> SEQUENCE: 2

Lys Gln Cys His Pro Asp Thr Lys Lys Glu Leu Cys
1               5                   10

<210> SEQ ID NO 3
<211> LENGTH: 7
<212> TYPE: PRT
<213> ORGANISM: Homo sapiens

<400> SEQUENCE: 3

Val Gln Val Lys Asp Arg Cys
1               5

<210> SEQ ID NO 4
<211> LENGTH: 15
<212> TYPE: PRT
<213> ORGANISM: Homo sapiens

<400> SEQUENCE: 4

Asp Met Leu Glu Cys Asp Arg Phe Pro Gln Asp Asn Asp Leu Cys
1               5                   10                  15

<210> SEQ ID NO 5
<211> LENGTH: 18
<212> TYPE: PRT
<213> ORGANISM: Homo sapiens

<400> SEQUENCE: 5

Glu Ala Cys Lys Asn Lys Asn Asp Asp Asn Asp Ile Met Glu Thr
1               5                   10                  15

Leu Cys

<210> SEQ ID NO 6
<211> LENGTH: 20
<212> TYPE: PRT
<213> ORGANISM: Homo sapiens

<400> SEQUENCE: 6

Glu Ile Thr Tyr Ile Asn Arg Asp Thr Lys Ile Ile Leu Glu Thr Lys
1               5                   10                  15

Ser Lys Thr Cys
            20

<210> SEQ ID NO 7
<211> LENGTH: 26
<212> TYPE: PRT
<213> ORGANISM: Homo sapiens

<400> SEQUENCE: 7

Ile Thr Ser Val Lys Arg Trp Gln Lys Gly Gln Arg Glu Phe Lys Arg
1               5                   10                  15

Ile Ser Arg Ser Ile Arg Lys Leu Gln Cys
            20                  25

<210> SEQ ID NO 8
<211> LENGTH: 37

```
<212> TYPE: PRT
<213> ORGANISM: Artificial
<220> FEATURE:
<223> OTHER INFORMATION: Synthetic antigenic peptide

<400> SEQUENCE: 8

Cys Ser Arg Pro Arg Lys Val Leu Val Glu Gln Thr Lys Asn Glu Tyr
1               5                   10                  15

Phe Glu Leu Lys Ala Asn Leu His Ala Glu Pro Asp Tyr Leu Glu Val
            20                  25                  30

Leu Glu Gln Gln Thr
        35

<210> SEQ ID NO 9
<211> LENGTH: 27
<212> TYPE: PRT
<213> ORGANISM: Artificial
<220> FEATURE:
<223> OTHER INFORMATION: Synthetic antigenic peptide

<400> SEQUENCE: 9

Thr Ser Lys Ser Ser Gly Gln Lys Gly Arg Lys Glu Leu Leu Lys Gly
1               5                   10                  15

Asn Gly Arg Arg Ile Asp Tyr Met Leu His Cys
            20                  25

<210> SEQ ID NO 10
<211> LENGTH: 19
<212> TYPE: RNA
<213> ORGANISM: Artificial
<220> FEATURE:
<223> OTHER INFORMATION: siRNA sequence

<400> SEQUENCE: 10
gagauaacgu acaucaaca                                              19

<210> SEQ ID NO 11
<211> LENGTH: 19
<212> TYPE: RNA
<213> ORGANISM: Artificial
<220> FEATURE:
<223> OTHER INFORMATION: siRNA sequence

<400> SEQUENCE: 11
caagcugcaa ugcuaguuu                                              19

<210> SEQ ID NO 12
<211> LENGTH: 19
<212> TYPE: RNA
<213> ORGANISM: Artificial
<220> FEATURE:
<223> OTHER INFORMATION: siRNA sequence

<400> SEQUENCE: 12
ccaugucagg cgaauuguu                                              19

<210> SEQ ID NO 13
<211> LENGTH: 120
<212> TYPE: PRT
<213> ORGANISM: Artificial
<220> FEATURE:
<223> OTHER INFORMATION: Heavy chain variable region sequence

<400> SEQUENCE: 13

Gln Val Gln Leu Gln Gln Pro Gly Ala Glu Leu Val Gln Pro Gly Ala
1               5                   10                  15
```

```
Ser Val Met Leu Ser Cys Lys Ala Ser Gly Phe Thr Phe Thr Arg Tyr
        20                  25                  30

Trp Trp His Trp Val Arg Gln Thr Pro Gly Arg Gly Leu Glu Trp Ile
        35                  40                  45

Gly Arg Ile Asp Pro Asn Ser Gly Thr Thr Arg Phe Ile Glu Lys Phe
50                      55                  60

Lys Thr Lys Ala Thr Leu Thr Val Asp Lys Pro Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Trp Gly Pro Tyr Tyr Gly Tyr Ala Met Asp Tyr Trp Gly Pro
                100                 105                 110

Gly Thr Ser Val Thr Val Ser Ser
        115                 120

<210> SEQ ID NO 14
<211> LENGTH: 360
<212> TYPE: DNA
<213> ORGANISM: Artificial
<220> FEATURE:
<223> OTHER INFORMATION: Heavy chain variable region sequence

<400> SEQUENCE: 14
caggtccaat tgcagcagcc tggggctgag cttgtgcagc ctggggcttc agtgatgctg      60
tcctgcaagg cttctggttt caccttcacc aggtattggt ggcactgggt gaggcagacg     120
cctggacgag gccttgagtg gattggaagg attgatccta atagtggtac tactaggttc     180
attgagaagt tcaagaccaa ggccacactg actgtagaca aaccctccag cacagcctac     240
atgcacctca gcagtctcac atctgaagac tctgcggtct attattgtgc aagatggggg     300
ccctactacg gctatgctat ggactactgg ggtccaggaa cctcagtcac cgtctcctca     360

<210> SEQ ID NO 15
<211> LENGTH: 106
<212> TYPE: PRT
<213> ORGANISM: Artificial
<220> FEATURE:
<223> OTHER INFORMATION: Light chain variable region sequence

<400> SEQUENCE: 15

Gln Ile Val Leu Thr Gln Ser Pro Ala Ile Met Ser Ala Ser Pro Gly
1               5                   10                  15

Gln Lys Val Thr Ile Thr Cys Ser Ala Ser Ser Val Thr Tyr Met
        20                  25                  30

His Trp Tyr Gln Gln Lys Leu Gly Ser Ser Pro Lys Leu Trp Ile Tyr
        35                  40                  45

Asp Thr Ser Arg Leu Ala Pro Gly Ser Pro Ala Arg Phe Ser Gly Ser
50                  55                  60

Gly Ser Gly Thr Ser Tyr Ser Leu Thr Ile Ser Ser Met Glu Thr Glu
65                  70                  75                  80

Asp Ala Ala Ser Tyr Phe Cys His Gln Trp Ser Thr Tyr Pro Pro Thr
                85                  90                  95

Phe Gly Thr Gly Thr Lys Leu Glu Ile Gln
                100                 105

<210> SEQ ID NO 16
<211> LENGTH: 318
<212> TYPE: DNA
<213> ORGANISM: Artificial
```

```
<220> FEATURE:
<223> OTHER INFORMATION: Light chain variable region sequence

<400> SEQUENCE: 16
caaattgttc tcacccagtc tccagcaatc atgtctgcat ctccagggca gaaagtcacc      60
ataacctgca gtgccagttc aagtgttact tacatgcact ggtatcagca gaagttagga     120
tcctccccca aactctggat ttatgacaca tccagactgg ctcctggatc ccctgctcgc     180
ttcagtggca gtgggtctgg aacctcttac tctctcacaa tcagcagcat ggagactgaa     240
gatgctgcct cttatttctg ccatcagtgg agtacttacc cgcccacgtt cggcacgggg     300
acaaaattgg aaatacaa                                                   318
```

TARGETS FOR REGULATION OF ANGIOGENESIS

RELATED APPLICATIONS

This application is a continuation-in-part application of, and claims priority to, International Application No. PCT/US2009/003047; filed on May 15, 2009, which claims the benefit of U.S. Provisional Application No. 61/053,397, filed May 15, 2008. This application also claims priority to U.S. Provisional Application No. 61/316,068, filed Mar. 22, 2010. The entire contents of each of these applications is fully incorporated herein by reference.

STATEMENT OF FEDERAL SUPPORT

This invention was made with government support under Grant Nos. CA098034 and CA058223 awarded by the National Institutes of Health and Grant No. W81XWH-04-1-0434 awarded by the Department of Defense. The government has certain rights in the invention.

FIELD OF THE INVENTION

The present invention relates to the identification of polynucleotides and polypeptides having increased expression in tumor blood vessels. The invention further relates to the use of the identified polynucleotides and polypeptides, and inhibitors of the polynucleotides and polypeptides, in the regulation of angiogenesis and the diagnosis and treatment of angiogenesis-related diseases such as cancer.

BACKGROUND OF THE INVENTION

Angiogenesis is the growth of new capillary blood vessels, and is a critical component of solid tumor growth (Folkman, *N. Engl. J. Med.* 285:1182 (1971)). Targeted anti-angiogenic therapy for metastatic breast cancer with bevacizumab, a monoclonal antibody to vascular endothelial growth factor (VEGF), has shown efficacy in patients with metastatic breast cancer (Miller, E2100 Study. Scientific session on monoclonal antibody therapy in breast cancer. Ann. Mtg. Am. Soc. Clin, Oncol. 8-29-2005) and validated the approach of anti-angiogenesis therapy for this disease. Although VEGF is one critical growth factor involved in breast cancer angiogenesis (Schneider et al., *Nat. Clin. Pract. Oncol.* 4:181 (2007)), a more detailed understanding of the assortment of genes that are expressed in breast tumor vessels may facilitate the development of novel molecularly targeted antiangiogenic agents.

Several studies have established evidence to suggest that blood vessels supplying tumors express genes not shared by blood vessels that reside in normal tissues (Buckanovich et al., *J. Clin. Oncol.* 25:852 (2007); Madden et al., *Am. J. Pathol.* 165:601 (2004); Parker et al., *Cancer Res.* 64:7857 (2004); St. Croix et al., *Science* 289:1197 (2000)). St. Croix et al. used a tissue dissociation and cell immunopurification approach to isolate tumor and normal endothelial cells, and then compared gene expression patterns of endothelial cells derived from one colorectal cancer and normal colonic mucosa from the same patient (St. Croix et al., *Science* 289:1197 (2000)). Using serial analysis of gene expression, this analysis identified 46 transcripts, named tumor endothelial markers (TEMs), which were significantly up-regulated in tumor compared with normal endothelium. Using a similar method, Parker et al. isolated endothelial cells from two human breast tumors and one normal reduction mammoplasty and identified genes that were differentially expressed compared to normal breast tissue (Parker et al., *Cancer Res.* 64:7857 (2004)). This study identified 30 breast tumor vascular genes, of which HEYL and PRL3 were confirmed to be localized in endothelium by in situ hybridization. These studies have also shown tumor specific differences in tumor endothelial markers between colon, breast, and brain tumors. Buckanovich et al. subsequently used laser capture microdissection of vessel cells from ovarian cancer and normal ovaries and identified 70 differentially expressed TEMs (Buckanovich et al., *J. Clin. Oncol.* 25:852 (2007)).

Gene expression studies using DNA microarrays have identified several distinct breast cancer subtypes (Perou et al., *Nature* 406:747 (2000)) that differentiate breast cancers into separate groups that differ markedly in prognosis (Sorlie et al., *Proc. Natl. Acad. Sci. USA* 98:10869 (2001)). The intrinsic subtypes include 2 main subtypes of estrogen receptor (ER) negative tumors: Basal subtype (ER negative and Her2/neu negative) and Her2/neu subtype (Her2/neu positive and ER negative); and an ER positive (luminal subtype). Given that TEMs differ between tumor types, and that breast cancers are molecularly heterogeneous, it is desirable to determine whether TEMs differ within the different molecular subtypes of breast cancer.

The present invention addresses previous shortcomings in the art by providing novel angiogenesis targets that can be used for diagnostic and therapeutic methods.

SUMMARY OF THE INVENTION

The present invention is based, in part, on the identification of polynucleotides and polypeptides having increased expression in blood vessels in tumors and the role they play in angiogenesis. The invention is based further on the use of these polynucleotides and polypeptides, and inhibitors thereof, in the regulation of angiogenesis and the diagnosis and treatment of diseases related to angiogenesis.

Accordingly, as one aspect, the invention provides methods of inhibiting angiogenesis in a cell, comprising decreasing the expression and/or activity of one or more polypeptides listed in Table 1 in the cell.

In a further aspect, the invention provides methods of inhibiting angiogenesis in a tissue of a subject, comprising decreasing the expression and/or activity of one or more polypeptides listed in Table 1 in the tissue of the subject.

In another aspect, the invention relates to methods of treating disorders relating to excessive or undesired angiogenesis in a subject, comprising decreasing the expression and/or activity of one or more polypeptides listed in Table 1 in the subject.

In another aspect, the invention relates to methods of treating or preventing cancer in a subject, comprising decreasing the expression and/or activity of one or more polypeptides listed in Table 1 in the subject.

The invention further relates to methods of treating or preventing metastases in a subject, comprising decreasing the expression and/or activity of one or more polypeptides listed in Table 1 in the subject.

In an additional aspect, the invention relates to methods of reducing tumorigenicity in a subject, comprising decreasing the expression and/or activity of one or more polypeptides listed in Table 1 in said subject.

In an additional aspect, the invention relates to methods of inhibiting angiogenesis in a tissue of a subject, methods of treating disorders relating to excessive or undesired angiogenesis in a subject, methods of treating or preventing cancer in a subject, methods of treating or preventing metastases in a subject, and/or methods of reducing tumorigenicity in a subject, comprising delivering to the subject a calcineurin or NF-ATc inhibitor, e.g., tacrolimus.

In each of these aspects, the subject may be diagnosed with cancer, e.g., breast cancer. In certain embodiments, the expression and/or activity of the one or more polypeptides is decreased by decreasing the level of a nucleic acid encoding the polypeptide (e.g., with antisense RNA, microRNA, or siRNA), decreasing the level of the polypeptide itself, or decreasing the activity of the polypeptide (e.g., with an antibody, aptamer, or small molecule that specifically inhibits the polypeptide itself or a signaling pathway upstream or downstream of the polypeptide). In one embodiment, the one or more polypeptides is selected from the group consisting of SFRP2, JAK3, and FAP or combinations thereof. In another embodiment, the one or more polypeptides does not include SFRP2. In another embodiment, the one or more polypeptides does not include JAK3. In another embodiment, the one or more polypeptides does not include FAP.

A further aspect of the invention relates to methods of increasing angiogenesis in a cell, comprising increasing the expression and/or activity of one or more polypeptides listed in Table 1 in the cell. In certain embodiments, the expression and/or activity of one or more polypeptides listed in Table 1 is increased by delivering a nucleic acid encoding the polypeptide or the polypeptide itself to the cell.

Another aspect of the invention relates to methods of increasing angiogenesis in a tissue of a subject, comprising increasing the expression and/or activity of one or more polypeptides listed in Table 1 in the tissue of the subject. In certain embodiments, the expression and/or activity of one or more polypeptides listed in Table 1 is increased by delivering a nucleic acid encoding the polypeptide or the polypeptide itself to the subject.

The invention further relates to methods of diagnosing cancer in a subject, comprising obtaining a sample (e.g., a tissue sample or cells) from the subject and determining the expression and/or activity of one or more polypeptides listed in Table 1 in the sample, wherein an increase in expression and/or activity relative to the level of expression and/or activity in a control sample is indicative of cancer. In one embodiment, the expression and/or activity of at least 2, 5, 10, or more of the listed polypeptides is determined. In certain embodiments, the expression may be determined by determining the level of nucleic acid encoding the polypeptide or the polypeptide itself.

An additional aspect of the invention relates to methods of determining the angiogenesis potential of a cancer in a subject, comprising obtaining a sample (e.g., a tissue sample or cells) from the cancer of the subject and determining the expression and/or activity of one or more polypeptides listed in Table 1 in the sample, wherein an increase in expression and/or activity relative to the level of expression and/or activity in a control sample is indicative of an increased angiogenesis potential of the cancer.

The invention also relates to methods of determining the metastatic potential of a cancer in a subject, comprising obtaining a sample (e.g., a tissue sample or cells) from the cancer of the subject and determining the expression and/or activity of one or more polypeptides listed in Table 1 in the sample, wherein an increase in expression and/or activity relative to the level of expression and/or activity in a control sample is indicative of an increased metastatic potential of the cancer.

Another aspect of the invention relates to methods of monitoring the effectiveness of a treatment for cancer in a subject, comprising obtaining a sample (e.g., a tissue sample or cells) from a subject that has received treatment for cancer, determining the expression and/or activity of one or more polypeptides listed in Table 1 in the sample, and comparing the level of expression and/or activity to the level of expression and/or activity in a control sample, wherein a decrease in the level of expression and/or activity in the sample relative to the control sample is indicative of the effectiveness of the treatment.

The invention further relates to methods of monitoring the progression of cancer in a subject, comprising obtaining a sample (e.g., a tissue sample or cells) from a subject that has cancer, determining the expression and/or activity of one or more polypeptides listed in Table 1 in the sample, and comparing the level of expression and/or activity to the level of expression and/or activity in a control sample, wherein an increase in the level of expression and/or activity in the sample relative to the control sample is indicative of progression of the cancer.

The invention also relates to methods of distinguishing among breast cancer subtypes, comprising obtaining a breast cancer sample from a subject, determining the expression and/or activity of one or more polypeptides listed in Table 1 in the sample, and determining the subtype of cancer based on the pattern of expression and/or activity. In one embodiment, the method is used to distinguish between ER negative and ER positive breast cancers. In another embodiment, the method is used to distinguish between basal, Her2/neu, and luminal subtypes.

The invention further relates to methods of distinguishing between in situ and invasive breast cancers, comprising obtaining a breast cancer sample from a subject, determining the expression and/or activity of one or more polypeptides listed in Table 1 in the sample, and determining the type of cancer based on the pattern of expression and/or activity.

Additionally, the invention relates to methods of identifying a compound that regulates angiogenesis, comprising determining the expression and/or activity of one or more polypeptides listed in Table 1 in a cell-based assay or a non-cell-based assay in the presence and absence of a test compound, and selecting a compound that increases or decreases the level of expression and/or activity of the one or more polypeptides relative to the level in the absence of the compound, as a compound that regulates angiogenesis.

Another aspect of the invention relates to methods of identifying a compound useful for inhibition of tumor growth or metastasis, comprising determining the expression and/or activity of one or more polypeptides listed in Table 1 in a cell-based assay or a non-cell-based assay in the presence and absence of a test compound, and selecting a compound that increases or decreases the level of expression and/or activity of the one or more polypeptides relative to the level in the absence of the compound, as a compound useful for inhibition of tumor growth or metastasis.

The invention also relates to nucleic acid (e.g., oligonucleotide) or polypeptide (e.g., antibody) arrays comprising nucleic acids encoding at least two polypeptides listed in Table 1, e.g., at least 5, 10, 15, 20, or more polypeptides.

The invention further relates to molecules that increase or decrease the expression and/or activity of a polypeptide listed in Table 1 or a nucleic acid encoding the polypeptide. The molecules may be, for examples, antisense RNA, siRNA, aptamers, antibodies, small molecules, and the like. In one embodiment, the invention relates to pharmaceutical compositions comprising the molecules.

In another aspect, the invention relates to kits for assessing angiogenesis, comprising a reagent for determining the expression and/or activity of one or more polypeptides listed in Table 1.

In a further aspect, the invention relates to kits for diagnosing cancer, comprising a reagent for determining the expression and/or activity of one or more polypeptides listed in Table 1.

In another aspect, the invention relates to kits for determining the metastatic potential of a cancer, comprising a reagent for determining the expression and/or activity of one or more polypeptides listed in Table 1.

These and other aspects of the invention are set forth in more detail in the description of the invention below.

BRIEF DESCRIPTION OF THE DRAWINGS

FIG. 7 shows that SFRP2 increases endothelial cell migration in a wound scratch assay.

FIG. 8 shows that SFRP2 induces endothelial tube formation at 8 hours in a concentration-dependent manner.

FIG. 13 shows Western blot analyses of nuclear fractions of MEC cells treated with and without SFRP2 (700 µM) for 1 hour.

FIG. 16 shows that SFRP2 is increased in the SVR angiosarcoma cell line compared to control mouse endothelial cells.

FIGS. 17A-17D show A) SFRP2 induces tube formation in MEC cells; B) tacrolimus inhibits tube formation in SFRP2-induced MEC cells; C) tacrolimus inhibits tube formation in SVR angiosarcoma cells; and D) SVR tube formation is inhibited by a polyclonal antibody to SFRP2.

FIG. 22 shows the inhibitory activity of polyclonal antibodies raised against different epitopes of SFRP2. Sera from mice immunized against peptide sequences from SFRP2 (AbA, AbB, AbC, AbD, AbE) and control sera were used at 1:100 dilution. Antibodies to peptide AbA, AbB, AbC, and AbD all inhibited tube formation, however AbB and AbC had the greatest inhibition. N=4 for all groups.

FIG. 25 shows that SFRP2 protein is present in the endothelium in a wide variety of tumor types by immunohistochemistry. Paraffin-embedded sections of human tumors were stained with an antibody to SFRP2. Pictures are taken at 600× magnification.

DETAILED DESCRIPTION OF THE INVENTION

Figure 1:
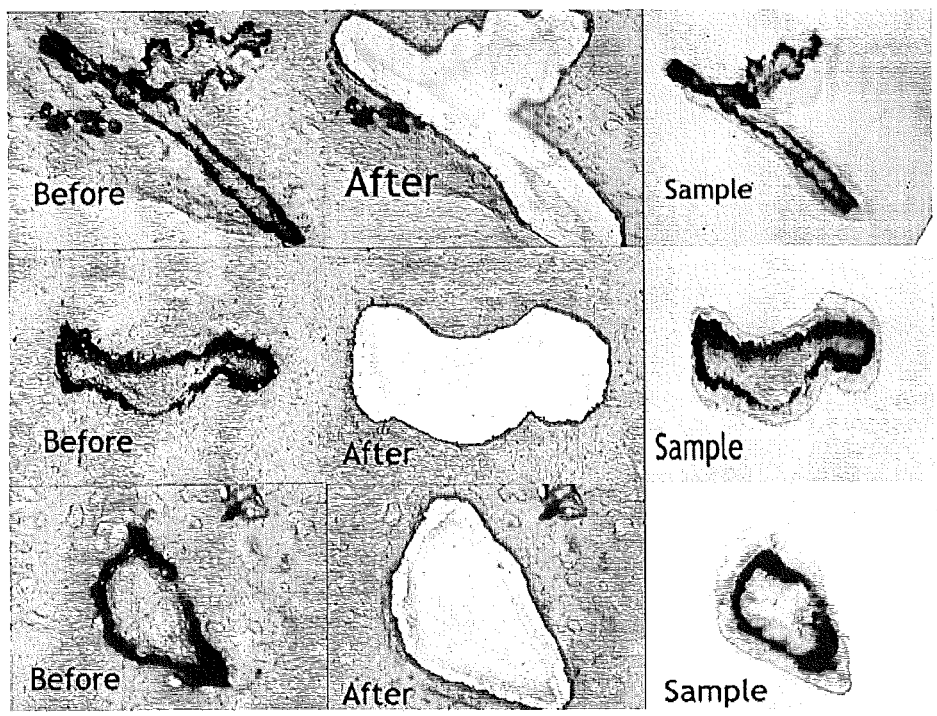
FIG. 1 shows laser capture microdissection of human breast vascular cells before and after microdissection (400×).

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. *Current Protocols in Molecular Biology* (Green Publishing Associates, Inc. and John Wiley & Sons, Inc., New York).

I. Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in angiogenesis-stimulating activity of at least about 50% or more as compared to the activity of a polypeptide consisting of the recited sequence.

The term "regulate," "regulates," or "regulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject (e.g., in the case of cancer, reduction in tumor burden, prevention of further tumor growth, prevention of metastasis, or increase in survival time). Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

The phrase "tumorigenicity" refers primarily to the tumor status of a cell or cells (e.g., the extent of neoplastic transformation of a cell, the malignancy of a cell, the propensity for a cell to form a tumor and/or have characteristics of a tumor, or simply the presence or absence of tumor cells in a patient or tissue/organ), which is reflective of a change of a cell or population of cells from a normal to malignant state. Tumorigenicity indicates that tumor cells are present in a sample, and/or that the transformation of cells from normal to tumor cells is in progress, as may be confirmed by any standard of measurement of tumor development. The change typically involves cellular proliferation at a rate which is more rapid than the growth observed for normal cells under the same conditions, and which is typically characterized by one or more of the following traits: continued growth even after the instigating factor (e.g., carcinogen, virus) is no longer present; a lack of structural organization and/or coordination with normal tissue, and typically, a formation of a mass of tissue, or tumor. A tumor, therefore, is most generally described as a proliferation of cells (e.g., a neoplasia, a growth, a polyp) resulting from neoplastic growth and is most typically a malignant tumor. In the case of a neoplastic transformation, a neoplasia is malignant or is predisposed to become malignant. Malignant tumors are typically characterized as being anaplastic (primitive cellular growth characterized by a lack of differentiation), invasive (moves into and destroys surrounding tissues) and/or metastatic (spreads to other parts of the body).

The phrase "disorder related to excessive or undesired angiogenesis," as used herein, refers to any disease, disorder, or condition in which unwanted angiogenesis occurs. Examples of such disorders include, without limitation, cancer, infectious diseases, autoimmune disorders, vascular malformations, DiGeorge syndrome, HHT, cavernous hemangioma, atherosclerosis, transplant arteriopathy, obesity, psoriasis, warts, allergic dermatitis, scar keloids, pyogenic granulomas, blistering disease, Kaposi's sarcoma, persistent hyperplastic vitreous syndrome, diabetic retinopathy, retinopathy of prematurity, macular degeneration, choroidal neovascularization, primary pulmonary hypertension, asthma, nasal polyps, inflammatory bowel disease, periodontal disease, ascites, peritoneal adhesions, endometriosis, uterine bleeding, ovarian cysts, ovarian hyperstimulation, ectopic pregnancy, arthritis, synovitis, osteomyelitis, and/or osteophyte formation.

The term "cancer," as used herein, refers to any benign or malignant abnormal growth of cells. Examples include, without limitation, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers.

The term "breast cancer," as used herein, refers to a cancer that starts in the cells of the breast of a subject. The term includes invasive and in situ cancers, and encompasses all subtypes of breast cancer, including basal subtype (ER negative and Her2/neu negative), Her2/neu subtype (Her2/neu positive and ER negative); and luminal subtype (ER positive).

The term "control sample," as used herein, refers to a tissue or cell sample that is used to compare the level of expression and/or activity of one or more polypeptides listed in Table 1 to the level of expression and/or activity in a sample of interest. The control sample may be, for example, from a normal (i.e., non-diseased) portion of the same tissue or cell type in the subject, from a different tissue or cell type in the subject, from a matched individual, or may be a standard derived from the average of measurements taken from a population of subjects. In another embodiment, the control sample may be from the disease tissue of the subject, e.g., at the time of diagnosis, prior to treatment, or after a stage of treatment.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An isolated cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art; e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Chem.* 263:14621 (1988); and Hartmut et al., *Canadian Patent Application No.* 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Feigner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et at, 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., angiogenic activity, protein binding, ligand or receptor binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and angiogenic activity can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

II. Polynucleotides and Polypeptides Upregulated in Tumor Blood Vessel Cells

The inventors have identified and characterized polypeptides, and polynucleotides encoding the polypeptides, which are significantly upregulated in tumor blood vessel cells as compared to non-tumor blood vessels. Table 1 lists 55 polynucleotides that are upregulated at least four-fold in cells associated with breast tumor blood vessels. Each of these upregulated polynucleotides and polypeptides represents a useful target for the study of angiogenesis, tumor formation, growth and metastasis. Further, these targets are useful for the diagnosis and treatment of diseases and disorders related to angiogenesis, e.g., cancer, ischemia, etc. Additionally, these targets can be used to screen for agents that can be used to diagnose and treat angiogenesis-related diseases and disorders. All information associated with the publically available identifiers and accession numbers in Table 1, including the nucleic acid sequences of the genes and the amino acid sequences of the polypeptides encoded thereby, is hereby incorporated by reference in its entirety.

TABLE 1

Upregulated Genes in Tumor Vessel Cells with Greater than Four Fold Change

| Gene Symbol | GenBank Accession No. | Gene Name | Fold Change |
| --- | --- | --- | --- |
| NAT1 | NM_000662 | N-acetyltransferase 1 (arylamine N-acetyltransferase) | 17.6 |
| DHRS2 | NM_005794 | Dehydrogenase/reductase (SDR family) member 2 | 11.9 |
| IFI27 | NM_005532 | Interferon, alpha-inducible protein 27 | 11.7 |
| S100A8 | NM_002964 | S100A8 S100 calcium binding protein A8 (calgranulin A) | 11.7 |
| MTL5 | NM_004923 | MTL5 Metallothionein-like 5, testis-specific (tesmin) | 10.9 |
| FAP | NM_004460 | FAP Fibroblast activation protein, alpha | 10.7 |
| IFI27 | NM_005532 | Interferon, alpha-inducible protein 27 | 10.1 |
| UNG2 | NM_021147 | Uracil-DNA glycosylase 2 | 9.0 |
| | | THC1546313 | 8.9 |
| APXL2 | AB075840 | Apical protein 2 | 8.8 |
| MGC16121 | NM_032762 | Hypothetical protein MGC16121 | 8.7 |
| MMP1 | NM_002421 | Matrix metalloproteinase 1 (interstitial collagenase) | 8.1 |
| MMP11 | NM_005940 | Matrix metalloproteinase 11 (stromelysin 3) | 8.1 |
| SULF1 | NM_015170 | Sulfatase 1 | 7.9 |
| SLITRK6 | NM_032229 | SLIT and NTRK-like family, member 6 | 7.6 |
| LTB | NM_002341 | Lymphotoxin beta (TNF superfamily, member 3) | 7.3 |
| INHBA | NM_002192 | Inhibin, beta A (activin A, activin AB alpha polypeptide) | 7.2 |
| | | THC1598071 | 6.6 |
| PREX1 | NM_020820 | Phosphatidylinositol 3,4,5-trisphosphate-dependent RAC exchanger 1 | 6.4 |
| CHST8 | NM_022467 | Carbohydrate (N-acetylgalactosamine 4-0) sulfotransferase 8 | 6.4 |
| SFRP2 | AF311912 | Secreted frizzled-related protein 2 | 6.3 |
| SMPD3 | NM_024703 | Sphingomyelin phosphodiesterase 3, neutral membrane | 6.3 |
| KAZALD1 | AF333487 | Kazal-type serine peptidase inhibitor domain 1 | 6.2 |
| FGFR3 | NM_000142 | Fibroblast growth factor receptor 3 | 6.2 |
| SPOCD1 | NM_144569 | SPOC domain containing 1 | 6.1 |
| IRF7 | NM_004030 | Interferon regulatory factor 7 | 5.9 |
| COL1A2 | NM_000089 | Collagen, type I, alpha 2 | 5.8 |
| CD19 | NM_001770 | CD19 antigen | 5.7 |
| BF | NM_001710 | B-factor, properdin | 5.6 |
| SQLE | NM_003129 | Squalene epoxidase | 5.6 |
| HOXB6 | NM_156036 | Homeo box B6 | 5.6 |

TABLE 1-continued

Upregulated Genes in Tumor Vessel Cells with Greater than Four Fold Change

| Gene Symbol | GenBank Accession No. | Gene Name | Fold Change |
|---|---|---|---|
| MLPH | NM_024101 | Melanophilin | 5.2 |
| DKFZp434E2321 | NM_207310 | Hypothetical protein DKFZp434E2321 | 5.2 |
| HTRA3 | NM_053044 | HtrA serine peptidase 3 | 5.1 |
| T3JAM | NM_025228 | TRAF3-interacting Jun N-terminal kinase (JNK)-activating modulator | 4.9 |
| ASCL2 | NM_005170 | Achaete-scute complex-like 2 (*Drosophila*) | 4.9 |
| | | I_960623 | 4.7 |
| HSPB1 | NM_001540 | Heat shock 27 kDa protein 1 | 4.6 |
| COL12A1 | NM_004370 | Collagen, type XII, alpha 1 | 4.6 |
| HOXB2 | NM_002145 | Homeo box B2 | 4.6 |
| HIG2 | NM_013332 | Hypoxia-inducible protein 2 | 4.6 |
| FLJ00332 | BC036873 | FLJ00332 protein | 4.6 |
| JAK3 | BC028068 | Janus kinase 3 (a protein tyrosine kinase, leukocyte) | 4.5 |
| S100P | NM_005980 | S100 calcium binding protein P | 4.5 |
| RAMP1 | NM_005855 | Receptor (calcitonin) activity modifying protein 1 | 4.4 |
| COL5A1 | NM_000093 | Collagen, type V, alpha 1 | 4.4 |
| CENPF | NM_016343 | Centromere protein F, 350/400 ka (mitosin) | 4.3 |
| DOK3 | BC004867 | Docking protein 3 | 4.2 |
| | AA516420 | AA516420 | 4.2 |
| NID2 | NM_007361 | Nidogen 2 (osteonidogen) | 4.2 |
| | | I_1000437 | 4.1 |
| FGD3 | NM_033086 | FGD1 family, member 3 | 4.1 |
| | AK098833 | Hypothetical gene supported by AK098833 | 4.1 |
| AEBP1 | NM_001129 | AE binding protein 1 | 4.0 |
| | | A_23_BS21882 | 4.0 |

III. Inhibition of Angiogenesis

Accordingly, as one aspect, the invention provides methods of inhibiting angiogenesis in a cell, comprising decreasing the expression and/or activity of one or more polypeptides listed in Table 1 in the cell.

In a further aspect, the invention provides methods of inhibiting angiogenesis in a tissue of a subject, comprising decreasing the expression and/or activity of one or more polypeptides listed in Table 1 in the tissue of the subject.

In another aspect, the invention relates to methods of treating or preventing cancer in a subject, comprising decreasing the expression and/or activity of one or more polypeptides listed in Table 1 in the subject.

The invention further relates to methods of treating or preventing metastases in a subject, comprising decreasing the expression and/or activity of one or more polypeptides listed in Table 1 in the subject.

In an additional aspect, the invention relates to methods of reducing tumorigenicity in a subject, comprising decreasing the expression and/or activity of one or more polypeptides listed in Table 1 in the subject.

The invention further relates to methods of regulating fertility in a female subject (e.g., preventing conception or terminating a pregnancy), comprising decreasing the expression and/or activity of one or more polypeptides listed in Table 1 in the subject (see U.S. Pat. No. 6,017,949).

In one embodiment of each of these aspects, the subject may be one that has been diagnosed with cancer, e.g., breast cancer. In another embodiment, the subject may be one that is at risk of developing cancer (e.g., predisposed due to hereditary factors, smoking, viral infection, exposure to chemicals, etc.). In another embodiment, the subject may be one that has been diagnosed with another disease or disorder associated with excessive or abnormal angiogenesis, e.g., infectious diseases, autoimmune disorders, vascular malformations, DiGeorge syndrome, HHT, cavernous hemangioma, atherosclerosis, transplant arteriopathy, obesity, psoriasis, warts, allergic dermatitis, scar keloids, pyogenic granulomas, blistering disease, Kaposi's sarcoma, persistent hyperplastic vitreous syndrome, diabetic retinopathy, retinopathy of prematurity, choroidal neovascularization, primary pulmonary hypertension, asthma, nasal polyps, inflammatory bowel disease, periodontal disease, ascites, peritoneal adhesions, endometriosis, uterine bleeding, ovarian cysts, ovarian hyperstimulation, arthritis, synovitis, osteomyelitis, and/or osteophyte formation.

In one embodiment, the expression and/or activity of 2, 3, 4, 5, or more of the polypeptides listed in Table 1 may be decreased. Any single polypeptide or combination of polypeptides on the list may be inhibited. It is further contemplated that any one or more polypeptide listed in Table 1 may be excluded from the methods, e.g., the method may be practiced with any listed polypeptide except SFRP2. In one embodiment, the polypeptides are selected from the group consisting of SFRP2, JAK3, and FAP, or any combination thereof. In another embodiment, the one or more polypeptides does not include SFRP2. In another embodiment, the one or more polypeptides does not include JAK3. In another embodiment, the one or more polypeptides does not include FAP.

In one embodiment of the invention, decreasing the expression and/or activity of one or more polypeptides listed in Table 1 comprises decreasing the level of a nucleic acid (DNA or RNA) encoding the polypeptide or the level of expression of the polypeptide from the nucleic acid. Numerous methods for reducing the level and/or expression of polynucleotides in vitro or in vivo are known. For example, the coding and noncoding nucleotide sequences for the polypeptides listed in Table 1 are known to those of skill in the art and are readily available in sequence databases such as GenBank. An antisense nucleotide sequence or nucleic acid encoding an antisense nucleotide sequence can be generated to any portion thereof in accordance with known techniques.

The term "antisense nucleotide sequence" or "antisense oligonucleotide" as used herein, refers to a nucleotide sequence that is complementary to a specified DNA or RNA sequence. Antisense oligonucleotides and nucleic acids that express the same can be made in accordance with conventional techniques. See, e.g., U.S. Pat. No. 5,023,243 to Tullis; U.S. Pat. No. 5,149,797 to Pederson et al. The antisense nucleotide sequence can be complementary to the entire nucleotide sequence encoding the polypeptide or a portion thereof of at least 10, 20, 40, 50, 75, 100, 150, 200, 300, or 500 contiguous bases and will reduce the level of polypeptide production.

Those skilled in the art will appreciate that it is not necessary that the antisense nucleotide sequence be fully complementary to the target sequence as long as the degree of sequence similarity is sufficient for the antisense nucleotide sequence to hybridize to its target and reduce production of the polypeptide. As is known in the art, a higher degree of sequence similarity is generally required for short antisense nucleotide sequences, whereas a greater degree of mismatched bases will be tolerated by longer antisense nucleotide sequences.

For example, hybridization of such nucleotide sequences can be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and/or conditions represented by a wash stringency of 50% formamide with 5×Denhardt's solution, 0.5% SDS and 1×SSPE at 42° C., respectively) to the nucleotide sequences specifically disclosed herein. See, e.g., Sambrook et al., Molecular Cloning: A Laboratory Manual 2nd Ed. (Cold Spring Harbor, N.Y., 1989).

In other embodiments, antisense nucleotide sequences of the invention have at least about 70%, 80%, 90%, 95%, 97%, 98% or higher sequence similarity with the complement of the coding sequences specifically disclosed herein and will reduce the level of polypeptide production.

In other embodiments, the antisense nucleotide sequence can be directed against any coding sequence, the silencing of which results in a modulation of a polypeptide listed in Table 1.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length up to about 20, 30, 50, 75 or 100 nucleotides, or longer, in length.

An antisense nucleotide sequence can be constructed using chemical synthesis and enzymatic ligation reactions by procedures known in the art. For example, an antisense nucleotide sequence can be chemically synthesized using naturally occurring nucleotides or various modified nucleotides designed to increase the biological stability of the molecules or to increase the physical stability of the duplex formed between the antisense and sense nucleotide sequences, e.g., phosphorothioate derivatives and acridine substituted nucleotides can be used. Examples of modified nucleotides which can be used to generate the antisense nucleotide sequence include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleotide sequence can be produced using an expression vector into which a nucleic acid has been cloned in an antisense orientation (i.e., RNA transcribed from the inserted nucleic acid will be of an antisense orientation to a target nucleic acid of interest).

The antisense nucleotide sequences of the invention further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the antisense nucleotide sequence is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989); Agrawal et al., *Proc. Natl. Acad. Res. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988); incorporated by reference herein in their entireties for their teaching of methods of making antisense molecules, including those containing modified nucleotide bases).

Triple helix base-pairing methods can also be employed to inhibit production of polypeptides listed in Table 1. Triple helix pairing is believed to work by inhibiting the ability of the double helix to open sufficiently for the binding of polymerases, transcription factors, or regulatory molecules. Recent therapeutic advances using triplex DNA have been described in the literature (e.g., Gee et al., (1994) In: Huber et al., Molecular and Immunologic Approaches, Futura Publishing Co., Mt. Kisco, N.Y.).

Small Interference (si) RNA, also known as RNA interference (RNAi) molecules, provides another approach for modulating the expression of polypeptides listed in Table 1. The siRNA can be directed against polynucleotide sequences encoding the listed polypeptides or any other sequence that results in modulation of the expression of the listed polypeptides.

siRNA is a mechanism of post-transcriptional gene silencing in which double-stranded RNA (dsRNA) corresponding to a coding sequence of interest is introduced into a cell or an organism, resulting in degradation of the corresponding mRNA. The mechanism by which siRNA achieves gene silencing has been reviewed in Sharp et al., *Genes Dev.* 15:485 (2001); and Hammond et al., *Nature Rev. Gen.* 2:110 (2001)). The siRNA effect persists for multiple cell divisions before gene expression is regained. siRNA is therefore a powerful method for making targeted knockouts or "knockdowns" at the RNA level. siRNA has proven successful in human cells, including human embryonic kidney and HeLa cells (see, e.g., Elbashir et al., *Nature* 411:494 (2001)). In one embodiment, silencing can be induced in mammalian cells by enforcing endogenous expression of RNA hairpins (see Paddison et al., *Proc. Natl. Acad. Sci. USA* 99:1443 (2002)). In another embodiment, transfection of small (21-23 nt) dsRNA specifically inhibits nucleic acid expression (reviewed in Caplen, *Trends Biotechnol.* 20:49 (2002)).

siRNA technology utilizes standard molecular biology methods. dsRNA corresponding to all or a part of a target coding sequence to be inactivated can be produced by standard methods, e.g., by simultaneous transcription of both strands of a template DNA (corresponding to the target sequence) with T7 RNA polymerase. Kits for production of dsRNA for use in siRNA are available commercially, e.g., from New England Biolabs, Inc. Methods of transfection of dsRNA or plasmids engineered to make dsRNA are routine in the art.

MicroRNA (miRNA), single stranded RNA molecules of about 21-23 nucleotides in length, can be used in a similar fashion to siRNA to modulate gene expression (see U.S. Pat. No. 7,217,807).

Silencing effects similar to those produced by siRNA have been reported in mammalian cells with transfection of a mRNA-cDNA hybrid construct (Lin et al., *Biochem. Biophys. Res. Commun.* 281:639 (2001)), providing yet another strategy for silencing a coding sequence of interest.

The expression of polypeptides listed in Table 1 can also be inhibited using ribozymes. Ribozymes are RNA-protein complexes that cleave nucleic acids in a site-specific fashion. Ribozymes have specific catalytic domains that possess endonuclease activity (Kim et al., *Proc. Natl. Acad. Sci. USA* 84:8788 (1987); Gerlach et al., *Nature* 328:802 (1987); Forster and Symons, *Cell* 49:211 (1987)). For example, a large number of ribozymes accelerate phosphoester transfer reactions with a high degree of specificity, often cleaving only one of several phosphoesters in an oligonucleotide substrate (Michel and Westhof, *J. Mol. Biol.* 216:585 (1990); Reinhold-Hurek and Shub, *Nature* 357:173 (1992)). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, *Nature* 338:217 (1989)). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., *Proc. Natl. Acad. Sci. USA* 88:10591 (1991); Sarver et al., *Science* 247:1222 (1990); Sioud et al., *J. Mol. Biol.* 223:831 (1992)).

In another embodiment of the invention, decreasing the expression and/or activity of one or more polypeptides listed in Table 1 comprises decreasing the activity of said polypeptide. Polypeptide activity can be modulated by interaction with an antibody or antibody fragment. The antibody or antibody fragment can bind to the polypeptide or to any other polypeptide of interest, as long as the binding between the antibody or the antibody fragment and the target polypeptide results in modulation of the activity of the listed polypeptide.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric antibody. See, e.g., Walker et al., *Molec. Immunol.* 26:403 (1989). The antibodies can be recombinant monoclonal antibodies produced according to the methods disclosed in U.S. Pat. Nos. 4,474,893 or 4,816,567. The antibodies can also be chemically constructed according to the method disclosed in U.S. Pat. No. 4,676,980.

Antibody fragments included within the scope of the present invention include, for example, Fab, Fab', F(ab')$_2$, and Fv fragments; domain antibodies, diabodies; vaccibodies, linear antibodies; single-chain antibody molecules; and multispecific antibodies formed from antibody fragments. Such fragments can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254:1275 (1989)).

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); Riechmann et al., *Nature*, 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol* 14:845 (1996); Neuberger, *Nature Biotechnol.* 14:826 (1996); Lonberg and Huszar, *Intern. Rev. Immunol.* 13:65 (1995).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies used to carry out the present invention can be produced in a hybridoma cell line according to the technique of Kohler and Milstein, *Nature* 265:495 (1975). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, *Science* 246:1275 (1989).

Antibodies specific to the target polypeptide can also be obtained by phage display techniques known in the art.

Various immunoassays can be used for screening to identify antibodies having the desired specificity for the polypeptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}$S, $^{125}$I, $^{131}$I), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In one embodiment, the antibody is an antibody or a fragment thereof (e.g., a monoclonal antibody) that specifically binds to SFRP2. The antibody may bind to a specific epitope on SFRP2, e.g., the WNT binding domain (about amino acids 30-160) or the NTR domain (about amino acids 169-295), that causes inhibition of SFRP2 activity. Suitable epitopes for raising antibodies include, but are not limited to, sequences comprising, consisting essentially of, or consisting of amino acids 29-40 of human SFRP2 (GQPDFSYRSNC (SEQ ID NO:1)), 85-96 (KQCHPDTKKELC (SEQ ID NO:2)), 119-125 (VQVKDRC (SEQ ID NO:3)) 138-152 (DMLECDRFPQDNDLC (SEQ ID NO:4)), 173-190 (EACKNKNDDDNDIMETLC (SEQ ID NO:5)), 202-220 (EITYINRDTKIILETKSKT-Cys (SEQ ID NO:6)), or 270-295 (ITSVKRWQKGQREFKRISRSIRKLQC (SEQ ID NO:7)) or a fragment thereof of three or more amino acids (e.g., 3, 4, 5, 6, 7, 8, 9, or 10 or more). In one embodiment, the epitope is amino acids 202-220 (EITYINRDTKIILETKSKT-Cys (SEQ ID NO:6)) or a fragment thereof. In another embodiment, the epitope is a fragment of the protein from about amino acid 156 to about amino acid 295. The amino acid numbering is based on the GenBank listing for human SFRP2 (accession number AAH08666), herein incorporated by reference.

In one embodiment, the antibody is a monoclonal antibody produced by hybridoma cell line UNC 68-80 (subclone 80.8.6) (ATCC Deposit No. PTA-11762). In a further embodiment, the antibody is a monoclonal antibody or a fragment thereof that competes for binding to the same epitope specifically bound by the monoclonal antibody produced by hybridoma cell line UNC 68-80 (ATCC Deposit No. PTA-11762). In another embodiment, the antibody is a monoclonal antibody or a fragment thereof that specifically binds to the same epitope specifically bound by the monoclonal antibody produced by hybridoma cell line UNC 68-80 (ATCC Deposit No. PTA-11762). In certain embodiments, the monoclonal antibody or a fragment thereof is a chimeric antibody or a humanized antibody. In additional embodiments, the chimeric or humanized antibody comprises at least a portion of the CDRs of the monoclonal antibody produced by hybridoma cell line UNC 68-80 (ATCC Deposit No. PTA-11762). As used herein, a "portion" of a CDR is defined as one or more of the three loops from each of the light and heavy chain that make up the CDRs (e.g., from 1-6 of the CDRs) or one or more portions of a loop comprising, consisting essentially of, or consisting of at least three contiguous amino acids. For example, the chimeric or humanized antibody may comprise 1, 2, 3, 4, 5, or 6 CDR loops, portions of 1, 2, 3, 4, 5, or 6 CDR loops, or a mixture thereof.

In one embodiment, the antibody or a fragment thereof comprises a heavy chain variable region comprising the amino acid sequence of SEQ ID NO:13 or a sequence at least 90% identical thereto, e.g., at least 95, 96, 97, 98, or 99% identical thereto. In another embodiment, the antibody or a fragment thereof comprises a heavy chain variable region comprising an amino acid sequence encoded by the nucleotide sequence of SEQ ID NO:14 or a sequence at least 90% identical thereto, e.g., at least 95, 96, 97, 98, or 99% identical thereto.

(SEQ ID NO: 13)
QVQLQQPGAELVQPGASVMLSCKASGFTFTRYWWHWVRQTPGRGLEWIG

RIDPNSGTTRFIEKFKTKATLTVDKPSSTAYMHLSSLTSEDSAVYYCAR

WGPYYGYAMDYWGPGTSVTVSS (SEQ ID NO: 14)
CAGGTCCAATTGCAGCAGCCTGGGGCTGAGCTTGTGCAGCCTGGGGCTT

CAGTGATGCTGTCCTGCAAGGCTTCTGGTTTCACCTTCACCAGGTATTG

GTGGCACTGGGTGAGGCAGACGCCTGGACGAGGCCTTGAGTGGATTGGA

AGGATTGATCCTAATAGTGGTACTACTAGGTTCATTGAGAAGTTCAAGA

CCAAGGCCACACTGACTGTAGACAAACCCTCCAGCACAGCCTACATGCA

CCTCAGCAGTCTCACATCTGAAGACTCTGCGGTCTATTATTGTGCAAGA

TGGGGGCCCTACTACGGCTATGCTATGGACTACTGGGGTCCAGGAACCT

CAGTCACCGTCTCCTCA

In one embodiment, the antibody or a fragment thereof comprises a light chain variable region comprising the amino acid sequence of SEQ ID NO:15 or a sequence at least 90% identical thereto, e.g., at least 95, 96, 97, 98, or 99% identical thereto. In another embodiment, the antibody or a fragment thereof comprises a light chain variable region comprising an amino acid sequence encoded by the nucleotide sequence of SEQ ID NO:16 or a sequence at least 90% identical thereto, e.g., at least 95, 96, 97, 98, or 99% identical thereto.

(SEQ ID NO: 15)
QIVLTQSPAIMSASPGQKVTITCSASSSVTYMHWYQQKLGSSPKLWIYD

TSRLAPGSPARFSGSGSGTSYSLTISSMETEDAASYFCHQWSTYPPTFG

TGTKLEIQ (SEQ ID NO: 16)
CAAATTGTTCTCACCCAGTCTCCAGCAATCATGTCTGCATCTCCAGGGC

AGAAAGTCACCATAACCTGCAGTGCCAGTTCAAGTGTTACTTACATGCA

CTGGTATCAGCAGAAGTTAGGATCCTCCCCCAAACTCTGGATTTATGAC

ACATCCAGACTGGCTCCTGGATCCCCTGCTCGCTTCAGTGGCAGTGGGT

CTGGAACCTCTTACTCTCTCACAATCAGCAGCATGGAGACTGAAGATGC

TGCCTCTTATTTCTGCCATCAGTGGAGTACTTACCCGCCCACGTTCGGC

ACGGGGACAAAATTGGAAATACAA

In one embodiment, the antibody or a fragment thereof comprises a heavy chain variable region comprising the amino acid sequence of SEQ ID NO:13 or a sequence at least 90% identical thereto, e.g., at least 95, 96, 97, 98, or 99% identical thereto, or encoded by the nucleotide sequence of SEQ ID NO:14 or a sequence at least 90% identical thereto, e.g., at least 95, 96, 97, 98, or 99% identical thereto, and a light chain variable region comprising the amino acid sequence of SEQ ID NO:15 or a sequence at least 90% identical thereto, e.g., at least 95, 96, 97, 98, or 99% identical thereto, or encoded by the nucleotide sequence of SEQ ID NO:16 or a sequence at least 90% identical thereto, e.g., at least 95, 96, 97, 98, or 99% identical thereto.

In one embodiment, the antibody or a fragment thereof comprises a heavy chain variable region comprising at least one CDR (e.g., 1, 2, or 3) or a portion thereof from the amino acid sequence of SEQ ID NO:13 or a sequence at least 90% identical thereto, e.g., at least 95, 96, 97, 98, or 99% identical thereto. In another embodiment, the antibody or a fragment thereof comprises a heavy chain variable region comprising at least one CDR (e.g., 1, 2, or 3) or a portion thereof from an amino acid sequence encoded by the nucleotide sequence of SEQ ID NO:14 or a sequence at least 90% identical thereto, e.g., at least 95, 96, 97, 98, or 99% identical thereto. One of skill in the art understands that the CDRs play an important role in binding specificity and that sequence substitutions (e.g., for humanization of a mouse antibody) are preferably made outside of the CDRs and that minimal changes are made within the CDRs. Thus, in some embodiments, sequences that are at least 90% identical to the disclosed sequences comprise no changes or only a minimal number of changes to the CDRs.

In one embodiment, the antibody or a fragment thereof comprises a light chain variable region comprising at least one CDR (e.g., 1, 2, or 3) or a portion thereof from the amino acid sequence of SEQ ID NO:15 or a sequence at least 90% identical thereto, e.g., at least 95, 96, 97, 98, or 99% identical thereto. In another embodiment, the antibody or a fragment thereof comprises a light chain variable region comprising at least one CDR (e.g., 1, 2, or 3) or a portion thereof from an amino acid sequence encoded by the nucleotide sequence of SEQ ID NO:16 or a sequence at least 90% identical thereto, e.g., at least 95, 96, 97, 98, or 99% identical thereto.

In one embodiment, the antibody or a fragment thereof comprises a heavy chain variable region comprising at least one CDR (e.g., 1, 2, or 3) from the amino acid sequence of SEQ ID NO:13 or a sequence at least 90% identical thereto, e.g., at least 95, 96, 97, 98, or 99% identical thereto, or encoded by the nucleotide sequence of SEQ ID NO:14 or a sequence at least 90% identical thereto, e.g., at least 95, 96, 97, 98, or 99% identical thereto, and a light chain variable region comprising at least one CDR (e.g., 1, 2, or 3) from the amino acid sequence of SEQ ID NO:15 or a sequence at least 90% identical thereto, e.g., at least 95, 96, 97, 98, or 99% identical thereto, or encoded by the nucleotide sequence of SEQ ID NO:16 or a sequence at least 90% identical thereto, e.g., at least 95, 96, 97, 98, or 99% identical thereto.

In one embodiment, the activity of the of one or more polypeptides listed in Table 1 is inhibited using aptamers. Recently, small structured single-stranded RNAs, also known as RNA aptamers, have emerged as viable alternatives to small-molecule and antibody-based therapy (Que-Gewirth et al., *Gene Ther.* 14:283 (2007); Ireson et al., *Mol. Cancer. Ther.* 5:2957 (2006)). RNA aptamers specifically bind target proteins with high affinity, are quite stable, lack immunogenicity, and elicit biological responses. Aptamers are evolved by means of an iterative selection method called SELEX (systematic evolution of ligands by exponential enrichment) to specifically recognize and tightly bind their targets by means of well-defined complementary three-dimensional structures.

RNA aptamers represent a unique emerging class of therapeutic agents (Que-Gewirth et al., *Gene Ther.* 14:283 (2007); Ireson et al., *Mol. Cancer. Ther.* 5:2957 (2006)). They are relatively short (12-30 nucleotide) single-stranded RNA oligonucleotides that assume a stable three-dimensional shape to tightly and specifically bind selected protein targets to elicit a biological response. In contrast to antisense oligonucleotides, RNA aptamers can effectively target extracellular targets. Like antibodies, aptamers possess binding affinities in the low nanomolar to picomolar range. In addition, aptamers are heat stable, lack immunogenicity, and possess minimal interbatch variability. Chemical modifications, such as amino or fluoro substitutions at the 2' position of pyrimidines, may reduce degradation by nucleases. The biodistribution and clearance of aptamers can also be altered by chemical addition of moieties such as polyethylene glycol and cholesterol. Further, SELEX allows selection from libraries consisting of up to $10^{15}$ ligands to generate high-affinity oligonucleotide ligands to purified biochemical targets.

In another embodiment, the method of decreasing the activity of a polypeptide listed in Table 1 comprises delivering to a cell or to a subject a compound that decreases the activity of a polypeptide listed in Table 1, the compound administered in an amount effective to modulate the activity of the polypeptide listed in Table 1. The compound can interact directly with the polypeptide listed in Table 1 to decrease the activity of the polypeptide. Alternatively, the compound can interact with any other polypeptide, nucleic acid or other molecule if such interaction results in a decrease of the activity of the polypeptide listed in Table 1.

The term "compound" as used herein is intended to be interpreted broadly and encompasses organic and inorganic molecules. Organic compounds include, but are not limited to, small molecules, polypeptides, lipids, carbohydrates, coenzymes, aptamers, and nucleic acid molecules (e.g., gene delivery vectors, antisense oligonucleotides, siRNA, all as described above).

Polypeptides include, but are not limited to, antibodies (described in more detail above) and enzymes. Nucleic acids include, but are not limited to, DNA, RNA and DNA-RNA chimeric molecules. Suitable RNA molecules include siRNA, antisense RNA molecules and ribozymes (all of which are described in more detail above). The nucleic acid can further encode any polypeptide such that administration of the nucleic acid and production of the polypeptide results in a decrease of the activity of a polypeptide listed in Table 1.

The compound can further be a compound that is identified by any of the screening methods described below.

In one embodiment of the invention, the polypeptide listed in Table 1 is SFRP2, which appears to stimulate angiogenesis through activation of the non-canonical Wnt pathway. The angiogenic activity of SFRP2 can be inhibited by delivering to a subject an inhibitor of this pathway, e.g., a calcineurin or NF-ATc inhibitor, e.g., an agent that inhibits calcineurin dephosphorylation of NF-ATc; an agent that inhibits nuclear translocation of dephosphorylated NF-ATc (agents that block nuclear import of NF-ATc3 and NF-ATc4; an agent that inhibits DNA binding of an NF-ATc-partner protein binding complex, e.g., through binding to a DNA binding portion of NF-ATc and/or the partner protein binding region, including agents that inhibit DNA binding by NF-ATc and agents that prevent the interaction of NF-ATc with their nuclear partner proteins; an agent that reduces the amount of intracellular NF-ATc, e.g., agents that inhibit NF-ATc expression (such as antisense or siRNA); or an agent that enhances the rate of nuclear export by activating GSK3, PKA or other NFAT kinases. Examples of inhibitors that may be used in the invention include, without limitation, tacrolimus, pimecrolimus, cyclosporin, rapamycin, and the inhibitors disclosed in U.S. Pat. Nos. 7,323,439; 7,160,863; 7,084,241; 7,019,028; 6,967,077; 6,875,571; 6,780,597; 6,686,450; 6,537,810; 6,399,322; and 5,807,693, each herein incorporated by reference in its entirety.

The compounds of the present invention can optionally be delivered in conjunction with other therapeutic agents. The additional therapeutic agents can be delivered concurrently with the compounds of the invention. As used herein, the word "concurrently" means sufficiently close in time to produce a combined effect (that is, concurrently can be simultaneously, or it can be two or more events occurring within a short time period before or after each other). In one embodiment, the compounds of the invention are administered in conjunction with anti-cancer agents, such as 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) anti-androgens (e.g., flutamide): and 17) gonadotropin-releasing hormone analogs (e.g., leuprolide). In another embodiment, the compounds of the invention are administered in conjunction with anti-angiogenesis agents, such as antibodies to VEGF (e.g., bevacizumab (AVASTIN), ranibizumab (LUCENTIS)) and other promoters of angiogenesis (e.g., bFGF, angiopoietin-1), antibodies to alpha-v/beta-3 vascular integrin (e.g., VITAXIN), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, PI-88, vatalanib, everolimus, suramin, sunitinib malate, XL184, ZD6474, ATN-161, cilenigtide, and celecoxib.

IV. Stimulation of Angiogenesis

One aspect of the invention relates to methods of increasing angiogenesis in a cell, comprising increasing the expression and/or activity of one or more polypeptides listed in Table 1 in the cell.

Another aspect of the invention relates to methods of increasing angiogenesis in a tissue of a subject, comprising increasing the expression and/or activity of one or more polypeptides listed in Table 1 in the tissue of the subject. In one embodiment, the subject is one that has vascular deficiencies, cardiovascular disease, or would benefit from the stimulation of endothelial cell activation and stabilization of newly formed microvessels or other vessels, such as in stroke, myocardial infraction, or other types of ischemia, or subjects in need of wound healing, e.g., subjects with ulcers, bed sores, burns, etc.

In one embodiment, increasing the expression and/or activity of one or more polypeptides listed in Table 1 comprises delivering a nucleic acid encoding the polypeptide or a fragment or homolog thereof to the cell or tissue. In another embodiment, increasing the expression and/or activity of one or more polypeptides listed in Table 1 comprises delivering the polypeptide itself or a fragment or homolog thereof to the cell or tissue. As used herein, the term "homolog" is used to refer to a polypeptide which differs from a naturally occurring polypeptide by minor modifications to the naturally occurring polypeptide, but which significantly retains a biological activity of the naturally occurring polypeptide. Minor modifications include, without limitation, changes in one or a few amino acid side chains, changes to one or a few amino acids (including deletions, insertions, and substitutions), changes in stereochemistry of one or a few atoms, and minor derivatizations, including, without limitation, methylation, glycosylation, phosphorylation, acetylation, myristoylation, prenylation, palmitation, amidation, and addition of glycosylphosphatidyl inositol. The term "substantially retains," as used herein, refers to a fragment, homolog, or other variant of a polypeptide that retains at least about 20% of the activity of the naturally occurring polypeptide (e.g., angiogenic activity), e.g., about 30%, 40%, 50% or more. Angiogenic activity can be measured by, e.g., measuring cell proliferation, angiogenic sprouting, tubule formation, or migration and invasion ability. Other biological activities, depending on the polypeptide, may include enzyme activity, receptor binding, ligand binding, induction of a growth factor, a cell signal transduction event, etc.

In one embodiment, the method comprises delivering to the subject an isolated polypeptide listed in Table 1. In exemplary embodiments, the polypeptide comprises, consists essentially of, or consists of the publicly known amino acid sequence of the polypeptide (disclosed in the GenBank accession numbers in Table 1) or a functional fragment thereof. In another embodiment, the isolated polypeptide comprises, consists essentially of or consists of an amino acid sequence that is at least 70% identical, e.g., at least 75%, 80%, 85%, 90%, 95%, 96%, 97%, 98%, or 99% identical to the publicly known amino acid sequence or a functional fragment thereof (and polynucleotide sequences encoding the same).

The polypeptide of the invention also include functional portions or fragments (and polynucleotide sequences encoding the same). The length of the fragment is not critical as long as it substantially retains the biological activity of the polypeptide (e.g., angiogenic activity). Illustrative fragments comprise at least about 4, 6, 8, 10, 12, 15, 20, 25, 30, 35, 40, 45, 50, 75, 100, 150, 200, or more contiguous amino acids of a polypeptide listed in Table 1.

Likewise, those skilled in the art will appreciate that the present invention also encompasses fusion polypeptides (and polynucleotide sequences encoding the same) comprising the polypeptide listed in Table 1 (or a functional fragment thereof). For example, it may be useful to express the polypeptide (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the polypeptide may be produced, e.g., fusion proteins comprising maltose binding protein (MBP) or glutathione-S-transferase. As another alternative, the fusion protein can comprise a reporter molecule. In other embodiments, the fusion protein can comprise a polypeptide that provides a function or activity that is the same as or different from the activity of the polypeptide, e.g., a targeting, binding, or enzymatic activity or function.

Likewise, it will be understood that the polypeptides specifically disclosed herein will typically tolerate substitutions in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 2

| Amino Acid | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, J. Mol. Biol. 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional polypeptides beyond those specifically disclosed herein.

In embodiments of the invention, the polynucleotide encoding the polypeptide listed in Table 1 (or functional fragment) will hybridize to the nucleic acid sequences specifically disclosed herein or fragments thereof under standard conditions as known by those skilled in the art and encode a functional polypeptide or functional fragment thereof.

For example, hybridization of such sequences may be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and conditions represented by a wash stringency of 50% formamide with 5×Denhardt's solution, 0.5% SDS and 1×SSPE at 42° C., respectively) to the polynucleotide sequences encoding the polypeptides listed in Table 1 or functional fragments thereof specifically disclosed herein. See, e.g., Sambrook et al., Molecular Cloning: A Laboratory Manual 2nd Ed. (Cold Spring Harbor, N.Y., 1989).

In other embodiments, polynucleotide sequences encoding the polypeptides listed in Table 1 have at least about 70%, 80%, 85%, 90%, 95%, 96%, 97%, 98%, 99% or higher sequence identity with the publicly known nucleic acid sequences (disclosed in the GenBank accession numbers in Table 1) or functional fragments thereof and encode a functional polypeptide or functional fragment thereof.

Further, it will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature (See, e.g., Table 2).

Likewise, the polypeptides (and fragments thereof) of the invention include polypeptides that have at least about 70%, 80%, 85%, 90%, 95%, 96%, 97%, 98%, 99% or higher amino acid sequence identity with the publicly known polypeptide sequences.

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Those skilled in the art will appreciate that the isolated polynucleotides encoding the polypeptides of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polypeptide coding sequence can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.,* 4:432 (1997)); and the rapamycin-inducible system (Magari et al., *J. Clin. Invest.* 100: 2865 (1997)).

Other tissue-specific promoters or regulatory promoters include, but are not limited to, promoters that typically confer tissue-specificity in endothelial cells. These include, but are not limited to, promoters for VE-cadherin, PPE-I, PPE-1-3×, TIE-I, TIE-2, Endoglin, von Willebrand, KDR/tik-1, FLT-I, Egr-1, ICAM-1, ICAM-2, VCAM-1, PECAM-I, and aortic carboxypeptidase-like protein (ACLP).

Moreover, specific initiation signals are generally required for efficient translation of inserted polypeptide coding sequences. These translational control sequences, which can include the ATG initiation codon and adjacent sequences, can be of a variety of origins, both natural and synthetic.

The present invention further provides cells comprising the isolated polynucleotides and polypeptides of the invention. The cell may be a cultured cell or a cell in vivo, e.g., for use in therapeutic methods, diagnostic methods, screening methods, methods for studying the biological action of the polypeptides listed in Table 1, in methods of producing the polypeptides, or in methods of maintaining or amplifying the polynucleotides of the invention, etc. In another embodiment, the cell is an ex vivo cell that has been isolated from a subject. The ex vivo cell may be modified and then reintroduced into the subject for diagnostic or therapeutic purposes.

In particular embodiments, the cell is an untransformed endothelial cell or a cell from a endothelial cell line. Endothelial cells and cell lines include, without limitation, HUVEC, HCEC, HGEC, HMEC-1, HUV-ST, ECY304, ECV304, and EA.hy926. In other embodiments, the cell is a pericyte or other cell type associated with blood vessels.

The isolated polynucleotide can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a polypeptide listed in Table 1 or functional fragment thereof operatively associated with the promoter, and, optionally, a termination sequence including a stop signal for RNA polymerase and a polyadenylation signal for polyadenylase.

Non-limiting examples of promoters of this invention include CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in Saccharomyces); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, and the gonadotropic releasing hormone gene control region active in the hypothalamus, the pyruvate kinase promoter, the villin promoter, the promoter of the fatty acid binding intestinal protein, the promoter of smooth muscle cell α-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., *Current Protocols in Molecular Biology* (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., *Science* 247:247 (1989)). Cationic lipids have been demonstrated to aid in introduction of nucleic acids into some cells in culture (Feigner and Ringold, *Nature* 337:387 (1989)). Injection of cationic lipid plasmid DNA complexes into the circulation of mice has been shown to result in expression of the DNA in lung (Brigham et al., *Am. J. Med. Sci.* 298:278 (1989)). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., *No Shinkei Geka* 20:547 (1992); PCT publication WO 91/06309; Japanese patent application 1047381; and European patent publication EP-A-43075).

Liposomes that consist of amphiphilic cationic molecules are useful as non-viral vectors for nucleic acid delivery in vitro and in vivo (reviewed in Crystal, *Science* 270:404 (1995); Blaese et al., *Cancer Gene Ther.* 2:291 (1995); Behr et al., *Bioconjugate Chem.* 5:382 (1994); Remy et al., *Bioconjugate Chem.* 5:647 (1994); and Gao et al., *Gene Therapy* 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Feigner et al., *Proc. Natl. Acad. Sci*, USA 84:7413 (1987); Loeffler et al., *Meth. Enzymol.* 217:599 (1993); Feigner et al., *J. Biol. Chem.* 269:2550 (1994)).

Several groups have reported the use of amphiphilic cationic lipid:nucleic acid complexes for in vivo transfection both in animals and in humans (reviewed in Gao et al., *Gene Therapy* 2:710 (1995); Zhu et al., *Science* 261:209 (1993); and Thierry et al., *Proc. Natl. Acad. Sci. USA* 92:9742 (1995)). U.S. Pat. No. 6,410,049 describes a method of preparing cationic lipid:nucleic acid complexes that have a prolonged shelf life.

Expression vectors can be designed for expression of polypeptides in prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technology: Methods in Enzymology* 185, Academic Press, San Diego, Calif. (1990). Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSec1 (Baldari et al., *EMBO J.* 6:229 (1987)), pMFa (Kurjan and Herskowitz, *Cell* 30:933 (1982)), pJRY88 (Schultz et al., *Gene* 54:113 (1987)), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers *Virology* 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBOI* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including calcium phosphate or calcium chloride co-precipitation, DEAE-dextran-mediated transfection, lipofection, electroporation, microinjection, DNA-loaded liposomes, LIPOFECTAMINE-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Polypeptides and fragments of the invention can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Another embodiment of the invention relates to homologs of the polypeptides of the invention that are peptidomimetic compounds that are designed based upon the amino acid sequences of the functional polypeptide fragments. Peptidomimetic compounds are synthetic compounds having a three-dimensional conformation (i.e., a "peptide motif") that is substantially the same as the three-dimensional conformation of a selected-peptide. The peptide motif provides the peptidomimetic compound with the ability to enhance angiogenesis in a manner qualitatively identical to that of the functional fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbon A, dimethylene and ketomethylene bonds, are known in the art to be generally useful substitutes for peptide bonds in the construction of protease-resistant peptidomimetics.

In one embodiment, the polynucleotides, polypeptides, or homologs thereof of the invention are administered directly to the subject. Generally, the compounds of the invention will be suspended in a pharmaceutically-acceptable carrier (e.g., physiological saline) and administered orally or by intravenous infusion, or injected subcutaneously, intramuscularly, intrathecally, intraperitoneally, intrarectally, intravaginally, intranasally, intragastrically, intratracheally, or intrapulmonarily. They are preferably delivered directly to the site of the disease or disorder, such as tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

According to certain embodiments, the polynucleotides or vectors can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957,735 to Huang et a, each of which is incorporated herein by reference in its entirety). Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene cardiac myocytes (Maurice et al., *J. Clin. Invest.* 104:21 (1999)). Intravenous delivery of cholesterol-containing cationic liposomes has been shown to preferentially target pulmonary tissues (Liu et al., *Nature Biotechnol.* 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

V. Diagnosis and Monitoring of Angiogenesis-related Diseases

The identification of polynucleotides and polypeptides that are upregulated in tumor blood vessels provides targets to be used for detection of angiogenesis and diagnosis of angiogenesis-related diseases and disorders.

One aspect of the invention relates to methods of detecting angiogenesis in a tissue of a subject, comprising obtaining a sample from the tissue and determining the expression and/or activity of one or more polypeptides listed in Table 1 in the sample, wherein an increase in expression and/or activity relative to the level of expression and/or activity in a control sample is indicative of angiogenesis. In one embodiment, the tissue is diseased tissue such as cancer tissue, e.g., breast cancer tissue. In another embodiment, the tissue is not diseased tissue.

Another aspect of the invention relates to methods of diagnosing cancer in a subject, comprising obtaining a tissue sample from the subject and determining the expression and/or activity of one or more polypeptides listed in Table 1 in the sample, wherein an increase in expression and/or activity relative to the level of expression and/or activity in a control sample is indicative of cancer.

A further aspect of the invention relates to methods of determining the angiogenesis potential of a tissue in a subject, comprising obtaining a sample from the tissue of the subject and determining the expression and/or activity of one or more polypeptides listed in Table 1 in the sample, wherein an increase in expression and/or activity relative to the level of expression and/or activity in a control sample is indicative of an increased angiogenesis potential of said tissue.

Another aspect of the invention relates to methods of determining the metastatic potential of a cancer in a subject, comprising obtaining a tissue sample from the cancer of the subject and determining the expression and/or activity of one or more polypeptides listed in Table 1 in the sample, wherein an increase in expression and/or activity relative to the level of expression and/or activity in a control sample is indicative of an increased metastatic potential of said cancer.

In each of these aspects, the expression and/or activity of more than one polypeptide listed in Table 1 may be determined, e.g., 2, 3, 4, 5, 10, 15, 20, 25, or more polypeptides. In one embodiment, said one or more polypeptides is selected from the group consisting of SFRP2, JAK3 and FAP, or combinations thereof. In another embodiment, the one or more polypeptides does not include SFRP2. In another embodiment, the one or more polypeptides does not include JAK3. In another embodiment, the one or more polypeptides does not include FAP. The tissue sample may be obtained by any method known in the art, such as surgery, biopsy, lavage, aspiration, etc. The sample may be a bodily fluid, e.g., blood, serum, plasma, saliva, urine, cerebrospinal fluid, perspiration, etc. The control sample may be from a normal (i.e., non-diseased) portion of the same tissue or cell type in the subject, from a different tissue or cell type in the subject, from a matched individual, or may be a standard derived from the average of measurements taken from a population of subjects. In one embodiment, the tissue sample is isolated blood vessels or isolated endothelial cells. Blood vessels can be isolated by any means known in the art and as described herein. Endothelial cells can be isolated by any means known in the art, e.g., cell sorting, immunoprecipitation, etc.

In one embodiment, the subject has cancer, e.g., breast cancer.

In one embodiment, determining the expression and/or activity of one or more polypeptides listed in Table 1 comprises determining the level of a nucleic acid encoding said one or more polypeptides. Determining the level of a nucleic acid can be carried out by any means known in the art and as described herein, such as Northern blots, dot blots, PCR, RT-PCR, quantitative PCR, sequence analysis, gene microarray analysis, in situ hybridization, and detection of a reporter gene. Assays for expression and/or activity can be carried out automatically or partially automatically in a machine or apparatus designed to perform such assays, e.g., using computer-assisted methods. The results of the assays can be stored in a computer database and analyzed to produce diagnostic results. In some embodiments, the diagnostic data can be analyzed, e.g., by comparing intra-patient results over time or before and after treatment or comparing inter-patient results to determine baseline and/or abnormal values in a population.

In another embodiment, determining the expression and/or activity of one or more polypeptides listed in Table 1 comprises determining the level of said one or more polypeptides. Determining the level of a polypeptide can be carried out by any means known in the art and as described herein, such as Western blots, immunoblots, immunoprecipitation, immunohistochemistry, immunofluorescence, enzyme-linked immunosorbant assays, and radioimmunoassays.

In a further embodiment, determining the expression and/or activity of one or more polypeptides listed in Table 1 comprises determining the activity of said one or more polypeptides. The activity may be any activity associated with the polypeptide, including, without limitation, angiogenic activity, enzyme activity, protein interaction, receptor binding, ligand binding, induction of a growth factor, a cell signal transduction event, etc.

The invention also relates to methods of distinguishing among breast cancer subtypes, comprising obtaining a breast cancer sample from a subject, determining the expression and/or activity of one or more polypeptides listed in Table 1 in the sample, and determining the subtype of cancer based on the pattern of expression and/or activity. In one embodiment, the method is used to distinguish between ER negative and ER positive breast cancers. In another embodiment, the method is used to distinguish between basal, Her2/neu, and luminal subtypes.

The invention further relates to methods of distinguishing between in situ and invasive breast cancers, comprising obtaining a breast cancer sample from a subject, determining the expression and/or activity of one or more polypeptides listed in Table 1 in the sample, and determining the type of cancer based on the pattern of expression and/or activity.

One aspect of the invention relates to the use of the identified markers of angiogenesis to monitor the regulation of angiogenesis due to disease or treatment of the disease. In one aspect, the invention relates to methods of monitoring the effectiveness of a treatment for cancer in a subject, comprising obtaining a sample from a subject that has received treatment for cancer, determining the expression and/or activity of one or more polypeptides listed in Table 1 in the sample, and comparing the level of expression and/or activity to the level of expression and/or activity in a control sample, wherein a decrease in the level of expression and/or activity in the sample relative to the control sample is indicative of the effectiveness of the treatment.

Another aspect of the invention relates to methods of monitoring the progression of cancer in a subject, comprising obtaining a sample from a subject that has cancer, determining the expression and/or activity of one or more polypeptides listed in Table 1 in the sample, and comparing the level of expression and/or activity to the level of expression and/or activity in a control sample, wherein an increase in the level of expression and/or activity in the sample relative to the control sample is indicative of progression of the cancer.

The control sample may be from a normal (i.e., non-diseased) portion of the same tissue or cell type in the subject, from a different tissue or cell type in the subject, from a matched individual, or may be a standard derived from the average of measurements taken from a population of subjects. In another embodiment, the control sample may be from the disease tissue of the subject, e.g., at the time of diagnosis, prior to treatment, or after a stage of treatment.

In each of these aspects, a baseline level of expression and/or activity may be determined upon the initial diagnosis of cancer or prior to the first treatment. After a baseline is established, the expression and/or activity of the one or more polypeptides may be determined repeatedly, e.g., on a regular schedule (e.g., once every 2, 3, 4, 5, or 6 days, 1, 2, 3, or 4 weeks, or more) or as desired (e.g., after each therapeutic treatment). Expression and/or activity may be determined as described above, and may be at the nucleic acid or polypeptide level. The information obtained from the monitoring may be used to modify the treatment the subject is receiving.

One aspect of the invention relates to kits useful for carrying out the methods of the invention. One embodiment relates to kits for assessing angiogenesis, comprising a reagent for determining the expression and/or activity of one or more polypeptides listed in Table 1. Another embodiment relates to kits for diagnosing cancer, comprising a reagent for determining the expression and/or activity of one or more polypeptides listed in Table 1. In each embodiment, the kits may contain reagents for determining the expression and/or activity of 2, 3, 4, 5, 10, 15, 20, 25, or more polypeptides listed in Table 1. The reagents may be nucleic acids (e.g., an oligonucleotide that specifically hybridizes to a nucleic acid encoding a polypeptide listed in Table 1 and can be used as a hybridization probe or an amplification primer), antibodies (e.g., one the specifically binds to a polypeptide listed in Table 1), or other agents that specifically recognize the polynucleotides or polypeptides of the invention.

The reagents can be conjugated to a detectable tag or detectable label. Such a tag can be any suitable tag which allows for detection of the reagents and includes, but is not limited to, any composition or label detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

In addition, the reagents can be immobilized on a substrate. Such a substrate can include any suitable substrate for immobilization of a detection reagent such as would be used in any of the previously described methods of detection. Briefly, a substrate suitable for immobilization of a detection reagent includes any solid support, such as any solid organic, biopolymer or inorganic support that can form a bond with the detection reagent without significantly effecting the activity and/or ability of the detection reagent to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and $NiO$) and sand.

The kits may further comprise other components useful for detecting expression or activity, e.g., buffers, cells, culture medium, enzymes, labeling reagents, containers, etc.

In one embodiment, the kit comprises an array of reagents for determining expression and/or activity. The array can comprise a substrate having a plurality of addresses. At least one address of the plurality includes a capture probe that binds specifically to a polynucleotide or polypeptide of the invention. The array may comprise capture probes corresponding to 5, 10, 15, 20, 25, or more of the polypeptides listed in Table 1. The array can have a density of at least, or less than, 10, 20 50, 100, 200, 500, 700, 1,000, 2,000, 5,000 or 10,000 or more addresses/cm$^2$, and ranges between. The substrate can be a two-dimensional substrate such as a glass slide, a wafer (e.g., silica or plastic), a mass spectroscopy plate, or a three-dimensional substrate such as a gel pad. Addresses in addition to addresses of the plurality can be disposed on the array.

In one embodiment, at least one address of the plurality includes a nucleic acid capture probe that hybridizes specifically to a polynucleotide of the invention, e.g., the sense or anti-sense strand. Each address of the subset can include a capture probe that hybridizes to a different region of a polynucleotide. An array can be generated by any of a variety of methods. Appropriate methods include, e.g., photolithographic methods (e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another embodiment, at least one address of the plurality includes a polypeptide capture probe that binds specifically to a polypeptide of the invention or fragment thereof. The polypeptide capture probe can be a naturally-occurring interaction partner of a polypeptide listed in Table 1, e.g., a where the polypeptide is a receptor or a receptor where the polypeptide is ligand. In one embodiment, the polypeptide is an antibody, e.g., an antibody specific for a polypeptide listed in Table 1, such as a polyclonal antibody, a monoclonal antibody, or a single-chain antibody.

VI. Screening Assays and Animal Models

The identification of polynucleotides and polypeptides that are upregulated in tumor blood vessels provides targets that can be used to screen for agents that regulate angiogenesis as well as models for studying the process of angiogenesis in vitro or in animals.

One aspect of the invention relates to methods of identifying a compound that regulates angiogenesis, comprising determining the expression and/or activity of one or more polypeptides listed in Table 1 in the presence and absence of a test compound, and selecting a compound that increases or decreases the level of expression and/or activity of the one or more polypeptides relative to the level in the absence of the compound, as a compound that regulates angiogenesis.

Another aspect of the invention relates to methods of identifying a compound useful for inhibition of tumor growth or metastasis, comprising determining the expression and/or activity of one or more polypeptides listed in Table 1 in the presence and absence of a test compound, and selecting a compound that increases the level of expression and/or activity of the one or more polypeptides relative to the level in the absence of the compound, as a compound useful for inhibition of tumor growth or metastasis.

In each aspect above, the assay may be a cell-based or cell-free assay. In one embodiment, the cell may be a primary cell, e.g., an endothelial cell or a tumor cell, such as a breast tumor cell. In another embodiment, the cell is from a cell line, e.g., an endothelial cell line or a tumor cell line. Endothelial cells and cell lines include, without limitation, HUVEC, HCEC, HGEC, HMEC-1, HUV-ST, ECY304, ECV304, and EA.hy926. The cell may be contacted with the compound in vitro (e.g., in a culture dish) or in an animal (e.g., a transgenic animal or an animal model). In one embodiment, the detected increase or decrease in expression and/or activity is statistically significant, e.g., at least $p<0.05$, e.g., $p<0.01$, 0.005, or 0.001. In another embodiment, the detected increase or decrease is at least about 10%, 20%, 30%, 40%, 50%, 60&, 70%, 80%, 90%, 100% or more.

Any desired end-point can be detected in a screening assay, e.g., binding to the polypeptide, gene or RNA, modulation of the activity of the polypeptide, modulation of angiogenesis-related pathways, and/or interference with binding by a known regulator of a polynucleotide or polypeptide. Methods of detecting the foregoing activities are known in the art and include the methods disclosed herein.

Any compound of interest can be screened according to the present invention. Suitable test compounds include organic and inorganic molecules. Suitable organic molecules can include but are not limited to small molecules (compounds less than about 1000 Daltons), polypeptides (including enzymes; antibodies, and Fab' fragments), carbohydrates, lipids, coenzymes, and nucleic acid molecules (including DNA, RNA, and chimerics and analogs thereof) and nucleotides and nucleotide analogs. In particular embodiments, the compound is an antisense nucleic acid, an siRNA, or a ribozyme that inhibits production of a polypeptide listed in Table 1.

Further, the methods of the invention can be practiced to screen a compound library, e.g., a small molecule library, a combinatorial chemical compound library, a polypeptide library, a cDNA library, a library of antisense nucleic acids, and the like, or an arrayed collection of compounds such as polypeptide and nucleic acid arrays.

In one representative embodiment, the invention provides methods of screening test compounds to identify a test compound that binds to a polypeptide listed in Table 1 or functional fragment thereof. Compounds that are identified as binding to the polypeptide or functional fragment can be subject to further screening (e.g., for modulation of angiogenesis) using the methods described herein or other suitable techniques.

Also provided are methods of screening compounds to identify those that modulate the activity of a polypeptide listed in Table 1 or functional fragment thereof. The term "modulate" is intended to refer to compounds that enhance (e.g., increase) or inhibit (e.g., reduce) the activity of the polypeptide (or functional fragment). For example, the interaction of the polypeptide or functional fragment with a binding partner can be evaluated. As another alternative, physical methods, such as NMR, can be used to assess biological function. Activity of the polypeptides listed in Table 1 or functional fragment can be evaluated by any method known in the art, including the methods disclosed herein.

Compounds that are identified as modulators of activity can optionally be further screened using the methods described herein (e.g., for binding to the polypeptide listed in Table 1 or functional fragment thereof, polynucleotide or RNA, modulation of mineralization, and the like). The compound can directly interact with the polypeptide or functional fragment, polynucleotide or mRNA and thereby modulate its activity. Alternatively, the compound can interact with any other polypeptide, nucleic acid or other molecule as long as the interaction results in a modulation of the activity of the polypeptide or functional fragment.

As another aspect, the invention provides a method of identifying compounds that modulate angiogenesis. In one representative embodiment, the method comprises contacting a polypeptide listed in Table 1 or functional fragment thereof with a test compound; and detecting whether the test compound binds to the polypeptide or functional fragment and/or modulates the activity of the polypeptide (or fragment). In another exemplary embodiment, the method comprises introducing a test compound into a cell that comprises the polypeptide listed in Table 1 or functional fragment; and detecting whether the compound binds to the polypeptide or functional fragment and/or modulates the activity of the polypeptide or functional fragment in the cell. The polypeptide can be endogenously produced in the cell. Alternatively or additionally, the cell can be modified to comprise an isolated polynucleotide encoding, and optionally overexpressing, the polypeptide or functional fragment thereof.

The screening assay can be a cell-based or cell-free assay. Further, the polypeptide listed in Table 1 (or functional fragment thereof) or polynucleotide can be free in solution, affixed to a solid support, expressed on a cell surface, or located within a cell.

With respect to cell-free binding assays, test compounds can be synthesized or otherwise affixed to a solid substrate, such as plastic pins, glass slides, plastic wells, and the like. For example, the test compounds can be immobilized utilizing conjugation of biotin and streptavidin by techniques well known in the art. The test compounds are contacted with the polypeptide or functional fragment thereof and washed. Bound polypeptide can be detected using standard techniques in the art (e.g., by radioactive or fluorescence labeling of the polypeptide or functional fragment, by ELISA methods, and the like).

Alternatively, the target can be immobilized to a solid substrate and the test compounds contacted with the bound polypeptide or functional fragment thereof. Identifying those test compounds that bind to and/or modulate the polypeptide listed in Table 1 or functional fragment can be carried out with routine techniques. For example, the test compounds can be immobilized utilizing conjugation of biotin and streptavidin by techniques well known in the art. As another illustrative example, antibodies reactive with the polypeptide or functional fragment can be bound to the wells of the plate, and the polypeptide trapped in the wells by antibody conjugation. Preparations of test compounds can be incubated in the polypeptide (or functional fragment)-presenting wells and the amount of complex trapped in the well can be quantitated.

In another representative embodiment, a fusion protein can be provided which comprises a domain that facilitates binding of the polypeptide to a matrix. For example, glutathione-S-transferase fusion proteins can be adsorbed onto glutathione sepharose beads (Sigma Chemical, St. Louis, Mo.) or glutathione derivatized microtitre plates, which are then combined with cell lysates (e.g., $^{35}$S-labeled) and the test compound, and the mixture incubated under conditions conducive to complex formation (e.g., at physiological conditions for salt and pH). Following incubation, the beads are washed to remove any unbound label, and the matrix immobilized and radiolabel detected directly, or in the supernatant after the complexes are dissociated. Alternatively, the complexes can be dissociated from the matrix, separated by SDS-PAGE, and the level of polypeptide listed in Table 1 or functional fragment thereof found in the bead fraction quantitated from the gel using standard electrophoretic techniques.

Another technique for compound screening provides for high throughput screening of compounds having suitable binding affinity to the polypeptide of interest, as described in published PCT application WO84/03564. In this method, a large number of different small test compounds are synthesized on a solid substrate, such as plastic pins or some other surface. The test compounds are reacted with the polypeptide listed in Table 1 or functional fragment thereof and washed. Bound polypeptide is then detected by methods well known in the art. Purified polypeptide or a functional fragment can also be coated directly onto plates for use in the aforementioned drug screening techniques. Alternatively, non-neutralizing antibodies can be used to capture the peptide and immobilize it on a solid support.

With respect to cell-based assays, any suitable cell can be used, including bacteria, yeast, insect cells (e.g., with a baculovirus expression system), avian cells, mammalian cells, or plant cells. In exemplary embodiments, the assay is carried out in a cell line that naturally expresses the polynucleotide or produces the polypeptide, e.g., endothelial cells or pericytes. Further, in other embodiments, it is desirable to use nontransformed cells (e.g., primary cells) as transformation may alter the function of the polypeptide.

The screening assay can be used to detect compounds that bind to or modulate the activity of the native polypeptide listed in Table 1 (e.g., polypeptide that is normally produced by the cell). Alternatively, the cell can be modified to express (e.g., overexpress) a recombinant polypeptide or functional fragment thereof. According to this embodiment, the cell can be transiently or stably transformed with a polynucleotide encoding the polypeptide listed in Table 1 or functional fragment, but is preferably stably transformed, for example, by stable integration into the genome of the organism or by expression from a stably maintained episome (e.g., Epstein Barr Virus derived episomes). In another embodiment, a polynucleotide encoding a reporter molecule can be linked to a regulatory element of the polynucleotide encoding a polypeptide listed in Table 1 and used to identify compounds that modulate expression of the polypeptide.

In a cell-based assay, the compound to be screened can interact directly with the polypeptide listed in Table 1 or functional fragment thereof (i.e., bind to it) and modulate the activity thereof. Alternatively, the compound can be one that modulates polypeptide activity (or the activity of a functional fragment) at the nucleic acid level. To illustrate, the compound can modulate transcription of the gene (or transgene), modulate the accumulation of mRNA (e.g., by affecting the rate of transcription and/or turnover of the mRNA), and/or modulate the rate and/or amount of translation of the mRNA transcript.

As a further type of cell-based binding assay, the polypeptide listed in Table 1 or functional fragment thereof can be used as a "bait protein" in a two-hybrid or three-hybrid assay (see, e.g., U.S. Pat. No. 5,283,317; Zervos et al., *Cell* 72:223 (1993); Madura et al., *J. Biol. Chem.* 268:12046 (1993); Bartel et al., *Biotechniques* 14:920 (1993); Iwabuchi et al., *Oncogene* 8:1693 (1993); and PCT publication WO94/10300), to identify other polypeptides that bind to or interact with the polypeptide of the invention or functional fragment thereof.

The two-hybrid system is based on the modular nature of most transcription factors, which consist of separable DNA-binding and activation domains. Briefly, the assay utilizes two different DNA constructs. In one construct, the polynucleotide that encodes the polypeptide listed in Table 1 or functional fragment thereof is fused to a nucleic acid encoding the DNA binding domain of a known transcription factor (e.g., GAL-4). In the other construct, a DNA sequence, optionally from a library of DNA sequences, that encodes an unidentified protein ("prey" or "sample") is fused to a nucleic acid that codes for the activation domain of the known transcription factor. If the "bait" and the "prey" proteins are able to interact in vivo, forming a complex, the DNA-binding and activation domains of the transcription factor are brought into close proximity. This proximity allows transcription of a reporter sequence (e.g., LacZ), which is operably linked to a transcriptional regulatory site responsive to the transcription factor. Expression of the reporter can be detected and cell colonies containing the functional transcription factor can be isolated and used to obtain the nucleic acid encoding the polypeptide that exhibited binding to the polypeptide listed in Table 1 or functional fragment.

As another cell-based assay, the invention provides a method of screening a compound for modulation of angiogenesis. In particular embodiments, the cell comprises an isolated polynucleotide encoding the polypeptide listed in Table 1 or functional fragment thereof. According to this embodiment, it is preferred that the isolated polynucleotide encoding the polypeptide or functional fragment is stably incorporated into the cell (i.e., by stable integration into the genome of the organism or by expression from a stably maintained episome such as Epstein Barr Virus derived episomes).

Screening assays can also be carried out in vivo in animals. Thus, as still a further aspect, the invention provides a transgenic non-human animal comprising an isolated polynucleotide encoding a polypeptide listed in Table 1 or functional fragment thereof, which can be produced according to methods well-known in the art. The transgenic non-human animal can be from any species, including avians and non-human mammals. According to this aspect of the invention, suitable non-human mammals include mice, rats, rabbits, guinea pigs, goats, sheep, pigs, and cattle. Suitable avians include chickens, ducks, geese, quail, turkeys, and pheasants.

The polynucleotide encoding the polypeptide or functional fragment can be stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells comprise and express the polynucleotide encoding the polypeptide or functional fragment so that the animal is a useful screening tool.

Exemplary methods of using the transgenic non-human animals of the invention for in vivo screening of compounds that modulate angiogenesis, tumor growth, metastasis, and/or the activity of a polypeptide listed in Table 1 comprise administering a test compound to a transgenic non-human animal (e.g., a mammal such as a mouse) comprising an isolated polynucleotide encoding a polypeptide listed in Table 1 or functional fragment thereof stably incorporated into the genome and detecting whether the test compound modulates angiogenesis, tumor growth, metastasis, and/or polypeptide activity (or the activity of a functional fragment).

It is known in the art how to measure these responses in vivo. Illustrative approaches include observation of changes that can be studied by gross examination (e.g., formation of tubules and blood vessels), histopathology, cell markers, and enzymatic activity.

Methods of making transgenic animals are known in the art. DNA or RNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility ih the embryo, and good reproductive fitness.

Introduction of the transgene into the embryo can be accomplished by any of a variety of means known in the art such as microinjection, electroporation, lipofection, or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct by Southern blot analysis of a segment of tissue. An embryo having one or more copies of the exogenous cloned construct stably integrated into the genome can be used to establish a permanent transgenic animal line.

Transgenically altered animals can be assayed after birth for the incorporation of the construct into the genome of the offspring. This can be done by hybridizing a probe corresponding to the polynucleotide sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

In particular embodiments, to create an animal model in which the activity or expression of a polypeptide listed in Table 1 is decreased, it is desirable to inactivate, replace or knock-out the endogenous gene encoding the polypeptide by homologous recombination with a transgene using embryonic stem cells. In this context, a transgene is meant to refer to heterologous nucleic acid that upon insertion within or adjacent to the gene results in a decrease or inactivation of gene expression or polypeptide amount or activity.

A knock-out of a gene means an alteration in the sequence of a gene that results in a decrease of function of the gene, preferably such that the gene expression or polypeptide amount or activity is undetectable or insignificant. Knockouts as used herein also include conditional knock-outs, where alteration of the gene can occur upon, for example, exposure of the animal to a substance that promotes gene alteration (e.g., tetracycline or ecdysone), introduction of an enzyme that promotes recombination at a gene site (e.g., Cre in the Cre-lox system), or other method for directing the gene alteration postnatally. Knock-out animals may be prepared using methods known to those of skill in the art. See, for example, Hogan, et al. (1986) Manipulating the Mouse Embryo: A Laboratory Manual, Cold Spring Harbor Laboratory Press, Cold Spring Harbor, N.Y.

A knock-out construct is a nucleic acid sequence, such as a DNA or RNA construct, which, when introduced into a cell, results in suppression (partial or complete) of expression of a polypeptide encoded by endogenous DNA in the cell. A knock-out construct as used herein may include a construct containing a first fragment from the 5' end of the gene encoding a polypeptide listed in Table 1, a second fragment from the 3' end of the gene and a DNA fragment encoding a selectable marker positioned between the first and second fragments. It should be understood by the skilled artisan that any suitable 5' and 3' fragments of a gene may be used as long as the expression of the corresponding gene is partially or completely suppressed by insertion of the transgene. Suitable selectable markers include, but are not limited to, neomycin, puromycin and hygromycin. In addition, the construct may contain a marker, such as diphtheria toxin A or thymidine kinase, for increasing the frequency of obtaining correctly targeted cells. Suitable vectors include, but are not limited to, pBLUE-SCRIPT, pBR322, and pGEM7.

Alternatively, a knock-out construct may contain RNA molecules such as antisense RNA, siRNA, and the like to decrease the expression of a gene encoding a polypeptide listed in Table 1. Typically, for stable expression the RNA molecule is placed under the control of a promoter. The promoter may be regulated, if deficiencies in the protein of interest may lead to a lethal phenotype, or the promoter may drive constitutive expression of the RNA molecule such that the gene of interest is silenced under all conditions of growth. While homologous recombination between the knock-out construct and the gene of interest may not be necessary when using an RNA molecule to decrease gene expression, it may be advantageous to target the knock-out construct to a particular location in the genome of the host organism so that unintended phenotypes are not generated by random insertion of the knock-out construct.

The knock-out construct may subsequently be incorporated into a viral or nonviral vector for delivery to the host animal or may be introduced into embryonic stem (ES) cells. ES cells are typically selected for their ability to integrate into and become part of the germ line of a developing embryo so as to create germ line transmission of the knock-out construct. Thus, any ES cell line that can do so is suitable for use herein. Suitable cell lines which may be used include, but are not limited to, the 129J ES cell line or the JI ES cell line. The cells are cultured and prepared for DNA insertion using methods well-known to the skilled artisan (e.g., see Robertson (1987) In: Teratocarcinomas and Embryonic Stem Cells: A Practical Approach, E. J. Robertson, ed. IRL Press, Washington, D.C.; Bradley et al., Curr. Topics Develop. Biol. 20:357 (1986); Hogan et al., (1986) Manipulating the Mouse Embryo: A Laboratory Manual, Cold Spring Harbor Laboratory Press, Cold Spring Harbor, N.Y.).

Insertion of the knock-out construct into the ES cells may be accomplished using a variety of methods well-known in the art, including, for example, electroporation, microinjection, and calcium phosphate treatment. For insertion of the DNA or RNA sequence, the knock-out construct nucleic acids are added to the ES cells under appropriate conditions for the insertion method chosen. If the cells are to be electroporated, the ES cells and construct nucleic acids are exposed to an electric pulse using an electroporation machine (electroporator) and following the manufacturer's guidelines for use. After electroporation, the cells are allowed to recover under suitable incubation conditions. The cells are then screened for the presence of the knockout construct.

Each knock-out construct to be introduced into the cell is first typically linearized if the knock-out construct has been inserted into a vector. Linearization is accomplished by digesting the knock-out construct with a suitable restriction endonuclease selected to cut only within the vector sequence and not within the knock-out construct sequence.

Screening for cells which contain the knock-out construct (homologous recombinants) may be done using a variety of methods. For example, as described herein, cells can be processed as needed to render DNA in them available for hybridization with a nucleic acid probe designed to hybridize only to cells containing the construct. For example, cellular DNA can be probed with $^{32}$P-labeled DNA which locates outside the targeting fragment. This technique can be used to identify those cells with proper integration of the knock-out construct. The DNA can be extracted from the cells using standard methods (e.g., see, Sambrook et al., Molecular Cloning: A Laboratory Manual 2nd Ed. (Cold Spring Harbor, N.Y., 1989)). The DNA may then be analyzed by Southern blot with a probe or probes designed to hybridize in a specific pattern to genomic DNA digested with one or more particular restriction enzymes.

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Germline transmission of the knockout construct may be determined using standard methods. Offspring resulting from implantation of embryos containing the ES cells described above are screened for the presence of the desired alteration (e.g., knock-out of the polypeptide listed in Table 1). This may be done, for example, by obtaining DNA from offspring (e.g., tail DNA) to assess for the knock-out construct, using known methods (e.g., Southern analysis, dot blot analysis, PCR analysis). See, for example, Sambrook et al., *Molecular Cloning: A Laboratory Manual* 2nd Ed. (Cold Spring Harbor, N.Y., 1989). Offspring identified as chimeras may be crossed with one another to produce homozygous knock-out animals.

Mice are often used as animal models because they are easy to house, relatively inexpensive, and easy to breed. However, other knock-out animals may also be made in accordance with the present invention such as, but not limited to, monkeys, cattle, sheep, pigs, goats, horses, dogs, cats, guinea pigs, rabbits and rats. Accordingly, appropriate vectors and promoters well-known in the art may be selected and used to generate a transgenic animal deficient in expression of a polypeptide listed in Table 1.

In another embodiment, animal models may be created using animals that are not transgenic. For example, tumor models (e.g., created by delivering tumorigenic cells into immunocompromised animals) can be used to study the effects of regulators of angiogenesis on tumor growth and metastasis. In another example, tumorigenic cells that overexpress or underexpress a polypeptide listed in Table 1 can be delivered to an animal under conditions in which tumors develop from the cells. Tumor growth in the animals can be compared to tumor growth in animals containing cells that do not overexpress or underexpress the polypeptide.

VIII. Pharmaceutical Compositions

As a further aspect, the invention provides pharmaceutical formulations and methods of administering the same to achieve any of the therapeutic effects (e.g., inhibition or stimulation of angiogenesis) discussed above. The pharmaceutical formulation may comprise any of the reagents discussed above in a pharmaceutically acceptable carrier, e.g., a polynucleotide encoding a polypeptide listed in Table 1 or a fragment thereof, a polypeptide listed in Table 1 or fragment thereof, an antibody against a polypeptide listed in Table 1, an antisense oligonucleotide, an siRNA molecule, a ribozyme, an aptamer, a peptidomimetic, a small molecule, or any other compound that modulates the activity of a polypeptide listed in Table 1, including compounds identified by the screening methods described herein.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the compound (including the physiologically acceptable salts thereof) is typically admixed with, inter alia, an acceptable carrier. The carrier can be a solid or a liquid, or both, and is preferably formulated with the compound as a unit-dose formulation, for example, a tablet, which can contain from 0.01 or 0.5% to 95% or 99% by weight of the compound. One or more compounds can be incorporated in the formulations of the invention, which can be prepared by any of the well-known techniques of pharmacy.

A further aspect of the invention is a method of treating subjects in vivo, comprising administering to a subject a pharmaceutical composition comprising a compound of the invention in a pharmaceutically acceptable carrier, wherein the pharmaceutical composition is administered in a therapeutically effective amount. Administration of the compounds of the present invention to a human subject or an animal in need thereof can be by any means known in the art for administering compounds.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor ELM (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmmol/kg and to 33 µmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of bone disease.

The present invention is more particularly described in the following examples that are intended as illustrative only since numerous modifications and variations therein will be apparent to those skilled in the art.

EXAMPLE 1

Experimental Methods

Breast tissue source: The frozen tissues and tumors used were obtained from the Lineberger Comprehensive Cancer Center Tissue Procurement and Analysis Core and have been procured from patients who were appropriately informed and who have consented to having their tissue procured for research. The tissue was obtained from primary breast tumors in patients who were not treated with neoadjuvant chemotherapy, or from patients without cancer undergoing reduction mammoplasty. The breast tumors used for microdissection were $ER^+$, $Her2/neu^-$ (luminal A immunophenotype).

Immunohistochemistry for laser capture microdissection: Portions of snap frozen breast tissue were fixed in OCT compound and sectioned at −35° C. on a cryostat at 8 µm onto polyethylene naphthalate membrane glass slides (Arcturus Bioscience, Mt View, Calif., catalogue #LCM0522). RNAse free technique was used throughout the procedure and buffers and alcohol solutions were used fresh each time. Slides were fixed in acetone for 2 minutes at 4° C. and rinsed in Hank's balanced salt solution (HBSS) (Gibco, Grand Island, N.Y.). The slides were incubated with a mouse-antihuman antibody to factor VIII-related antigen (BioGenex, San Ramon, Calif., catalogue # MU016-UC) at a 1:6 dilution for 7 minutes at 4° C. The IHC was performed with the DakoCytomation LSAB 2 system (Carpinteria, Calif.), a three step streptavidin-biotin system with the following modifications. After washing in HBSS, the biotinylated link was incubated for 5 minutes at room temperature. BCIP/NBT alkaline phosphatase developer (Vector Labs, Burlingame, Calif.) was used at a very high concentration (3 drops/300 µA buffer) and incubated for 10-15 minutes at 4° C. Slides were dehydrated in 75% ETOH for 30 seconds, 95% ETOH for 30 seconds, and 100% ETOH for 2 minutes (Arcturus, Mountain View, Calif.). Protector RNAse Inhibitor (Roche, Indianapolis, Ind.) was added at a 1:10 dilution to all buffers used in the staining process. The slides were placed on dry ice until microdissection, which occurred the same day as the immunohistochemistry (IHC).

Laser capture microdissection: Microdissection immediately followed tissue preparation. Laser capture microdissection was performed on a Leica Laser Microdissection System. Tissues to be microdissected were viewed through a video microscope and the position of the slide was adjusted so that the desired cells were under the targeting light. Activation of the UV laser cut the tissue around the groups of cells of interest. The cut tissue was then, transported by gravity to an eppendorf tube that contained 25 µl of RNA extraction buffer from the Picopure RNA Extraction Kit™ (Arcturus, Mountain View, Calif.). In order to maintain RNA integrity, slides were kept on dry ice until microdissection, and microdissection was performed for no longer than 15 minutes per slide. Fifteen slides were microdissected per sample. RNA was then extracted with the Arcturus Picopure RNA Extraction Kit™ (Arcturus, Mountain View, Calif.) as described in the manufacturer's instructions and DNAse I treated.

Amplification of RNA: RNA amplification was performed using a two round amplification system. The first round employed the RiboAmp® HS RNA Amplification Kit (Arcturus, Mountain View, Calif.). Five hundred ng from the first round of amplification was then put into the Agilent Low-Input Fluorescent Linear RNA Amplification Kit™ (Palo Alto, Calif.). This second round employed a T7 polymerase amplification that incorporated the fluorescent probe in preparation for microarray analyses.

Analyses of RNA integrity: RNA integrity was checked after the first round of amplification prior to each microarray experiment using RT-PCR detection of genes of different abundance levels and demonstration of intact, full-length cDNA preparations with the cDNA Integrity Kit (KPL, Gaithersburg, Md.). The latter system utilizes primer sets and target genes that allow evaluation of in-process or double-stranded cDNA for the presence of full-length and extended cDNA transcripts. Primer sets amplify regions of the 3' and 5' ends of the housekeeping genes GAPDH and the low expressed ADP ribosylation factor I gene. Generation of product using the 3' primer sets indicate that the gene is expressed in the system, and amplimer production using the 5' primer sets indicate full length, intact cDNA.

Measurement of amplification bias: MDA-MB-435 breast cancer cells were plated ($2.5 \times 10^6$ cells) in 75 $cm^2$ flasks or 100 mm plates in DMEM with 10% fetal bovine serum and 100 U of penicillin-streptomycin (Gibco). After 48 hours, total RNA was extracted using the Qiagen RNEASY Kit and purified with QIAquick PCR Purification Kit (Qiagen, Valencia, Calif.). Samples underwent only one round of amplification (Group A) or two rounds of amplification (Group B). Correlation coefficients among arrays were compared with interclass correlation (Hu et al., *Biotechniques* 38:121 (2005)).

Microarray experiments: Synthesis of labeled cDNA was performed as described previously with reference cDNA that is the Stratagene Human Universal Reference (Hu et al.,

*Biotechniques* 38:121 (2005)) labeled with Cy3-dUTP and sample cDNAs labeled with Cy5-dUTP. Microarray hybridizations were performed using Agilent Human oligonucleotide (Custom designed Agilent 1Av1-based for cell lines and Agilent 44k for vessel-dissected specimens) microarrays as previously described (Hu et al., *Biotechniques* 38:121 (2005)). Technical replicates (which refer to using the same RNA from one tumor on two microarrays) were performed for all vessel-dissected specimens.

Data normalization, preprocessing, and statistics: Gene expression values were quantified using the $\log_2$ ratio of the Lowess normalized red channel intensity versus green channel intensity (Yang et al., *Nucleic Acids Res.* 30:e15 (2002)). The UNC Microarray database (genome.unc.edu) was used to perform the filtering and preprocessing, and all data are available from the UMD and have been deposited into the GEO under the accession number of GSE7413. A two-class SAM (Significance Analysis of Microarrays, www-stat.stanford.edu/~tibs/SAM) (Storey, J. R. *Stat. Soc. Series B:*479 (2002); Tusher et al., *Proc. Natl. Acad. Sci. USA* 98:5116 (2001)) was performed to identify significantly differentially expressed genes between all 5 tumor vascular samples versus all 5 normal vascular samples. Each sample had a technical replicate array, thus there were 10 arrays in each group that were used for the SAM. In order to identify differentially expressed genes that encode potential membrane or secreted proteins, Gene Cards (www.genecards.org/index.shtml) was searched to identify the potential subcellular location for genes with >4 fold increased expression.

In order to interpret the gene lists derived from the results of SAM, and convert the gene list into biological themes, EASE (the Expression Analysis Systematic Explorer, david.abcc.ncifcrf.gov) analysis was applied.

Identity of cell types in microdissected vessel cells: The cell types comprising the microdissected vessels were identified by analyzing gene expression for genes known to be selectively expressed in specific populations of cells (endothelial, hematopoietic, pericytes, and epithelial) and comparing gene expression profiles from the vascular cell specimens to endothelial cell cultures in vitro and breast tumor-derived cells cultures in vitro. Human endothelial cell total RNAs were purchased from Cell Application Incorporation (San Diego, Calif.). Total RNA was purified from breast cancer cell lines using the Qiagen RNAeasy Kit. RNA integrity was determined using the RNA 6000 Nano LabChip Kit and Agilent 2100 Bioanalyzer. Genes specific for endothelium, previously characterized TEMs, hematopoietic markers, pericyte markers, and luminal epithelium were analyzed and the data displayed using Java Treeview (Saldanha, *Bioinformatics* 20:3246 (2004)).

Confirmation of Vascular Origin of Vascular Marker Genes: To validate the vascular origin of the genes associated with tumor endothelium obtained by immuno-LCM, immunohistochemistry was performed with antibodies to select gene transcripts and compared with staining on subsequent sections stained with antibodies to factor VIII-related antigen on paraffin embedded ER+, Her2/neu− breast tumors.

Commercially Available Antibodies: Rabbit polyclonal antibody to SFRP-2 (H-140) (Santa Cruz Biotechnology, Santa Cruz, Calif., catalogue # sc-13940) was used at 1:150 dilution; Rabbit polyclonal to FAP/fibroblast activation protein, alpha-Stalk region (Abcam, Cambridge, Mass., catalogue # Ab28244) was used at 1:600 dilution; Mouse monoclonal antibody to JAK3 (Genetex Inc., San Antonio, Tex., catalogue # GTX23301) was used at 1:100 dilution; Mouse anti-Hep27(17) (DHRS2) antibody, a gift from Dr. Franco Gabrielli (University di Pisa, Pisa, Italy), was used at 1:1000 dilution; Mouse-antihuman antibody to factor VIII-related antigen (BioGenex, San Ramon, Calif., catalogue # MU016-UC), was used at 1:100 dilution; Mouse monoclonal antihuman CD-19 (AbD Serotec, Raleigh, N.C., catalogue # MCA2454T) was used at 1:200).

Antibody Generation Methods: Peptides to the SLTRK6 (Cys-SRPRKVLVEQTKNEYFELKANLHAEP-DYLEVLEQQT (SEQ ID NO:8)) and SMPD3 (TSKSS-GQKGRKELLKGNGRRIDYMLHC (SEQ ID NO:9)) proteins were synthesized and conjugated to keyhole limpet hemocyanin (KLH) for the immunizations of rabbits. New Zealand White Rabbits (5-6 lbs) were immunized three times with 200 μg of the peptide conjugate mixed with Freund's Complete Adjuvant for the primary immunization. Freund's Incomplete Adjuvant was used for all booster immunizations. The route of injection was subcutaneous and intramuscular at multiple sites. Sera was collected from blood sampling after the third immunization. SLITRK6 antibody was used at 1:5000 dilution and SMPD3 antibody was used at 1:1000 dilution.

Immunohistochemistry on paraffin-embedded breast tumor and normal samples: The tissue was sectioned at 8 μm onto Superfrost plus slides. Slides were dewaxed by immersing in xylene for 5 minutes twice. Slides were hydrated in 100% ETOH, 95% ETOH for 3 minutes each. Slides were quenched in 3% $H_2O_2$ (DakoCytomation, LSAB2 HRP Kit, Carpinteria, Calif.) for 10 minutes, rinsed in 70% ETOH for 3 minutes, and then PBS for 3 minutes. Citra buffer (BioGenex, San Ramon, Calif.) was warmed in a 60° C. oven and slides were immersed in citra buffer at 100° C. in a rice steamer for 30 minutes. Slides were rinsed in PBS for 3 minutes and then marked with a PAP pen. 100 μl-200 μl of primary antibody was applied and slides were placed in a sealed box in a 4° C. cold room overnight. Slides were then rinsed in PBS for 3 minutes, and 1-2 drops of biotinylated secondary antibody (DakoCytomation, LSAB2 HRP Kit) was added to each slide for 20 minutes. Slides were rinsed in PBS for 3 minutes and 1-2 drops of streptavidin-HRP (DakoCytomation LSAB2 HRP Kit) was applied for 20 minutes. 1-2 drops of DAB complex was applied and slides were placed in a dark drawer for approximately 10 minutes. Slides were rinsed in distilled water for 3 minutes and counterstained with trypan blue (Sigma, St Louis, Mo.) for 30-45 seconds. Slides were rinsed in PBS, dehydrated through graded alcohol and xylene, and Cytoseal XYL (Richard-Allan, Kalamazoo, Mich.) and cover slides were applied. A negative control without primary antibody was performed for all experiments, and the positive control was factor VIII-related antigen.

Evaluation of Differential Protein Expression of Vascular Genes Between Breast Tumor and Normal Breast Tissue: Once the vascular genes were confirmed to localize to endothelium, it was next evaluated whether differential mRNA expression correlated with differential protein expression using immunohistochemistry on paraffin embedded breast tumors and normal breast tissue.

Selection of breast tumors: Three groups of formalin-fixed paraffin embedded breast tumors were used and designated as luminal A, basal, or Her2/neu based on their immunophenotypes (Livasy et al., *Mod. Pathol.* 19:264 (2005)) ("luminal A" ER positive, Her2/neu negative; "basal" ER negative, PR negative, HER2/neu negative; ck5/6 positive or EGFR positive; and "Her2/neu" ER negative, PR negative, Her2/neu positive) as well as normal breast tissue from reduction mammoplasty. Normal breast tissues were first stained with antibody to factor VIII-related antigen, and only tissue that had vessels in the sample were used. ER negative, PR negative, Her2/neu negative tumors were stained for CK5/6 antibody (clone 05/16B4 1:10 dilution, Boehringer Mannheim, Indianapolis) as previously described (Livasy et al., *Mod. Pathol.* 19:264 (2005)) and EGFR antibody (clone pharmDx, DakoCytomation Carpinteria, Calif.) per manufacturer's instructions to further define the basal phenotype.

Immunohistochemistry Scoring: A single board-certified pathologist (CAL) scored each tissue section for FAP, SFRP2, JAK3, SMPD3, SLITRK6, DHRS2 and CD19 expression based on a scoring system that measured intensity of stain in endothelium as: (Vessel Intensity Score) 0, none; 1, borderline; 2, weak; 3, moderate/strong, and percent positive endothelial cells staining as: 0, none; 1, 1-24%; 2, 25-49%; 3, 50-74%; 4, 75-100%. Differences in the Vessel Intensity Score between tumors and normal tissue were then dichotomized and evaluated, where a "high" score was 3 and a low score was 0-2. To further define angiogenesis expression, expression was dichotomized as high (3+ intensity and ≥75% positive cells) and not high (0, 1, or 2 intensity and/or <75% positive cells), and this was designated as the Angiogenesis Score. Fisher's exact test was used to test for possible differences in proportions (or percentages) of expression, categorized as either 'high' or 'low' for both Angiogenesis Score and Vessel Intensity Score between luminal A vs. normal, Her2neu vs. normal, and basal vs. normal tissue. Statistical analyses were performed using SAS statistical software, Versions 9.1, SAS Institute Inc., Cary, N.C.

EXAMPLE 2

Identification of Genes Differentially Expressed in Breast Tumor Vessels

Vessel isolation and microarray analysis: In order to study differences in gene expression between tumor and normal vessels, rapid NC was performed with antibodies to factor VIII-related antigen, followed by laser capture microdissection (LCM) of vascular cells from 5 luminal A breast tumors and 5 normal breast tissue specimens from reduction mammoplasty Immunostaining according to the rapid IHC protocol requires only 30-35 minutes from fixation to LCM. The quality of staining was excellent, the vascular cells were easily identified, and LCM was performed successfully (FIG. 1).

Figure 2:
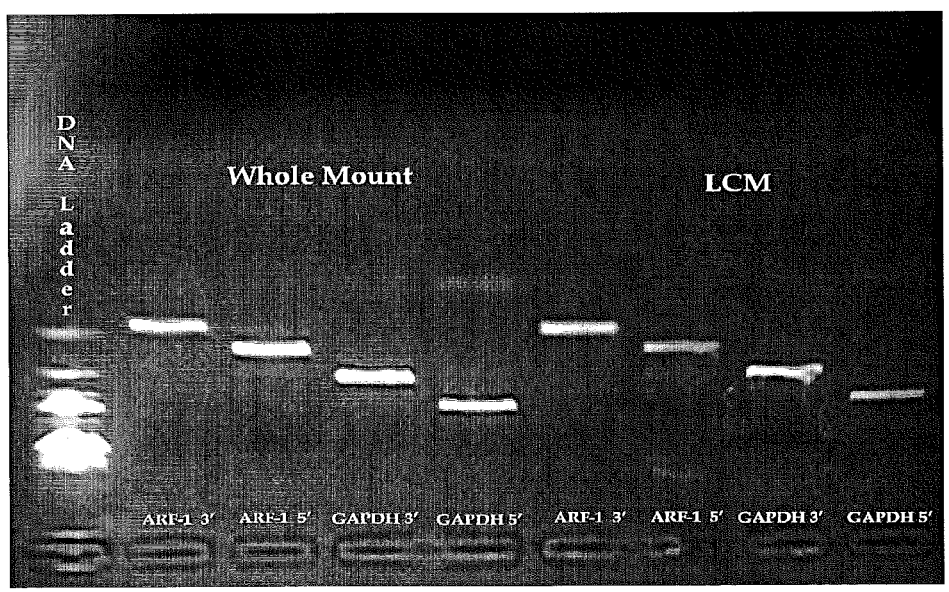
FIG. 2 shows RNA integrity analyses. RT-PCR primers for genes of low and high abundance levels were used on cDNA from "Whole mount," which refers to a frozen section of the whole tumor prior to microdissection, and "LCM," which refers to the sample of vessels microdissected from a frozen section of a human breast tumor. Lane 1, DNA ladder; Lane 2, 3' end of the low expressed ADP ribosylation factor I gene (ARF F1) from the "Whole mount" (239 bp); Lane 3, 5' end of ARF F1 from the "Whole mount" (336 bp); Lane 4, 3' end of the housekeeping gene GAPDH from the "Whole mount" (540 bp); Lane 5, 5' end of GAPDH from the "Whole mount" (887 bp); Lane 6, 3' end of ARF F1 from the microdissected vessel cells; Lane 7, 5' end of ARF F1 from the microdissected vessel cells; Lane 8, 3' end of GAPDH from the microdissected vessel cells; Lane 9, 5' end of GAPDH from the microdissected vessel cells.

RNA amplification was performed using a two round amplification system. RNA integrity was evaluated after the first round of amplification. The extracted RNA maintained its integrity as shown by RT-PCR detection of genes of different abundance levels (FIG. 2). No signals were observed after amplification of the negative control (RNA extraction buffer without the microdissected sample, data not shown). RNA integrity was checked on all samples prior to microarray hybridization and only samples that maintained RNA integrity were used for microarray analyses.

To estimate the amplification bias, one round of amplified RNA was compared to two rounds of amplification of RNA extracted from human MDA-MB-435 breast cancer cells grown in vitro. When both amplified and unamplified RNA were hybridized to 44,000 element Agilent long oligonucleotide DNA microarrays, correlation coefficients ranged from 0.95-0.97 among technical replicates.

Confirmation of vascular cell identity and purity: Genes specific to endothelium were uniformly and highly expressed in the vascular cell specimens and endothelial cell lines with significantly lower expression seen in the breast tumor cell lines, confirming that the vascular cell samples were highly enriched for endothelium (FIG. 3).

Tumor endothelial markers 1, 2, 4, 5, 6, 7, 7R, 8 (previously reported to be differentially expressed between colon tumor and normal endothelium) (St. Croix, *Science* 289:1197 (2000)) were highly expressed in both the tumor and normal vascular cells when compared relative to the low expression seen in the breast tumor cell lines (FIG. 3). Previously reported breast specific tumor vascular genes HEY1, Col4A2, C4A, SPARCL1, SNAIL1 (Parker et al., *Cancer Res.* 64:7857 (2004)) were also similarly highly expressed in the samples of both tumor and normal vascular cells, with low expression in the breast tumor cell lines (FIG. 3). These results suggest that these are markers of breast endothelium, but their expression was not consistently higher in tumor vs. normal vascular cells.

Figure 3:
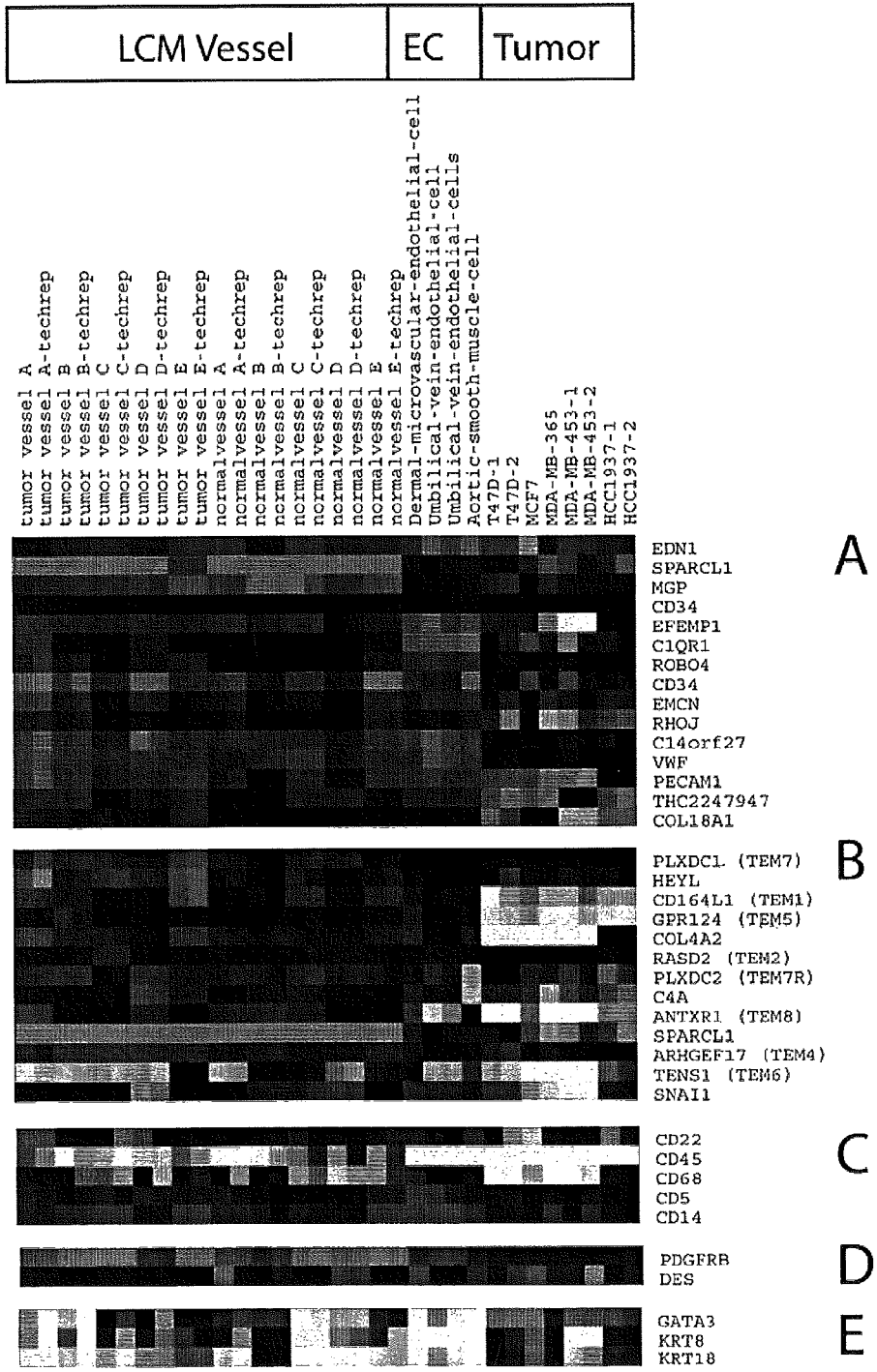
FIG. 3 shows gene expression analysis confirming vascular identity. Arrays for LCM vessel cells, endothelial cell lines, and breast tumor-derived cell lines were ordered from left to right. Arrays from endothelial cells cultured in vitro are labeled: Dermal-microvascular-endothelial-cell, Umbilical-vein-endothelial-cell, Umbilical-vein-endothelial-cells, Aortic-smooth-muscle-cell. Arrays from breast tumor-derived cell lines in vitro are labeled: T47D-1, T47D-2, MCF7, MDA-MB-365, MDA-MB-453, HCC1937-1, HCC1937-2. The data for different gene sets were identified, and clustered within each relevant category, which are in descending order: A) endothelial genes, B) TEMs, C) hematopoietic genes, D) pericyte genes, and E) epithelial genes.

Platelet derived growth factor receptor beta (PDGFR-13), a pericyte marker, was highly expressed in the vascular cells samples, which confirmed the presence of pericytes (FIG. 3). There was high expression of genes specific to luminal breast tumor epithelium in the breast cancer cell lines, with low expression in the vascular cell samples and endothelial cell lines (FIG. 3). This confirmed enrichment for endothelial cells and pericytes without high levels of expression of epithelial-associated genes.

Expression of hematopoietic markers in the vascular cells samples was similar to the expression in endothelial cell lines in vitro (FIG. 3). CD45 (leukocytes) and CD22 (B cells) had low expression in LCM vessels and endothelial cell lines. CD14 (macrophages) and CD5 (T cells) were increased in both the vascular cell samples and the endothelial cell lines. This could be explained by the presence of RNA from macrophages and T cells in the vascular cell samples. Alternatively, it is possible that CD14 and CD5 were expressed on endothelial cells, as there is previous evidence for monocyte origin of vascular cell precursors (Coukos et al., *Br. J. Cancer* 92:1182 (2005)) and expression of CD14 in endothelial cells (Jersmann, *Immunol. Cell Biol.* 83:462 (2005)); CD14 was also elevated in a previous report of microdissected ovarian tumor endothelium (Buckanovich et al., *Cancer Biol. Ther.* 5:635 (2006)), and CD5 has also previously been reported to be present on vascular endothelium (Gogolin-Ewens et al., *Eur. J. Immunol.* 19:935 (1989)).

Supervised analysis of tumor versus normal vessels: Using Significance Analysis of Microarray (SAM), differentially expressed genes between tumor and normal vascular cells were identified. 1176 genes differentially expressed were found with a median number of false significant=7.76, of which 368 were increased. In order to interpret the gene list derived from SAM and convert the gene list into biological themes, the Expression Analysis Systematic Explorer (EASE) was applied. When examining Bonferonni adjusted results, it was found that the extracellular matrix ontology category was increased in tumor vascular cells, while the ribosome ontology category was decreased, demonstrating a separate biological response.

Confirmation of Vascular Origin of Vascular Marker Genes: To validate the vascular origin of the genes associated with tumor endothelium obtained by immuno-LCM, IHC was performed on paraffin embedded luminal A human breast tumors. Since the goal was to identify highly differentially expressed genes, the first focus was on the 55 genes that had >4 fold increased expression in tumor vessel cells (Table 1). From this list, Gene Cards (www.genecards.org/index.shtml) was searched to identify the potential subcellular location for genes with >4 fold increased expression, and focused on some of the genes that potentially encode membrane proteins (FAP, JAK3, SMPD3, SLITRK6, CD 19), and a secreted protein (SFRP2). These would offer particularly good drug targets due to their accessibility. Also chosen was a gene that has recently been described to be expressed in endothelium in vitro (DHRS2) (Shafqat et al., *Cell. Mol. Life. Sci.* 63:1205 (2006)).

Antibodies to factor VIII-related antigen were used for a positive control to identify endothelium, and on subsequent sections, IHC was performed with antibodies to FAP (fibroblast activation protein, alpha), SFRP2 (Secreted frizzled-related protein 2), JAK3 (Janus kinase 3), SMPD3 (neutral sphingomyelinase 2), SLITRK6, DHRS2 (Dehydrogenase/reductase (SDR family) member 2, also known as Hep27), and CD19.

Figure 4:
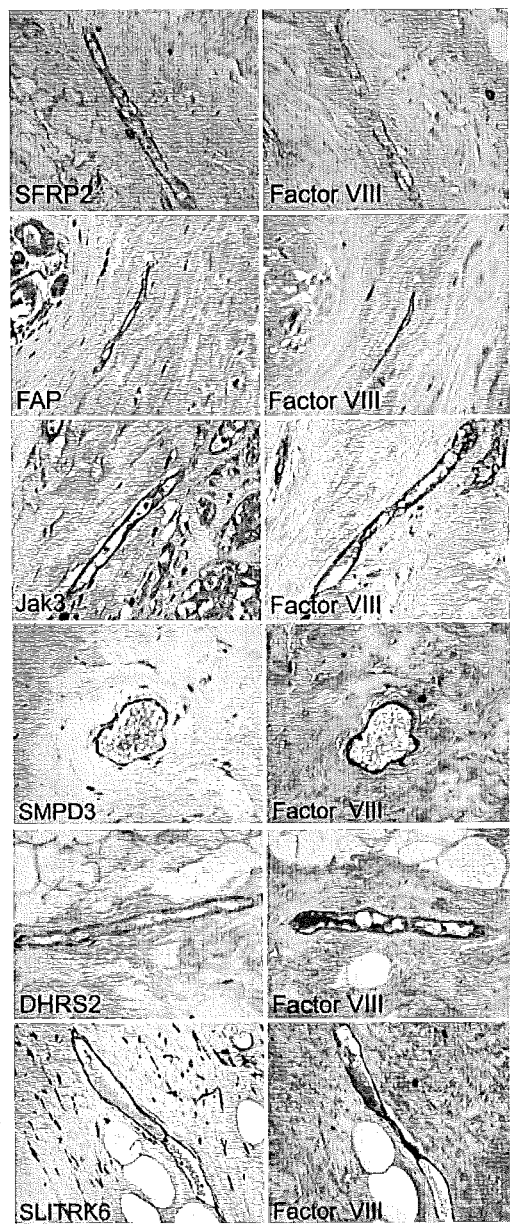
FIG. 4 shows confirmation of vascular origin of vascular marker genes. Pictures were taken at 600× magnification.

Antibodies to FAP, SFRP2, JAK3, SMPD3, SLITRK6, and DHRS2 all showed staining with cellular localization in endothelium (FIG. 4), as well as tumor stroma and tumor epithelium. CD19, a B-cell marker, did not localize to endothelium. Therefore 6/7 vascular marker genes identified by immuno-LCM that were studied appear to be validated of vascular origin.

EXAMPLE 3

Figure 5:
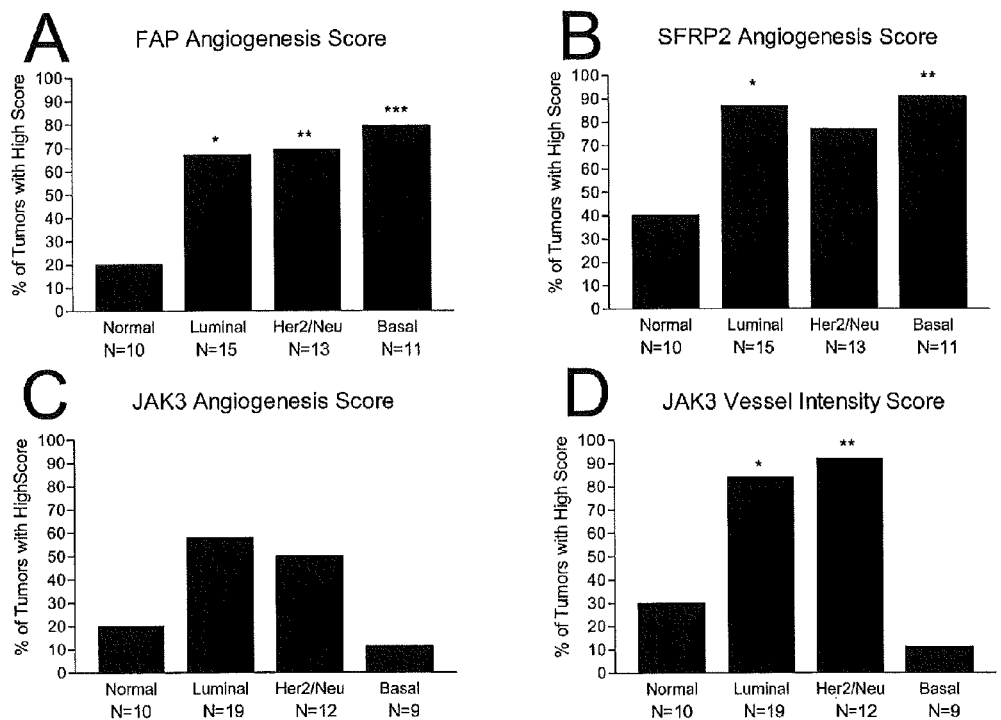
FIGS. 5A-5D shows differential protein expression of vascular genes between breast tumor vessels and normal breast vessels.

Evaluation of Differential Protein Expression of Vascular Genes Between Breast Tumor Vessels and Normal Breast Vessels For the six genes validated to be of vascular origin, it was next evaluated whether differential mRNA expression correlated with differential protein expression using IHC on paraffin embedded normal, luminal A, Her2/neu, and basal tumors. Significant differential protein expression for SLTRK6 and DHRS2 was not detected, possibly because there was very high staining in both the tumor endothelium and normal endothelium (data not shown). For SMPD3 there was no difference in the Angiogenesis Score for luminal A versus normal, but there was an increase in the Vessel Intensity Score comparing luminal A versus normal (15/16 (94%) vs. 6/10 (60%) P=0.05). JAK3 had higher staining in luminal A and Her2/neu tumors compared to normal (p=0.01 and p=0.006 respectively, FIG. 5D) and was nearly statistically significant for the Angiogenesis score (p=0.11, FIG. 5C). Basal tumors had very low expression of JAK3 (FIGS. 5C, 5D). For FAP, the Angiogenesis Scores were significantly higher in the luminal A, Her2/neu and basal tumors compared to normal (p=0.04, p=0.03, and p=0.03 respectively, see FIG. 5A). For SFRP2, the Angiogenesis Score was significantly higher in luminal A tumors and basal tumors compared to normal, (p=0.03 and p=0.02 respectively) with near significance in Her2/neu tumors (***p=0.10). This appears to validate the original discovery of differential gene expression in luminal A versus normal vessel cells on a second sample using a different platform (IHC).

EXAMPLE 4

Angiogenic Function of SFRP2

Figure 6:
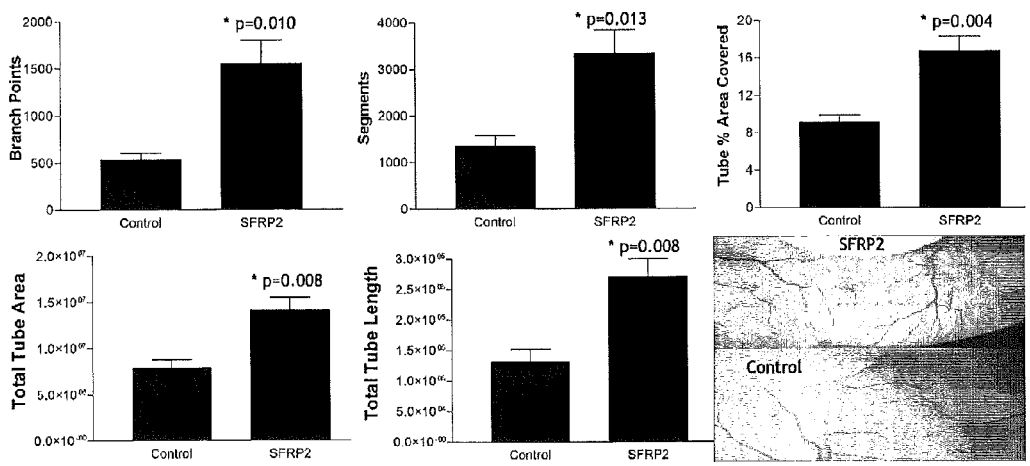
FIG. 6 shows that SFRP2 induces angiogenesis on the chorioallantoic membrane.

Chick chorioallantoic membrane (CAM) assay: To determine whether SFRP2 induces angiogenesis in vivo, fertilized chicken eggs (NC State University Chicken Research Farm) were incubated at 100° F. on an egg turner for 4 days. On day 4, the eggs were cracked into sterile Petri dishes and incubated at 99° F. in 3% $CO_2$, 65% humidity. For application of drug onto the CAM, Whatman grade 1 filter paper was cut into circles with a 6 mm diameter paper punch and autoclaved. To decrease inflammatory effects of the disk, the discs were soaked in 1 ml of 3.0 mg/ml cortisone acetate in absolute ETOH and air dried for 60 min in a laminar flow hood. On day 8, 5 disks per egg were placed on the outer third of the CAM, 2-3 mm from a vessel. Control PBS 7 µl was added to the discs for the control CAMs, and SFRP2 100 ng/7 µl PBS was added to the disks for the treated CAMs (n=5 control disks and 5 SFRP2-treated disks). The CAMs were evaluated under a stereomicroscope on day 3 after disk placement. Pictures were taken with a Wild M-4 70 Macrosystem, and angiogenesis was quantified using Metamorph Software with an angiogenesis module. To investigate whether SFRP2 induces angiogenesis in vivo, SFRP2 impregnated pellets were implanted on the developing CAM on day 8. After 3 days, SFRP2 induced angiogenesis on the CAM with a statistically significant increase in number of branch points (0.010), segments (0.013), tube percent area covered (0.004), total tube area (0.008), and total tube length (0.008) (FIG. 6).

Scratch wound assay: The migration properties of SFRP2 on mouse endothelial cells (MEC) cells were evaluated using a scratch wound assay. Mouse endothelial cells were plated at 10,000 cells/well into a 96 well plate and allowed to become confluent in DMEM with 10% FBS. The cells were quiesced in DMEM without serum for 18 hours. The wound was formed using a 1 ml pipette tip and a 0.7 µM-700 µM dose curve of mouse recombinant SFRP2 (US Biologicals, Swampscott) was added to the cells. Each concentration was performed in triplicate and the experiment was repeated three times with similar results. Migration was measured from 16 to 32 hours. Migration distance was measured at each time point. Statistical differences between SFRP2 and control were evaluated with an unpaired two-tailed Student's t-test, with p<0.05 being significant. SFRP2 increased endothelial cell migration in the picomolar concentration (p<0.01 at 16 hours, p<0.001 at 19 hours) (FIG. 7).

Tube formation assay: The tube formation properties of SFRP2 on mouse endothelial cells (MEC) cells were evaluated using an endothelial cell tube formation assay. ECMATRIX (Chemicon) was thawed, diluted and solidified in a 96 well plate according to the manufacturer's instructions. $1 \times 10^4$ cells/well in 150 µl of DMEM (cellgro) with 10% FBS (HyClone) and a concentration range (7-7000 pM) of SFRP2 (US Biologicals) were seeded onto the matrix and returned to 37° C., 5% $CO_2$ for 8 hours. Images were acquired using the Nikon Eclipse TS100 microscope at 4×magnification with a Nikon CoolPix 995 digital camera. Results were quantified by counting the number of branch points. Endothelial tube formation was induced by SFRP2 in a concentration-dependent manner at 8 hours (p=0.0006 at 7 nM) (FIG. 8).

Figure 9:
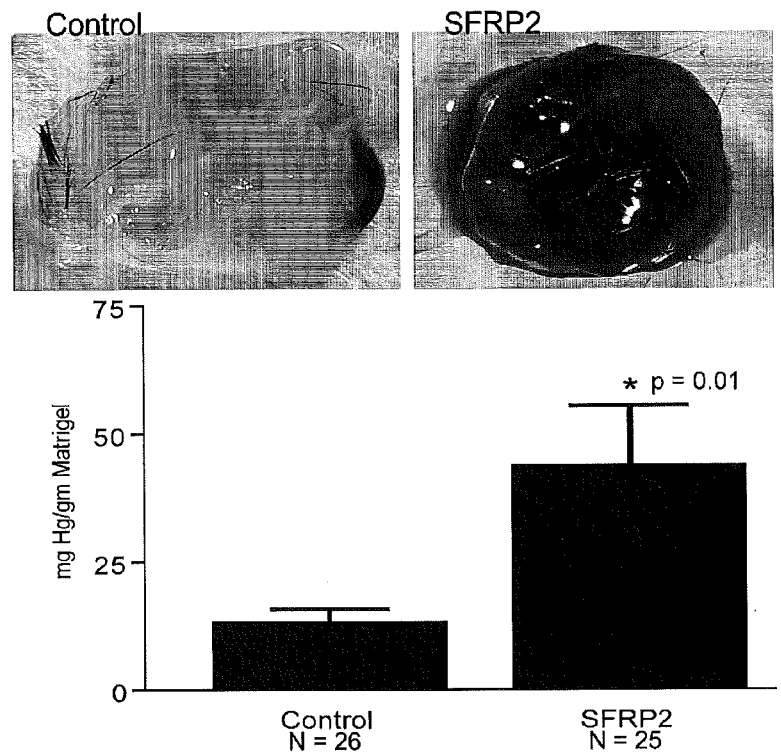
FIG. 9 shows that SFRP2 induces angiogenesis in the mouse MATRIGEL plug assay.

MATRIGEL plug assay: The ability of mouse recombinant SFRP2 would stimulate angiogenesis in a mouse MATRIGEL plug angiogenesis assay was evaluated. Female C57BL/6 mice (8 weeks old) were injected s.c. with 0.5 ml of growth factor reduced basement membrane matrix (MATRIGEL) containing either mouse recombinant SFRP2 (800 ng/ml) with 30 U/ml heparin or PBS with 30 U/ml heparin for negative control. Seven days later the mice were sacrificed and the MATRIGEL plugs removed and evaluated for angiogenesis by hemoglobin concentration with the Drabkin's reagent. Evaluation of the angiogenic response by measurement of hemoglobin content showed a 3.3 fold increase in SFRP2 plugs compared with the vehicle control (n=25 SFRP2 plugs, n=26 control plugs, p=0.01, FIG. 9).

Figure 10:
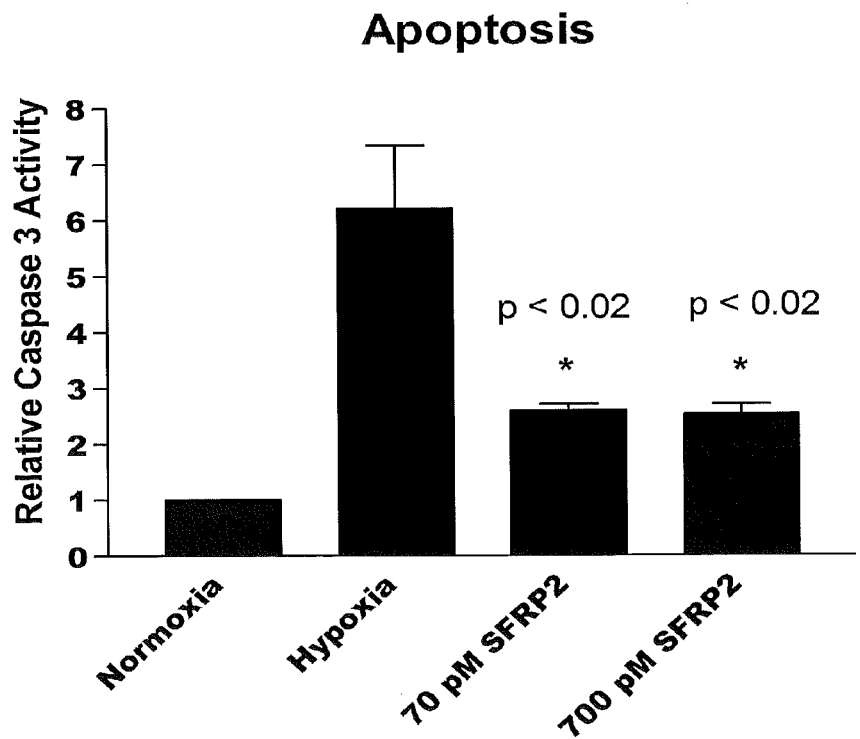
FIG. 10 shows that SFRP2 inhibits hypoxia-induced apoptosis in MEC cells.

Endothelial cell apoptosis assay: Human coronary artery endothelial cells (HCAEC) were used for apoptosis assays because apoptosis could not be induced in the MEC cells. HCAECs were grown in 10-cm dishes (Becton Dickinson, Franklin Lakes, N.J.) with endothelial cell basal medium-2 (EGM-2) BulletKit media (Clonetics, San Diego, Calif.) until 80% confluent. Medium was then replaced with optimal medium according to different assays. The hypoxic condition was created by incubating HCAECs in EGM-2 media without BulletKit growth factors at 37° C. in a hypoxia chamber with an atmosphere of 5% $CO_2$/95% $N_2$. The oxygen level in the chamber was controlled to 1.0%. Apoptosis was determined by measuring the activity of cleaved caspase 3 by using a caspase-specific fluorogenic substrate according to the protocol for the Caspase 3 Assay Kit (Sigma). HCAECs were lysed after treatment with concentrations of SFRP2 (70 µM and 700 µM) for 36 h under hypoxia. Then, 5 µl of cell extract was incubated in reaction buffer at room temperature for 1 h. The enzyme-catalyzed release of 7-amino-4-methyl coumarin (AMC) was measured by a fluorescence microplate reader. It was found that SFRP2 protected against hypoxia induced endothelial cell apoptosis ($p<0.02$) (FIG. 10).

Figure 11:
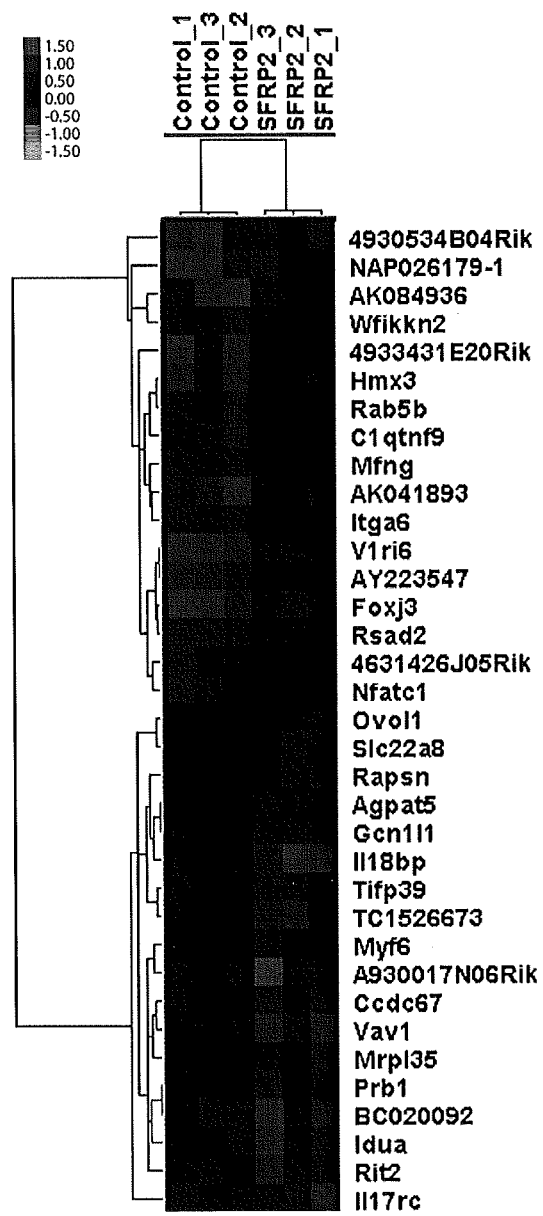
FIG. 11 shows gene expression profiling of endothelial cells treated with and without SFRP2.

Gene expression analyses: The downstream effects of SFRP2 on gene expression profiles were evaluated using oligonucleotide microarrays. MEC cells were cultured with and without SFRP2 700 pM for 16 hours. RNA was extracted and purified using the Qiagen RNEASY Kit (Qiagen). The concentration and purity of the total RNA was determined spectrophotometrically, and integrity was verified using the RNA 6000 Nano LabChip (Agilent Technologies) and Agilent 2100 bioanalyzer (Agilent Technologies). Biologic replicates were (n=3) for each group to improve confidence for the average experimental-to-control intensity ratio for each gene. RNA from cells was labeled with Cy5-CTP using the Low-Input Linear RNA Amplification System (Agilent), and hybridized with equimolar concentrations of Cy3-labeled mouse common reference RNA. Microarray hybridizations were performed using Agilent Mouse Whole Genome 44 K oligonucleotide microarrays. After hybridization, the arrays were scanned on an Axon Gene Pix 4000b scanner (Axon Instruments, Inc., Foster City, Calif.). The images were analyzed using Feature Extraction V 9.1 software (Agilent). Gene expression values were quantified by the $Log_2$ ratio of red channel intensity versus green channel intensity (sample vs. reference), followed by loess normalization to remove the intensity dependent dye bias and variation. Data filtering and pre-processing were performed using custom Perl scripts. Data associated with this study are available at genome.unc.edu/pubsup/breastTumor. Significantly differentially expressed genes were identified using an heteroscedastic (two-tailed, type 3) T test ($p<0.01$), and subsequent selection for an absolute mean fold change of >1.3. To interpret the gene lists and convert them into biological themes, the GATHER web interface (Gene Annotation Tool to Help Explain Relationships; gather.genome.duke.edu) was used for analysis. Using this technique, 33 differentially expressed mRNAs were found (FIG. 11).

Figure 12:
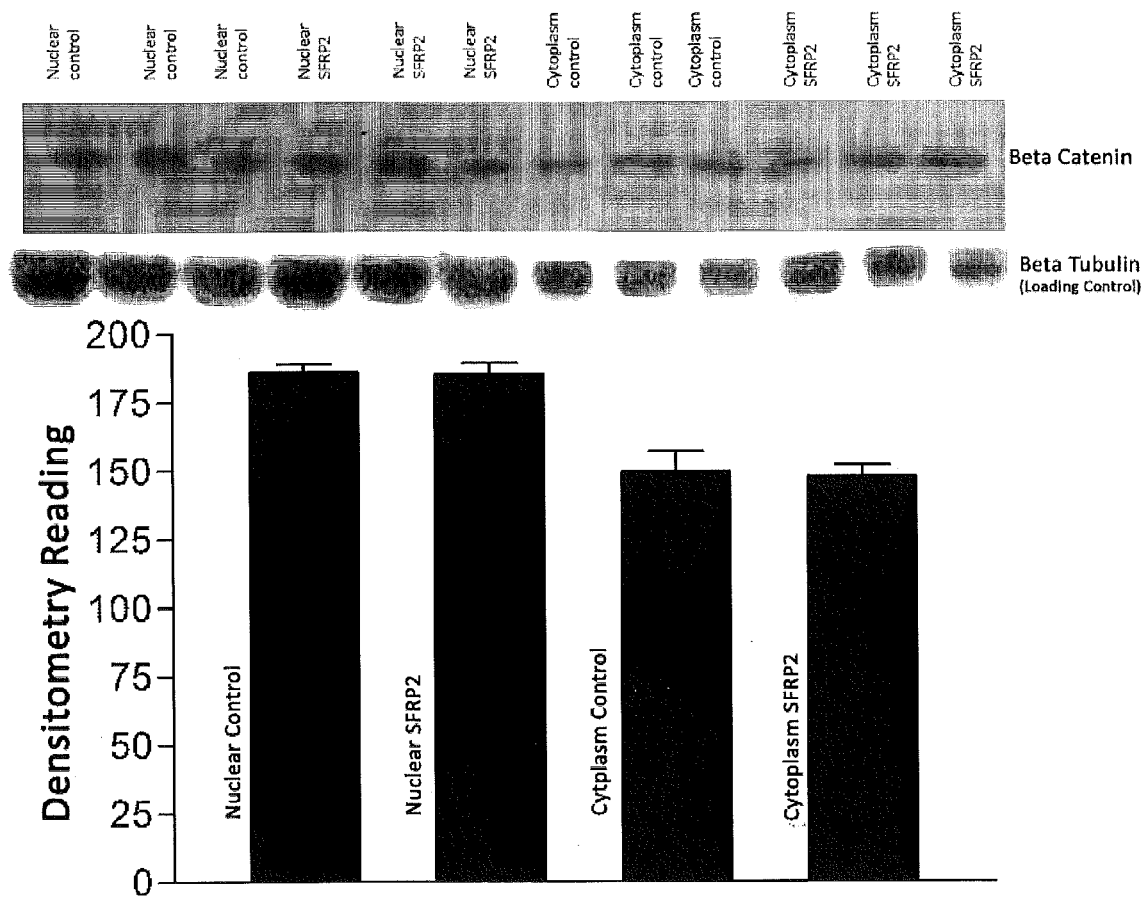
FIG. 12 shows Western blot analysis for nuclear and cytoplasmic β-catenin expression in mouse endothelial cells treated with SFRP2.

Effect of SFRP2 on Wnt pathways: SFRP2 has been described as both a Wnt antagonist and agonist, but its effects on Wnt signaling in endothelial cells have not been elucidated. To determine if SFRP2 mediates canonical Wnt signaling in endothelial cells, cytoplasmic and nuclear β-catenin levels were measured in SFRP2-treated endothelial cells. Mouse endothelial cells were plated in 12-well plates and allowed to attach overnight. The next day, the media was changed and added to the wells with and without SFRP2 (700 µM). Cells were incubated for 16 hours, and the nuclear and cytoplasmic proteins were extracted by using NE-PER™ nuclear and cytoplasmic extraction reagent from PIERCE (Pierce Biotechnology) as described in the manufacturer's manual. Western blot analysis was performed using standard methods, with primary antibody to the dephosphorylated (active) β-catenin antibody (Santa Cruz, Clone BDI480, catalog #sc-59893). There was no change in nuclear β-catenin in the SFRP2-stimulated cells, suggesting that the angiogenic property of SFRP2 is not mediated through the canonical Wnt signaling pathway (FIG. 12).

To evaluate the role of the non-canonical Wnt/$Ca^{++}$ pathway in SFRP2 induced angiogenesis, nuclear dephosphorylated NFATc3 protein levels were compared in control and SFRP2-treated endothelial cells. MEC cells were plated in 12-well plates and allowed to attach overnight. The next day, the media was changed and added to the wells with and without SFRP2 (700 µM). Cells were incubated for 1, 2, 4, 8 and 16 hours, and the nuclear proteins were extracted by using NE-PER™ nuclear and cytoplasmic extraction reagent from PIERCE (Pierce Biotechnology) as described in the manufacturer's manual. The Western blot analysis was performed using standard methods, with primary antibody to the dephosphorylated (active) β-catenin antibody or NFATc3. As above, there was no change in nuclear β-catenin in the SFRP2-stimulated endothelial cells ($p=0.4$, FIG. 13), suggesting that the angiogenic property of SFRP2 is not mediated through the canonical Wnt signaling pathway. It was found that NFATc3 was increased at 30 minutes in the nuclear fraction of SFRP2-treated endothelial cells (FIG. 13).

Figure 14:
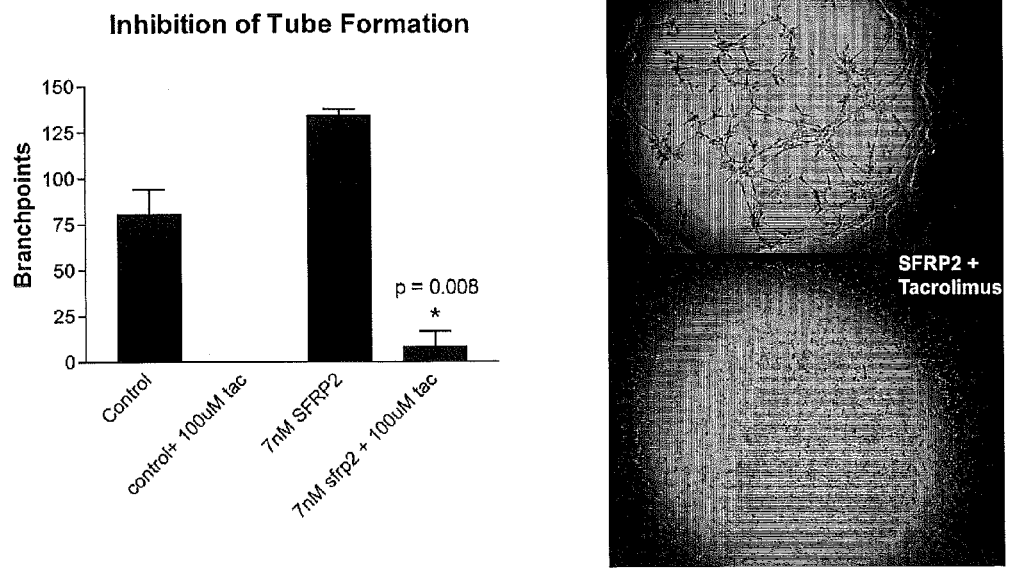
FIG. 14 shows that tacrolimus inhibits SFRP2-induced mouse endothelial cell tube formation in vitro.
Figure 15:
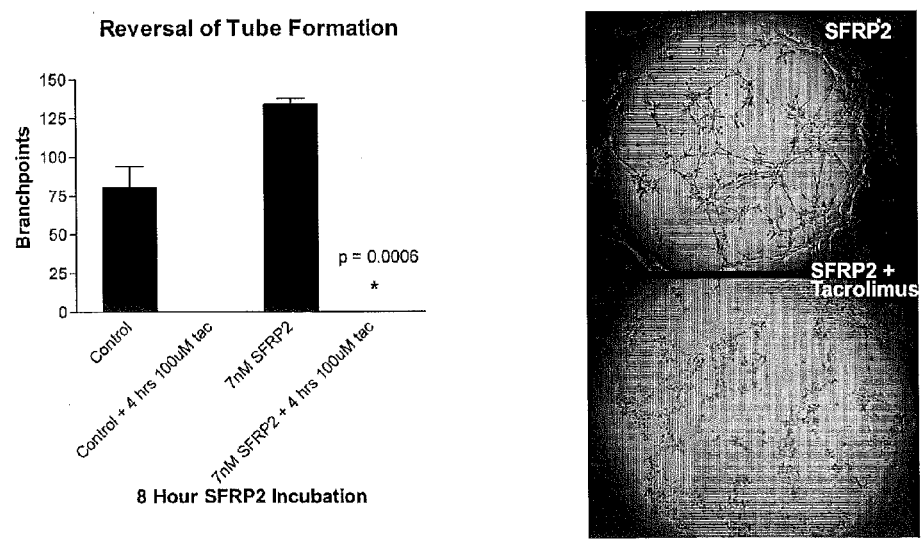
FIG. 15 shows that tacrolimus reverses SFRP2-induced mouse endothelial cell tube formation in vitro.

To evaluate whether tacrolimus inhibits SFRP2 induced tube formation, MEC cells were treated as above with SFRP2 7 nM with and without tacrolimus 100 uM for 8 hours and branch points were determined as described above. To evaluate whether tacrolimus reversed established tubes, cells were incubated with SFRP2 7 nM for 8 hours and then BSA or tacrolimus 100 µM was added to SFRP2 treated cells for an additional 4 hours, and then the number of branch points were counted. Tacrolimus inhibited SFRP2 induced tube formation in MEC cells (FIG. 14). Tacrolimus was not cytotoxic to MEC cells, as only 5% of tacrolimus-treated cells took up trypan blue dye (data not shown). In addition, after tubes were formed with treatment with SFRP2, tacrolimus reversed SFRP2-induced tube formation (FIG. 15).

A mouse model of angiosarcoma overexpresses SFRP2 protein: In order to study whether inhibition of SFRP2 will inhibit tumor growth, we set out to identify a tumor model that overexpresses SFRP2. To do this, a transformed mouse endothelial cells line were studied. Ms1 cells were generated by immortalizing murine endothelial cells by expressing the temperature-sensitive large T antigen (gift of Dr. Jack Arbiser, Emory University). Upon implantation into mice, these cells form dormant hemangiomas. Ms1 cells were then transfected with Ras (SVR cell line), and this cell line forms angiosarcomas when injected into nude mice. Protein lysates were collected from MS1 and SVR cell lines and, using Western blot analyses probing for SFRP2, found that SFRP2 was increased in SVR cells (FIG. 16). Since this cell line forms aggressive angiosarcomas, it is an ideal mouse model to study inhibition of tumor growth by inhibitors of SFRP2.

Tube formation assay: The tube formation properties of SFRP2 on MEC cells were evaluated using an endothelial cell tube formation assay. ECMATRIX (Chemicon) was thawed, diluted and solidified in a 96 well plate according to the manufactures instructions. $1\times10^4$ cells / well in 150 µl of DMEM (cellgro) with 10% FBS (HyClone) and a concentration range (3-3000pM) of SFRP2 (US Biologicals) were seeded onto the matrix and returned to 37° C., 5 % $CO_2$ for 8 hours. Images were acquired using the Nikon Eclipse TS 100 microscope at 4×magnification with a Nikon CoolPix 995 digital camera. Results were quantified by counting the number of branch point. To evaluate whether tacrolimus inhibits SFRP2 induced tube formation, MEC cells were treated as above with SFRP2 30 nM with and without tacrolimus (1 µM

- 100 μM) for 8 hours and branch points were determined as described above. To evaluate whether inhibitors of SFRP2-mediated angiogenesis would inhibit the growth of SVR tumor cells, SVR cells were treated with tacrolimus (1μM - 100 μM) or with a rabbit polyclonal antibody to SFRP-2 (H-140) (Santa Cruz Biotechnology, Santa Cruz, Calif., catalogue # sc-13940) in the tube formation assay.

As shown above, MEC endothelial tube formation was induced by SFRP2 in a concentration-dependent manner at 8 hours (p=0.0006 at 7 nM) (FIG. 17A). To further evaluate whether the angiogenic effects of SFRP2 were mediated through NFAT, endothelial cells were treated in a tube formation assay with SFRP2 (30 nM) with and without the calcineurin inhibitor tacrolimus. Tacrolimus (1 μM) inhibited SFRP2 induced tube formation by 64%+(0.002) (FIG. 17B). Tacrolimus was not cytotoxic to MEC cells, as only 5% of tacrolimus-treated cells took up trypan blue dye (data not shown). Tube formation in SVR angiosarcoma cells were also inhibited by tacrolimus (FIG. 17C), and SVR tube formation was inhibited by a polyclonal antibody to SFRP2, suggesting that SFRP2 is required for tube formation in this angiosarcoma tumor cell line (FIG. 17D).

Figure 18:
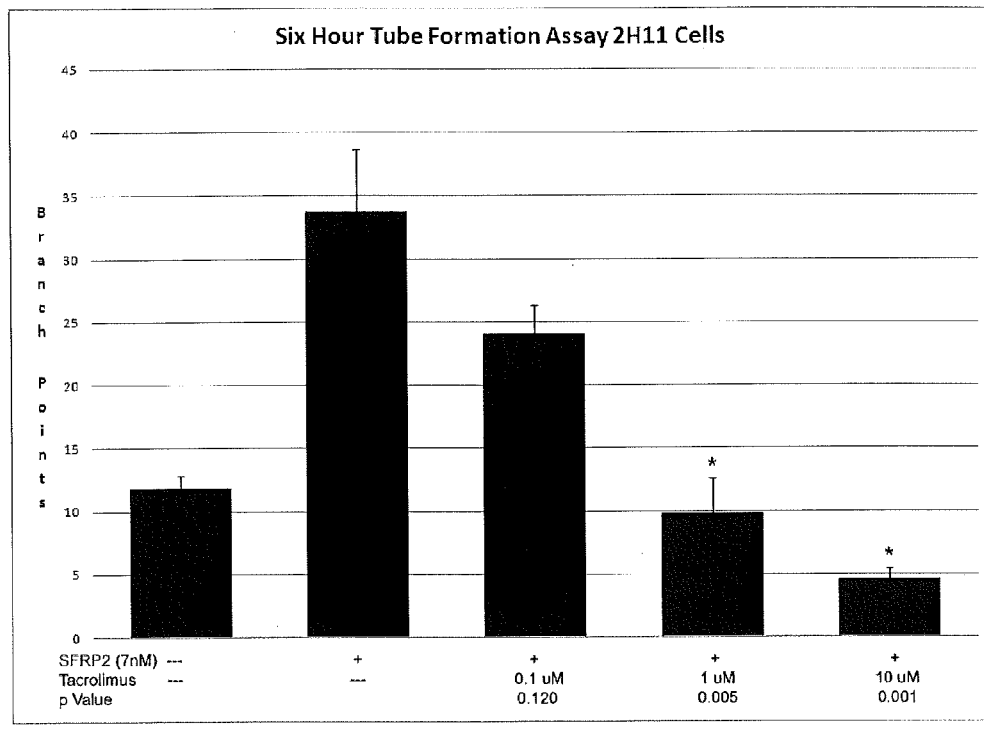
FIG. 18 shows that tacrolimus inhibits SFRP2-induced mouse endothelial cell tube formation in 2H11 cells in vitro.
Figure 19:
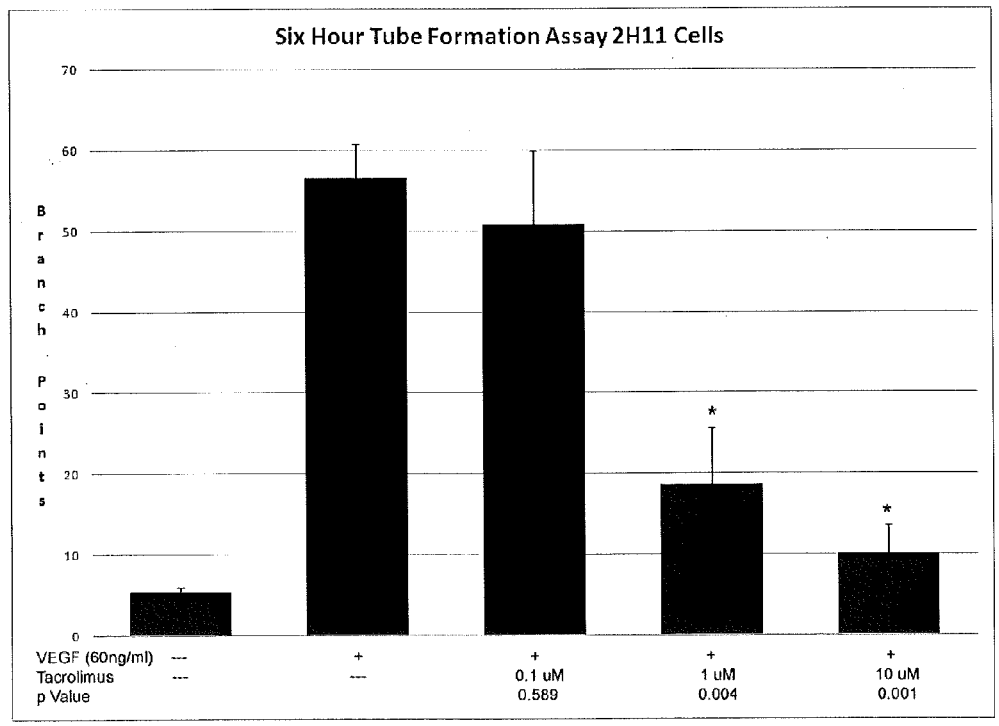
FIG. 19 shows that tacrolimus inhibits VEGF-induced mouse endothelial cell tube formation in 2H11 cells in vitro.

The ability for tacrolimus to inhibit SFRP2 and VEGF stimulated 2H11 endothelial tube formation in vitro was studied in a MATRIGEL tube formation assay. Tacrolimus inhibited endothelial tube formation in both SFRP2 (FIG. 18) and VEGF (FIG. 19) stimulated endothelial cells.

Figure 20:
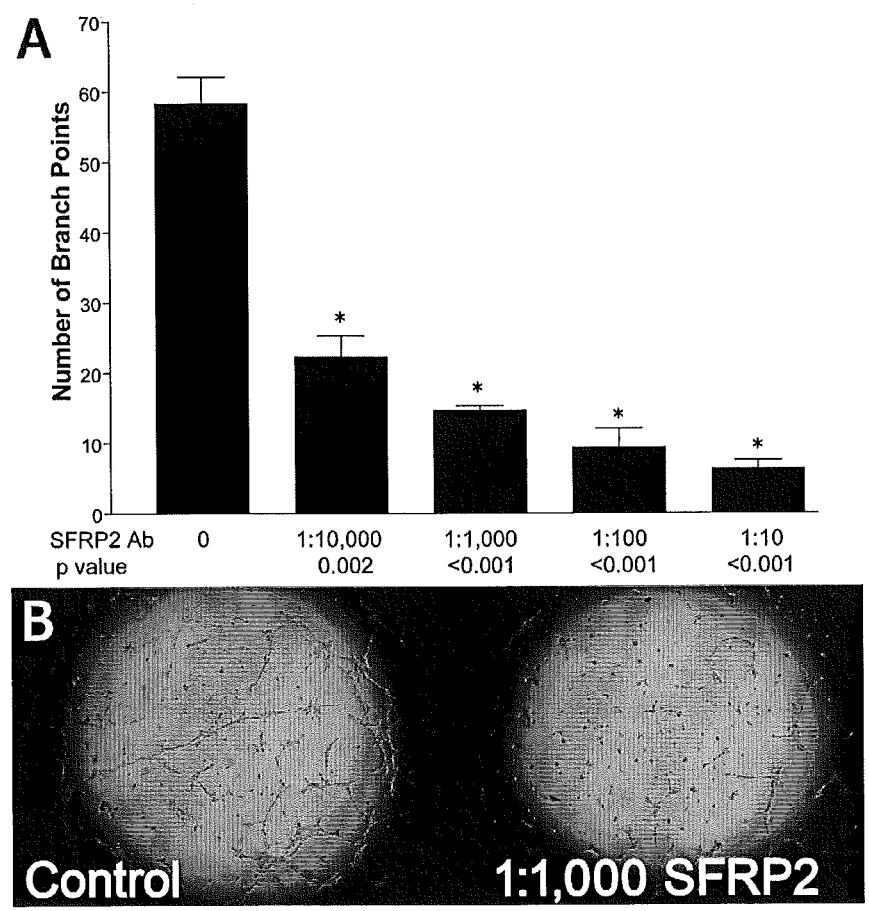
FIGS. 20A-20B show that a polyclonal antibody to SFRP2 inhibits SVR tube formation in vitro.
Figure 21:
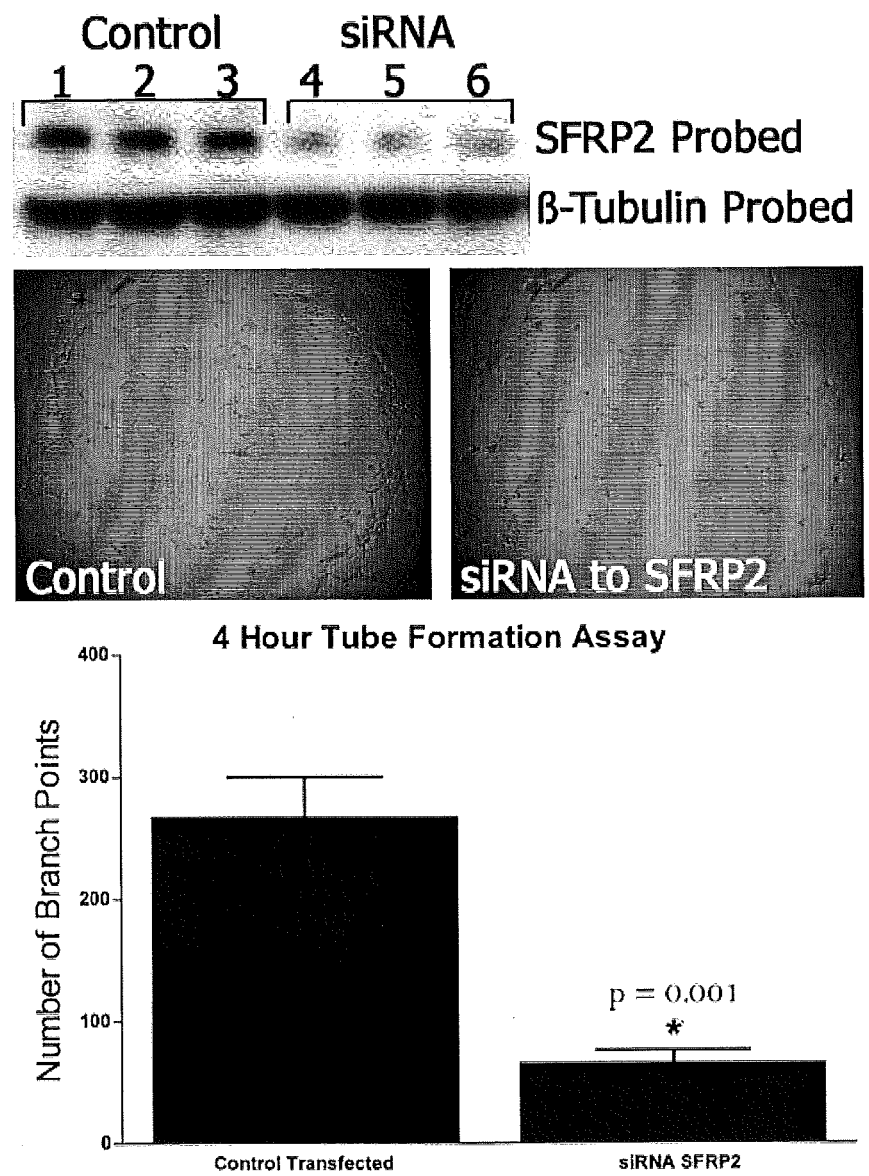
FIG. 21 shows that a siRNA to SFRP2 inhibits SVR tube formation in vitro.

As a further test of the contribution of SFRP2 to endothelial tube formation, it was evaluated whether loss of function of SFRP2 would inhibit SVR angiosarcoma tube formation. This was studied two different ways, first with a blocking antibody to SFRP2, and then using siRNA to SFRP2. SVR cells were plated in MATRIGEL in a tube formation assay and treated with a polyclonal antibody to SFRP2. SVR tube formation was inhibited with the polyclonal antibody to SFRP2 in a concentration dependent manner (FIGS. 20A-B). Next, SVR cells were transfected with siRNA to SFRP2 from Santa Cruz and sham control. SVR cells were transfected with 72 μM siRNA for SFRP2 (FRP-2 siRNA (sc-40001, Santa Cruz Biotechnology) is a pool of 3 target-specific 20-25 nt siRNAs designed to knock down SFRP2 gene expression). The three sequences are 5'-GAGAUAACGUACAUCAACA-3' (SEQ ID NO:10), 5'-CAAGCUGCAAUGCUAGUUU-3' (SEQ ID NO:11), 5'-CCAUGUCAGGCGAAUUGUU-3' (SEQ ID NO:12). The control siRNA (sc-36869, Santa Cruz Biotechnology) that was used contains a scrambled sequence that does not lead to the specific degradation of any known cellular mRNA. SVR cells were maintained in Dulbecco's modified Eagle's medium supplemented with 10% fetal calf serum. After 72 h of transfection using LIPOFECTAMINE™ RNAiMAX Transfection reagent (Invitrogen) according to the manufacturer's protocol, cells were harvested and ready for Western blot analyses and tube formation assay. Cells were seeded for a 4 hour tube formation assay. siRNA to SFRP2 transfected cells had a 70% reduction in tube formation compared to sham transfected cells (FIG. 21). These studies demonstrate that SFRP2 is required for angiosarcoma tube formation.

SFRP2 belongs to a large family of secreted frizzle-related proteins (SFRPs) which are related to the Wnt-signaling cascade. This protein contains a cysteine-rich domain which is homologous to the putative Wnt-binding domain. The Wnt-signaling network influences biological processes ranging from developmental cell fate to cell adhesion and apoptosis. Recent data suggests that the Wnt signaling pathway is involved in formation and remodeling of blood vessels.

Wnt proteins have been grouped into two classes—canonical and noncanonical. Canonical Wnts stabilize β-catenin, thereby activating transcription of Tcf/LEF target genes. SFRP2 has been reported to be an antagonist of the canonical Wnt signaling pathway by binding directly to Wnts, thereby altering their ability to bind to the Wnt receptor complex. However, in our study we found no change in cytoplasmic or nuclear β-catenin levels in SFRP2-treated endothelial cells at the concentration and time points which induced tube formation and migration, indicating that SFRP2 is not mediating angiogenesis via the canonical-Wnt signaling pathway.

Noncanonical Wnts activate other signaling pathways, such as the Wnt/$Ca^{2+}$ pathway which regulate NFATc. The NFAT family consists of four members (NFATe1-c4), which exist as transcriptionally inactive, cytosolic phosphoproteins. NFAT nuclear localization is dependent on a dynamic import-export balance between the activity of the $Ca^{2+}$/calmodulin-dependent phosphatase, calcineurin, and the activity of serine/threonine kinases. Loss-of-function mutants have shown that NFAT signaling is crucial for normal heart valves and vascular development during embryogenesis. Postnatally, this pathway contributes to the regulation of cell growth, differentiation, and cell cycle progression in various cell types, and there is increasing data supporting a critical role of NFAT in mediating angiogenic responses.

Wnt5a has been shown to be a mediator of the non-canonical Wnt pathway, and SFRP2 has previously been shown to bind to Wnt5a in the nanomolar range. Based on this, it was evaluated whether SFRP2 activated the non-canonical Wnt pathway in endothelial cells. Tacrolimus, a calcineurin inhibitor, inhibited SFRP2 induced tube formation, suggesting that SFRP2 induces tube formation via the non-canonical Wnt-$Ca^{2+}$ signaling pathway, resulting in nuclear translocation of NFATc.

EXAMPLE 5

Antibodies to SFRP2

An analysis of the amino acid sequence of the human SFRP2 sequence was performed to determine candidate epitopes for making synthetic peptides for injection into animals to develop monoclonal antibodies to human SFRP2. Seven candidate sequences were identified based on their predicted immunogenicity: AA29-40: GQPDFSYRSNC (SEQ ED NO:1); AA85-96 KQCHPDTKKELC (SEQ ID NO:2); AA119-125: VQVKDRC (SEQ ID NO:3); AA138-152 DMLECDRFPQDNDLC (SEQ ID NO:4); AA173-190: EACKNKNDDDNDIMETLC (SEQ ID NO:5); AA202-220 EITYINRDTKIILETKSKT-Cys (SEQ ID NO:6); AA270-295: ITSVKRWQKGQREFKRISRSIRKLQC (SEQ ID NO:7). Mice were immunized against the first five of the above peptide sequences with a second round of immunization one month later and bleeds performed two weeks later. An ELISA was performed to determine the titer of the mice to the peptides, which demonstrated that the mice responded to the various immunogens. Sera from the mouse immunized against the immunogen used as the epitope corresponding to amino acids AA202-AA220 (which was designated AbB) and AA270-AA295 (which was designated AbC) inhibited SVR tube formation compared to control mouse sera (FIG. 22), indicating that these peptide sequence are functionally active. These two peptides were selected for the production of a monoclonal antibody.

Figure 23A:
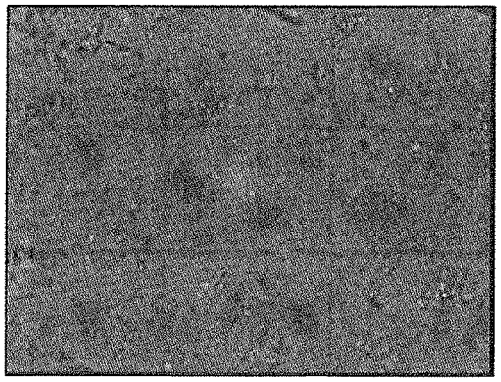
FIGS. 23A-23C show that monoclonal antibodies raised against SFRP2 inhibit tube formation. A) Representative control well. B) Angiosarcoma cells treated with supernatant from antibody secreting hybridoma showing inhibition of tube formation. C) Branch points from control angiosarcoma cells compared with the supernatants from the 8 hybridomas selected for further subcloning.
Figure 23B:
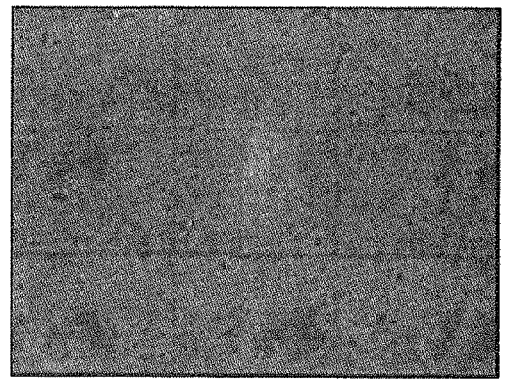
Figure 23C:
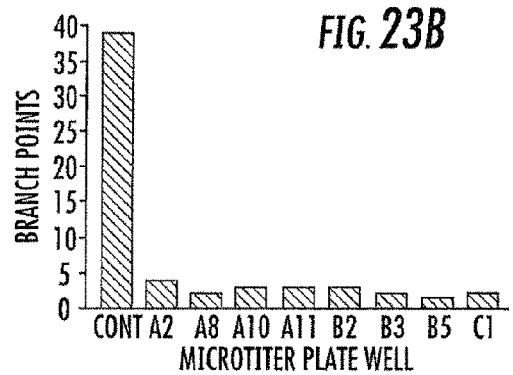

Monoclonal antibodies for the epitope corresponding to AbB (AA202-AA220) were prepared. A tertiary injection of antigen had be performed and the mice were boosted by a single intraperitoneal injection. The titers to the immunogen in the injected mice were elevated, and two mice were selected for spleen harvest. The mice selected underwent a final i.p. immunization three weeks after the last immunization. These mice were sacrificed 3 days after the final boost and blood was collected. The spleen was removed and fused with myeloma cells for hybridoma formation. The fusion of the spleen cells was with P3 x63-Ag8.653 (ATCC CRL-1580) cells using a 50% PEG solution. The fusion was plated in 96 well plates at a total cell concentration of ~$1.5 \times 10^5$ cells per well in the HAT selection media. The fusion plates were fed after 7 days with HAT media. Fusion plates were screened 14 days after the fusion was performed. The screening was performed by plating SVR angiosarcoma cells in a MATRI-GEL tube formation assay in 96 well plates. The angiosarcoma cells were suspended in 150 µl of antibody containing growth media for 90 different samples and control media. After 6 hours, pictures were taken and the number of branch points for each well was counted. The controls formed 39 branchpoints. There were 61 samples that had a >50% inhibition of tube formation, Eight samples that each had less than 4 branchpoints (FIG. 23) were selected to use for further subcloning, and 32 samples that have >50% inhibition were frozen back.

EXAMPLE 6

SFRP2 as a Biomarker for Breast Cancers

Figure 24:
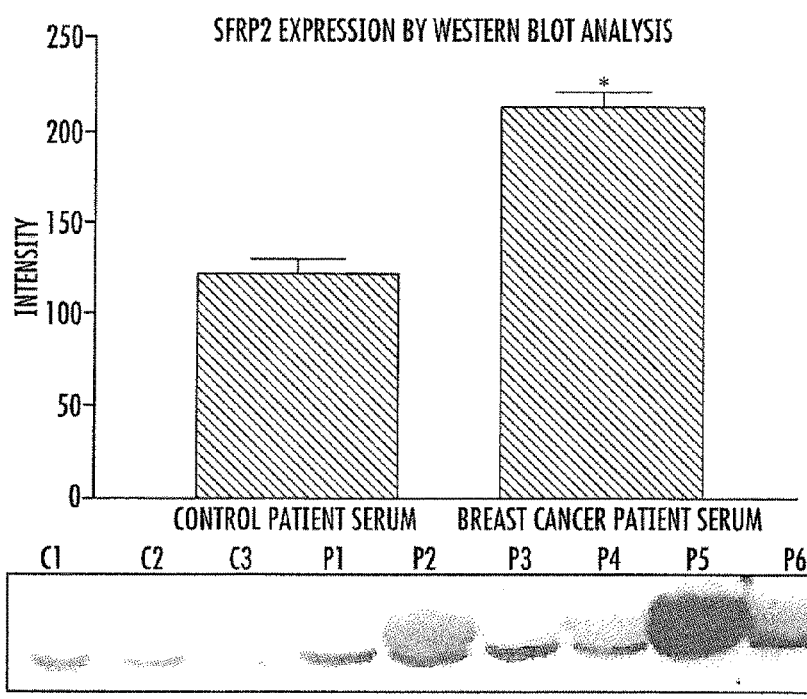
FIG. 24 shows that SFRP2 is overexpressed in serum of cancer patients. Lanes C1-C3 are controls and lanes P1-P6 are breast cancer patients' serum samples (p<0.0001).

To investigate whether SFRP2 is a biomarker for breast cancer, the presence of SFRP2 protein in serum from patients with breast cancer compared to normal control was tested. Serum was obtained from the UNC tissue procurement facility, where serum was collected under an IRB approved protocol. Patient serum was diluted 1:14 and filtered. The total protein level was measured using the Bio-Rad Protein assay. Equal amount of protein was loaded and Western blot was performed according to the standard method. The blot was probed with the SFRP2 antibody. It was found that SFRP2 is present in control and breast cancer patient serum but more highly expressed in the latter (p<0.0001, FIG. 24).

EXAMPLE 7

SFRP2 is a Broad Spectrum Vascular Target

Using IHC with antibodies to SFRP2 on paraffin-embedded human tumors, the vascular expression of SFRP2 in angiosarcoma, colon cancer, prostate cancer, lung cancer, ovarian cancer, hepatocellular carcinoma, renal cell carcinoma, and pancreatic cancer was evaluated. It was found that SFRP2 is strongly expressed in all tumors, making SFRP2 a broad spectrum vascular target (FIG. 25).

EXAMPLE 8

Tacrolimus Inhibits Angiogenesis In Vivo

Figure 26:
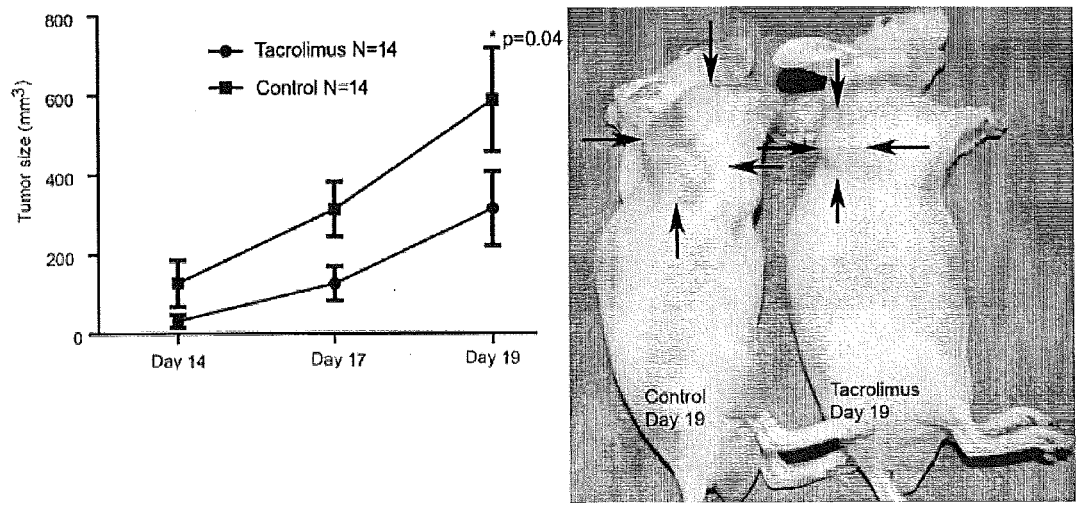
FIG. 26 shows that tacrolimus inhibits the growth of SVR angiosarcoma xenografts in nude mice. Picture shows representative control mouse tumor and representative tacrolimus treated mouse tumor on day 19 of treatment.

To test the ability of tacrolimus to inhibit angiogenesis in vivo, SVR mouse angiosarcoma cells ($0.5 \times 10^6$) were injected into the flank of 6-week-old nude male mice obtained from Charles River Breeding Laboratories. Treatment was initiated on the day after inoculation. Mice received 3 mg/kg/daily tacrolimus or vehicle control suspended in 20% Intralipid (Baxter Healthcare, Deerfield, Ill.) in a total volume of 0.3 ml intraperitoneally (i.p.), and were treated daily for 19 days. Serial caliper measurements of perpendicular diameters were used to calculate tumor volume using the following formula: (shortest diameter)$^2$×(longest diameter)×0.52. Differences in tumor volume over time were analyzed with a two way ANOVA. A P value of ≤0.05 indicated a statistically significant reduction in tumor growth of the treated group compared to the control group. Treatment with tacrolimus (n=14) for 19 days was effective at suppressing the growth of SVR angiosarcoma tumor in nude mice as compared with control (n=14). Treatment with tacrolimus reduced mean tumor volume by 46% at day 19 (589±129 mm$^3$ vs 315±93 mm$^3$, two-way ANOVA, p=0.04, FIG. 26). There were no signs of toxicity (i.e., no diarrhea, infection, lethargy, or weight loss) after 19 days of treatment.

Figure 27:
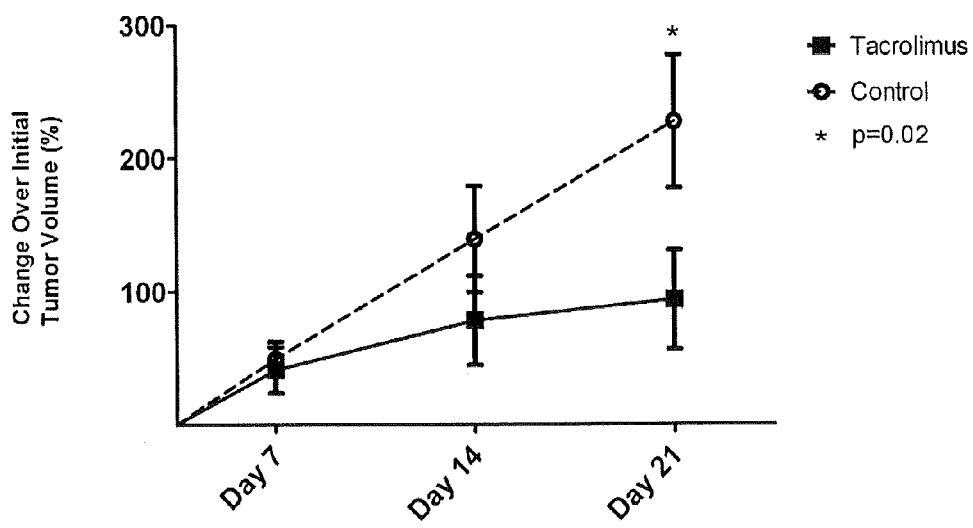
FIG. 27 shows that tacrolimus inhibits the growth rate of MMTV-neu transgenic mouse tumors (n=12 tacrolimus treated, n=9 no treatment, p=0.04).

In a second study, MMTV-neu transgenic mice were treated with tacrolimus 3 mg/kg/daily or no treatment. Treatment began when tumors were palpable and continued for 21 days. Tumor volumes were monitored with serial ultrasounds. A two-tailed T-test was used to determine the difference between growth rates of the tumors between treated and non-treated tumors. The groups were significantly different (P=0.04, two-tailed t-test) at the end of the study on day 21, with a 59% reduction in growth rate (FIG. 27). There were no signs of toxicity (i.e., diarrhea, infection, lethargy, or weight loss) after treatment.

EXAMPLE 9

Angiogenic Function of Jak3

Cell culture: Human coronary artery cells (HCAEC) were cultured in endothelial cell basal medium-2 (EGM-2) with BulletKit growth supplements (Clonetics, San Diego, Calif.). Cells were passaged at 80-90% confluence using trypsin without EDTA (Invitrogen, Carlsbad, Calif.). Passages 3-9 were used in experiments.

Figure 28:
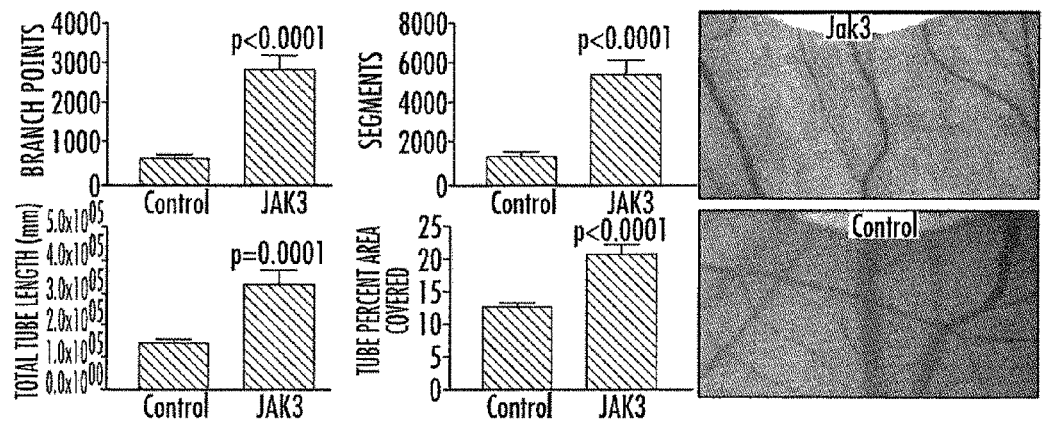
FIG. 28 shows the ability of Jak3 to promote angiogenesis in vivo using a chick chorioallantoic membrane (CAM) assay. The graphs show quantitative analysis of vessels surrounding control versus Jak3-treated disks. The photographs illustrate angiogenesis in vessels surrounding Jak3-treated versus control disks.

Chick chorioallantoic membrane (CAM) assay: Fertilized chickens eggs (NC State University Chicken Research Farm) were incubated at 100.4° F. in an egg turner (Model# 1588 Genesis Hova-Bator, GQF Mfg. Co., Inc.) for 3 days. On day 3, the eggs were cracked into sterile 100×25 mm dishes and incubated at 99° F., 5% $CO_2$, 65% humidity for 5 days. For application of drug onto the CAM, Whatman grade 1 filter paper was cut into circles with a 6 mm diameter paper punch and autoclaved. To decrease inflammatory effects of the disk, they were soaked in 1 ml of 3.0 mg/ml cortisone acetate in absolute ETOH and air dried for 60 min in a laminar flow hood under ultraviolet light. On day 8, disks were inoculated with 7 µl 0.1% BSA in PBS for control CAMs or 100 ng Jak3/7 µl, 0.1% BSA in PBS for Jak3-treated CAMs (n=16 control disks and n=16 Jak3-treated disks). Disks were then placed on the outer third of the CAM, 2-3 mm from a major vessel. CAMs were evaluated under a stereomicroscope on day 3 after disk placement. Pictures were taken with a Wild M-4 70 Macrosystem and angiogenesis was quantified using Metamorph Software with an angiogenesis module. After 3 days, Jak3 induced angiogenesis on the CAM with a statistically significant increase in number of branch points (0.0001), segments (0.0001), tube percent area covered (0.0001), and total tube length (0.0001) (FIG. 28).

Figure 29:
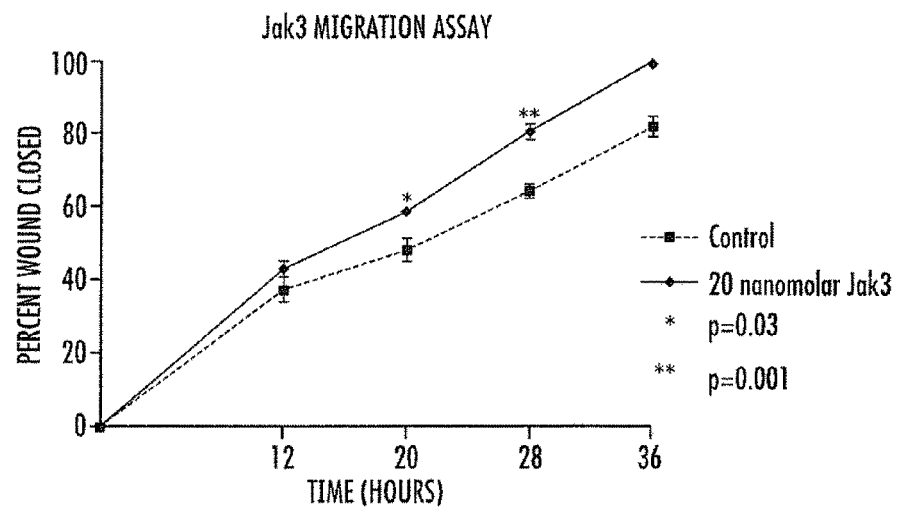
FIG. 29 shows the migration properties of Jak3 on HCAEC using a scratch wound assay. The graph shows quantitative analysis of the rate of wound closure in all wells. The photographs illustrate the relative wound closure of control versus Jak3-treated cells at 28 hours.

Scratch wound assay: HCAEC were plated at 10,000 cells/well onto a 96 well plate and allowed to become confluent in EGM-2 with BulletKit growth supplements. The cells were quiesced in EGM-2 with 0.1% FBS without BulletKi growth supplements for 18 hours. The wound was formed using a 1 ml pipette tip. A 20 nM-200 µM dose curve of recombinant human Jak3 (Millipore, Temecula, Calif.) was added to the cells. Each concentration was performed in triplicate and the experiment was repeated three times with similar results. Migration distance was measured at 12 hours and then every 4 hours until wound closure in all wells. Data were recorded as percent of wound closed at each time point. Jak3 increased endothelial cell migration in the nanomolar concentration (p<0.03 at 20 hours, p<0.001 at 28 hours) (FIG. 29).

Figure 30:
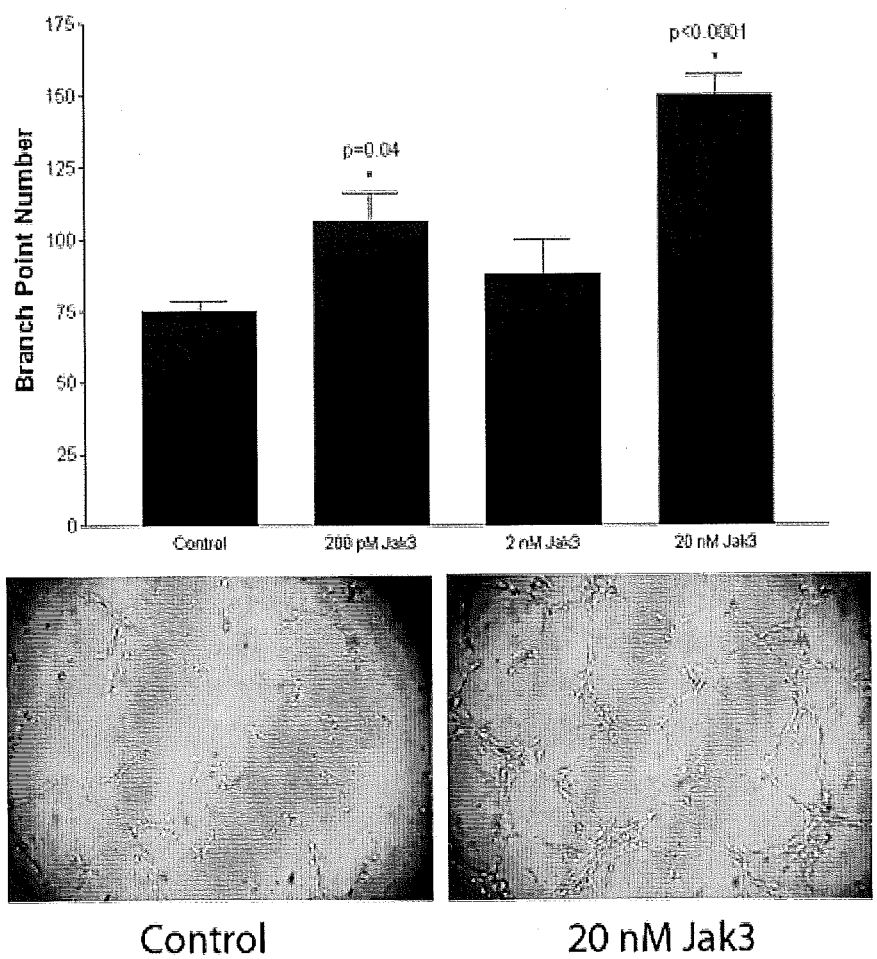
FIG. 30 shows the tube formation properties of Jak3 on HCAEC using an endothelial cell tube formation assay. The graph shows quantitative analysis of the number of branch points in all wells. The photographs illustrate the relative tube formation in control versus Jak3-treated cells.

Tube formation assay: ECMATRIX (Chemicon, Temecula, Calif.) was thawed, diluted, and solidified in a 96 well plate according to the manufacturer's instructions. HCAEC were seeded onto the matrix at 2,000 cells/well in 150 µl of EGM-2 with 5% FBS without BulletKit growth supplements. A 20 nM - 200 pM dose curve of recombinant human Jak3 was added to the cells and the plates were returned to 37° C., 5% $CO_2$ for 8 hours. Each concentration was performed in triplicate and the experiment was repeated three times with similar results. Wells were evaluated under a Nikon Eclipse TS100 microscope at 4×magnification and pictures were taken with a Nikon CoolPix 995 digital camera. Angiogenesis was quantified by counting branch points in the resulting image. Endothelial tube formation was induced by Jak3 in a concentration-dependent manner at 8 hours (p=0.04 at 200 pM, p=0.0001 at 20 nM) (FIG. 30).

Figure 31:
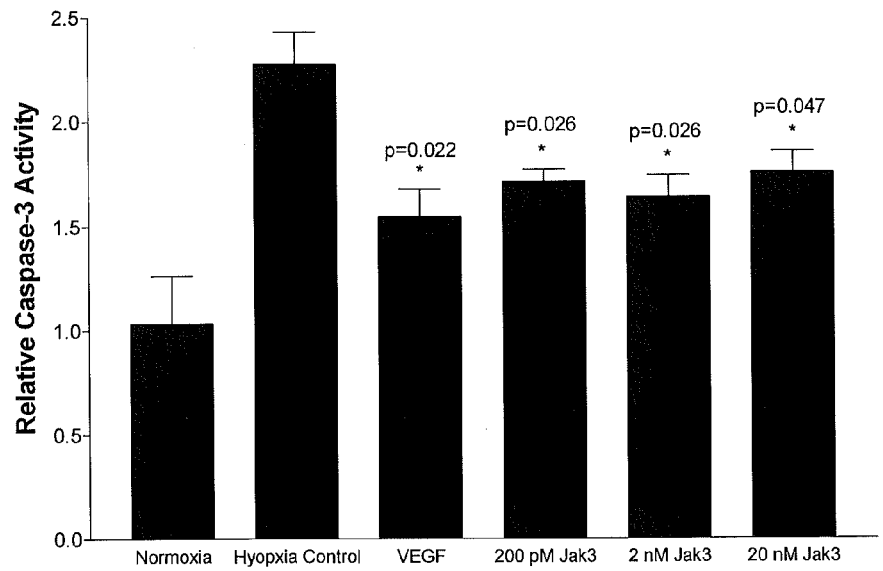
FIG. 31 shows the effect of Jak3 on hypoxia-induced apoptosis in HCAEC.

Endothelial cell apoptosis assay: HCAEC were seeded onto a 96 well plate at 2,000 cells/well in EGM-2 with BulletKit growth supplements. Cells were grown for 18 hours and media was replaced with EGM-2 without BulletKit growth supplements and a 20 nM-200 µM dose curve of recombinant human Jak3 was added to the cells. The plate was incubated in hypoxic conditions (37° C. in a hypoxia chamber with an atmosphere of 5% $CO_2$/95% $N_2$ with an oxygen level of 1.0%) for 36 hours. Apoptosis was determined by measuring the activity of cleaved caspase 3 by using a caspase-specific fluorogenic substrate according to the protocol for the Apo-ONES Homogeneous Caspase-3/7 Assay (Promega, Madison, Wis.). Briefly, control and treated HCAEC were lysed in 100 µL it of Apo-ONE 8 Caspase-3/7 reagent and incubated in that reagent at room temperature for 1 h. The caspase 3 activation of the profluorescent substrate rhodamine 110, bis-(N-CBZ-L-aspartyl-L-glutamyl-L-valyl-L-aspartic acid amide (Z-DEVD-R110) was measured by a fluorescence microplate reader. It was found that Jak3 protected against hypoxia induced endothelial cell apoptosis (p<0.05) (FIG. 31).

Figure 32:
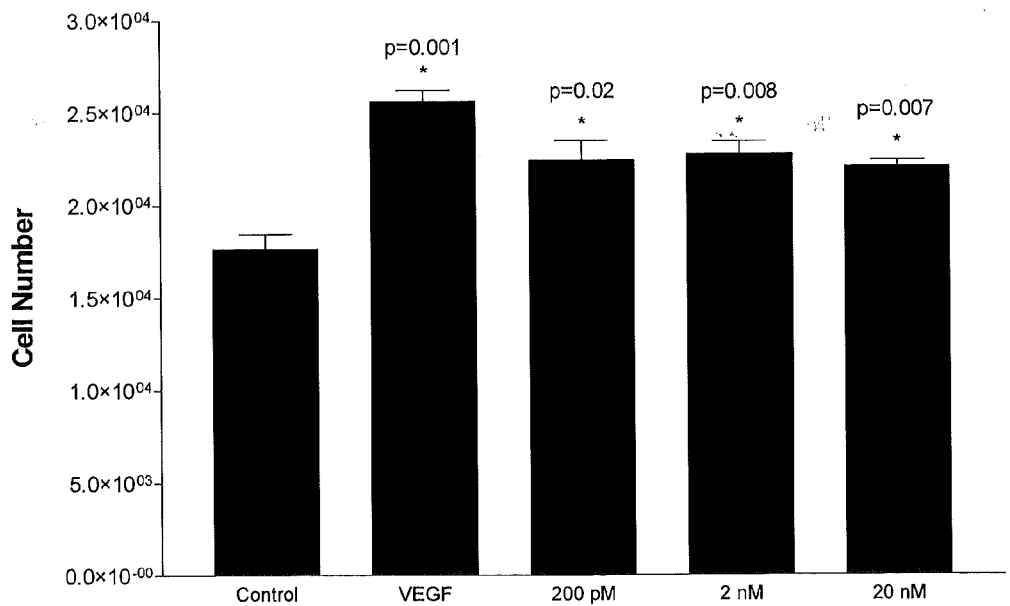
FIG. 32 shows HCAEC proliferation in the presence of Jak3.

Endothelial cell proliferation assay: HCAEC were seeded on a 96 well plate at a concentration of 2000 cells/well and allowed to proliferate for 24 hrs in EGM-2 with BulletKit growth supplements. The cells were then quiesced in EGM-2 with 0.1% FBS without BulletKit growth supplements for 18 hours. Media was replaced with fresh EGM-2 with BulletKit growth supplements and the cells were treated in triplicate with: PBS alone; recombinant murine VEGF (60 ng/mL); or Jak3 (at a concentration of 200 nM-200 µM). After 48 h, 10 µl of the colorimetric compound 3-(4,5-dimethylthiazol-2-yl)-2,5-diphenyl tetrazolium bromide (MTT) (5 mg/mL) was added to each well and allowed to incubate for 4 h at 37° C. All but 25 µl of media in each well was removed and 50 µl dimethyl sulfoxide (DMSO) was added. Following a 10 min incubation at 37° C., the A540 was measured using a microplate reader. A540 was converted to number of cells based on a standard curved created by seeding a 96-well plate with known concentrations of cells, as determined by hemocytometry, and measuring their A540 after 4 hrs incubation with MTT. Jak3 increased cell proliferation at 48 hours (p=0.007 at 20 nM) (FIG. 32).

Figure 33:
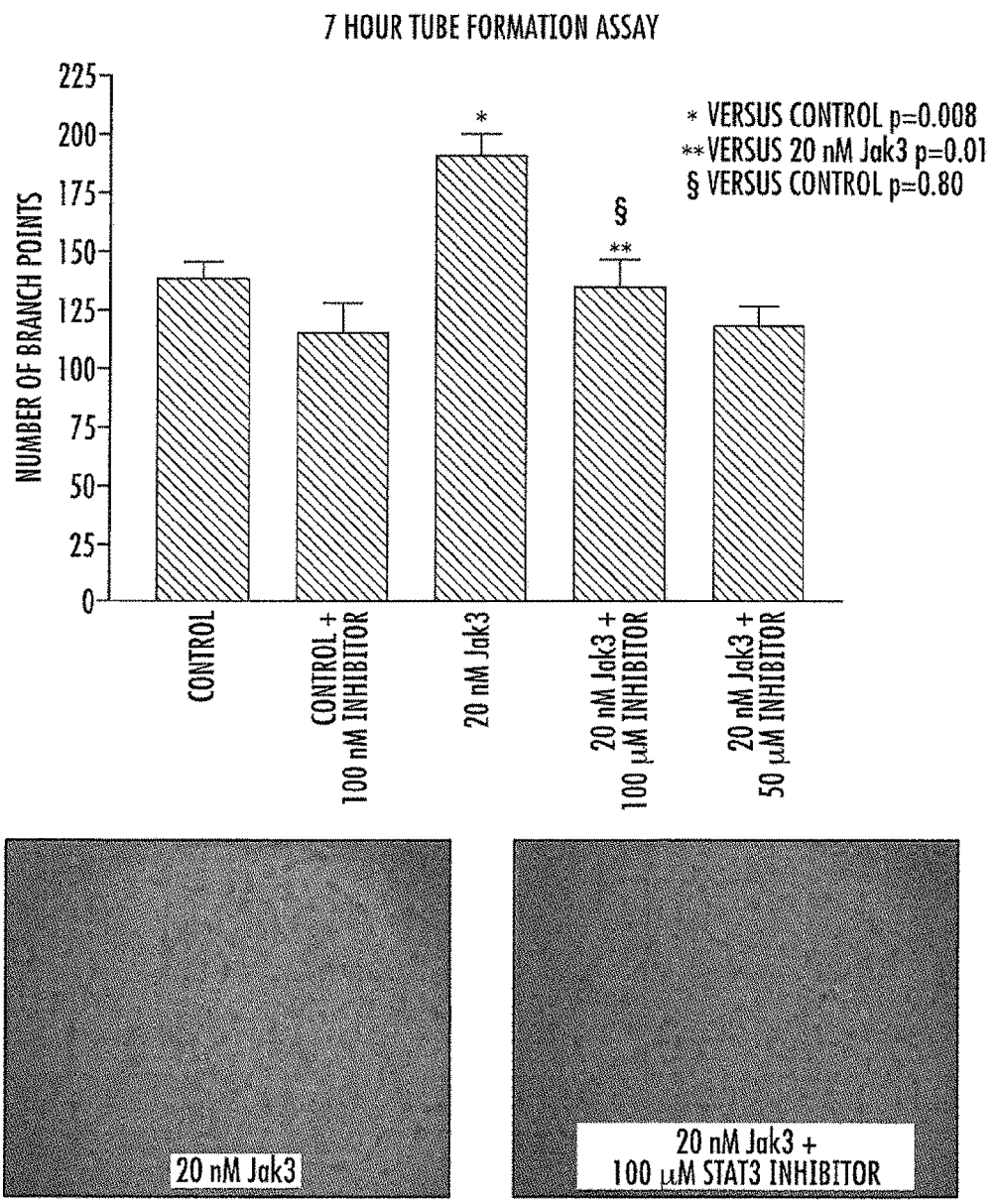
FIG. 33 shows the role of STAT3 activation in Jak3-mediated tube formation using a small peptide inhibitor of phosphorylated STAT3 (P-STAT3). The graph shows quantitative analysis of the number of branch points in all wells. The photographs illustrate the relative tube formation in Jak3-treated versus Jak3+P-STAT3 inhibitor-treated cells.

Effect of STAT3 on tube formation: The role of STAT3 activation in Jak3-mediated tube formation was evaluated using a small peptide inhibitor of phosphorylated STAT3 (P-STAT3).ECMATRIX was solidified in wells of a 96 well plate. HCAEC were seeded onto the matrix at 2,000 cells/well in 150 µl of EGM-2 with 5% FBS without additional BulletKit growth supplements. Wells were treated in triplicate with: PBS alone, PBS +100 µM P-STAT3 inhibitor, 20 nM Jak3, or 20 nM Jak3 +100 µM P-TAT3 inhibitor. Wells were photographed at 8 hours and tube formation was quantified by counting branch points in the resulting image. Addition of STAT3 inhibitor prevented Jak3-mediated tube formation, indicating that the Jak3 signal is mediated through the STAT3 pathway (FIG. 33).

EXAMPLE 10

SFRP2 Antibody Inhibits Tumor Growth In Vivo

Figure 34:
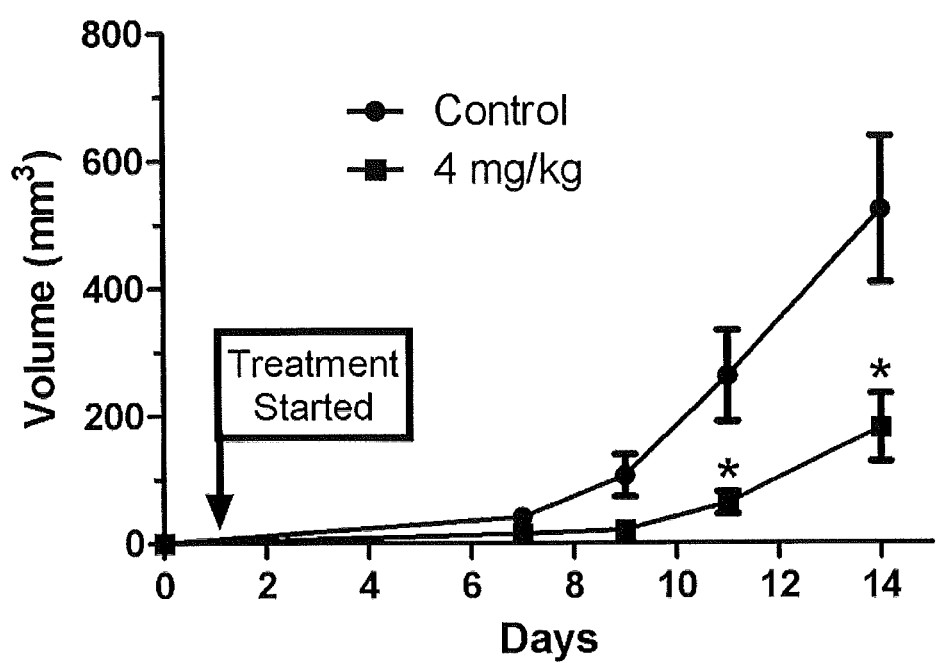
FIG. 34 shows that a SFRP2 monoclonal antibody inhibits the growth of SVR angiosarcoma xenografts in nude mice.

The ability of a monoclonal antibody recognizing SFRP2 to inhibit tumor growth in vivo was tested in a nude mouse assay. The SFRP2 MAb subclone 80.8.6 was first tested with SVR angiosarcoma xenografts. Six week old nude mice were injected with $1 \times 10^6$ SVR angiosarcoma cells. The day after injections treated mice received SFRP2 MAb (80.8.6) 4 mg/kg i.v. twice weekly (n=5), and controls received equal volumes of buffer. At day 14 there was a 65% decrease in tumor volume (*p=0.03, two-tailed student's t-test) (FIG. 34). No toxicity or weight loss was seen in the mice.

The SFRP2 MAb subclone 80.8.6 was next tested with MDA-MB-231 breast cancer xenografts. Six week old female nude mice were injected with $1 \times 10^6$ MDA-MB-231 cells. After 4 weeks, when tumors were palpable, mice received SFRP2 MAb (80.8.6) 4 mg/kg i.v. twice weekly (n=12), and controls received equal volumes of buffer. At day 8 the median tumor volume for controls was 1200 $mm^3$, and for SFRP2 MAb treated mice was 580 $mm^3$, which represents a 52% decrease in tumor volume (p=0.04, two-tailed student's t-test). No toxicity or weight loss was seen in the mice.

The foregoing is illustrative of the present invention, and is not to be construed as limiting thereof. The invention is defined by the following claims, with equivalents of the claims to be included therein.

That which is claimed is:

1. An isolated monoclonal antibody or an antigen binding fragment thereof which: (a) specifically binds an epitope comprised of amino acids selected from the group consisting of amino acids EITYINRDTKIILETKSKT-Cys (SEQ ID NO:6) and ITSVKRWQKGQREFKRISRSIRKLQC (SEQ ID NO:7); and (b) inhibits one or more of angiogenesis and tumor growth.

2. The monoclonal antibody or an antigen binding fragment thereof of claim 1, which is a chimeric antibody.

3. The monoclonal antibody or an antigen binding fragment thereof of claim 1, which is a humanized antibody.

4. The monoclonal antibody or an antigen binding fragment thereof of claim 1, comprising a heavy chain variable region comprising the amino acid sequence of SEQ ID NO:13.

5. The monoclonal antibody or an antigen binding fragment thereof of claim 1, comprising a light chain variable region comprising the amino acid sequence of SEQ ID NO:15.

6. The monoclonal antibody or an antigen binding fragment thereof of claim 1, comprising a heavy chain variable region comprising the amino acid sequence of SEQ ID NO:13 and a light chain variable region comprising the amino acid sequence of SEQ ID NO:15.

7. The monoclonal antibody or an antigen binding fragment thereof of claim 1, which specifically recognizes an epitope which is amino acids EITYINRDTKIILETKSKT-Cys (SEQ ID NO:6).

8. An isolated monoclonal antibody produced by hybridoma cell line UNC 68-80 (ATCC Deposit No. PTA-11762) or an antigen binding fragment thereof.

9. An isolated monoclonal antibody or an antigen binding fragment thereof which comprises a heavy chain variable region comprising the amino acid sequence of SEQ ID NO:13 and a light chain variable region comprising the amino acid sequence of SEQ ID NO:15.

* * * * *

UNITED STATES PATENT AND TRADEMARK OFFICE
CERTIFICATE OF CORRECTION

PATENT NO. : 8,734,789 B2
APPLICATION NO. : 12/945298
DATED : May 27, 2014
INVENTOR(S) : DeMore et al.

Page 1 of 1

It is certified that error appears in the above-identified patent and that said Letters Patent is hereby corrected as shown below:

In the Specification:
Column 5, Line 66: Please correct "(700 μM)" to read -- (700 pM) --

Column 36, Line 48: Please correct "Huang et a," to read -- Huang et al., --

Column 59, Lines 10 and 11: Please correct "(70 μM and 700 μM)" to read -- (70 pM and 700 pM) --

Column 59, Lines 60 and 61: Please correct "(700 μM)." to read -- (700 pM). --

Column 60, Line 11: Please correct "(700 μM)." to read -- (700 pM). --

Column 61, Line 15: Please correct "64%+(0.002)" to read -- 64% ± (0.002) --

Column 64, Line 65: Please correct "20 nM-200 μM" to read -- 20 nM - 200 pM --

Column 65, Line 27: Please correct "20 nM-200 μM" to read -- 20 nM - 200 pM --

Column 65, Line 34: Please correct "Apo-ONES" to read -- Apo-ONE® --

Column 65, Line 36: Please correct "Apo-ONE 8" to read -- Apo-ONE ® --

Column 65, Line 54: Please correct "200 nM-200 μM)." to read -- 200 nM - 200 pM). --

Signed and Sealed this
Nineteenth Day of May, 2015

Michelle K. Lee
*Director of the United States Patent and Trademark Office*